United States Patent
Tague et al.

(10) Patent No.: US 12,043,652 B2
(45) Date of Patent: Jul. 23, 2024

(54) ENGINEERED EXTRACELLULAR RECEPTOR CONSTRUCTS AND USES THEREOF

(71) Applicant: TRUSTEES OF BOSTON UNIVERSITY, Boston, MA (US)

(72) Inventors: Elliot Parker Tague, Brookline, MA (US); John T. Ngo, Boston, MA (US); Jeffrey Blye McMahan, Cambrige, MA (US)

(73) Assignee: TRUSTEES OF BOSTON UNIVERSITY

( * ) Notice: Subject to any disclaimer, the term of this patent is extended or adjusted under 35 U.S.C. 154(b) by 0 days.

(21) Appl. No.: 17/458,739

(22) Filed: Aug. 27, 2021

(65) Prior Publication Data

US 2022/0064252 A1    Mar. 3, 2022

Related U.S. Application Data

(60) Provisional application No. 63/071,581, filed on Aug. 28, 2020.

(51) Int. Cl.
*C07K 14/705* (2006.01)
(52) U.S. Cl.
CPC ........ *C07K 14/705* (2013.01); *C07K 2319/03* (2013.01)
(58) Field of Classification Search
CPC .......................... C07K 14/705; C07K 2309/03
See application file for complete search history.

(56) References Cited

U.S. PATENT DOCUMENTS 8,906,831 B2    12/2014 Eid et al.
2020/0115461 A1 *  4/2020 Evnin .............. C07K 14/70517

FOREIGN PATENT DOCUMENTS

WO        2007066106 A1    6/2007
WO    WO-2019164979 A1 *  8/2019  ............. A61K 35/17

OTHER PUBLICATIONS

Morsut et al. 2016 "Engineering Customized Cell Sensing and Response Behaviors Using Synthetic Notch Receptors", Cell. vol 164:780-791 (Year: 2016).*
Scheller et al. 2018 "Generalized extracellular molecule sensor platform for programming cellular behavior", Nature Chemical Biology, vol. 14:723-729 (Year: 2018).*
Cunningham-Bryant et al. 2019 "A Chemically Disrupted Proximity System for Controlling Dynamic Cellular Processes", JACS, vol. 141: 3352-3355. (Year: 2019).*
Barnea et al. "The genetic design of signaling cascades to record receptor activation." Proceedings of the National Academy of Sciences 105(1): 64-69 (2008).
Bolduc et al. "Nicastrin functions to sterically hinder γ-secretase-substrate interactions driven by substrate transmembrane domain." Proceedings of the National Academy of Sciences 113(5): E509-E518 (2016).
Chang et al. "Rewiring T-cell responses to soluble factors with chimeric antigen receptors." Nature chemical biology 14(3): 317-324 (2018).
Dong et al. "Directed molecular evolution of DREADDs: a generic approach to creating next-generation RASSLs." Nature protocols 5(3): 561-573 (2010).
Edbauer et al. "Reconstitution of γ-secretase activity." Nature cell biology 5(5): 486-488 (2003).
Gallinari et al. "Multiple enzymatic activities associated with recombinant NS3 protein of hepatitis C virus." Journal of virology 72(8): 6758-6769 (1998).
Kügler et al. "High affinity peptide inhibitors of the hepatitis C virus NS3-4A protease refractory to common resistant mutants." Journal of Biological Chemistry 287(46): 39224-39232 (2012).
Mazé et al. "Artificial signaling in mammalian cells enabled by prokaryotic two-component system." Nature chemical biology 16(2): 179-187 (2020).
Morsut et al. "Engineering customized cell sensing and response behaviors using synthetic notch receptors." Cell 164(4): 780-791 (2016).
Roybal et al. "Precision tumor recognition by T cells with combinatorial antigen-sensing circuits." Cell 164(4): 770-779 (2016).
Scheller et al. "Generalized extracellular molecule sensor platform for programming cellular behavior." Nature chemical biology 14(7): 723-729 (2018).

(Continued)

*Primary Examiner* — Neil P Hammell
*Assistant Examiner* — Kelly Nichet Hassell
(74) *Attorney, Agent, or Firm* — Nixon Peabody LLP; Ronald I. Eisenstein

(57) ABSTRACT

Described herein are methods and compositions related to a modular engineered receptor polypeptide construct and their use in methods to modulate the activity of a cell. In particular, the disclosure relates to an engineered receptor polypeptide comprising, in brief, (i) an extracellular ligand binding domain having at least one ligand binding site, (ii) an optional flexible polypeptide linker, (iii) an intramolecular peptide that binds to the at least one ligand binding site in the extracellular ligand binding domain, (iv) a transmembrane domain comprising at least one γ-secretase cleavage site, and (v) an intracellular effector domain, where the intramolecular peptide that serves to regulate the activity of the engineered receptor polypeptide. Other aspects relate to cells comprising the engineered receptor polypeptide, and nucleic acid sequence encoding the engineered receptor polypeptide.

20 Claims, 13 Drawing Sheets

Specification includes a Sequence Listing.

(56) References Cited

OTHER PUBLICATIONS

Schwarz et al. "Rewiring human cellular input-output using modular extracellular sensors." Nature chemical biology 13(2): 202-209 (2017).
Zhao et al. "A genetically encoded probe for imaging HA-tagged protein translation, localization, and dynamics in living cells and animals." bioRxiv: 474668 (2018).
Dakshanamurthy. "Predicting New Indications for Approved Drugs Using a Proteo—Chemometric Method" 1. NIH Public Access. Web. Aug. 9, 2012; Abstract.

* cited by examiner

ENGINEERED EXTRACELLULAR RECEPTOR CONSTRUCTS AND USES THEREOF

CROSS-REFERENCE TO RELATED APPLICATIONS

This application claims benefit under 35 U.S.C. § 119(e) to U.S. Provisional Application No. 63/071,581 filed Aug. 28, 2020, the contents of which is incorporated herein by reference in its entirety.

GOVERNMENT SUPPORT

This invention was made with government support under Grant No. GM128859, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 16, 2022, is named 701586-098300USPT_SL.txt and is 22,914 bytes in size.

TECHNICAL FIELD

The technology described herein relates to engineered receptor polypeptide constructs and uses thereof.

BACKGROUND

In natural biological processes, cells are continuously sensing their environment and respond with the appropriate cellular output. This can help cells maintain homeostasis or carry out new biological actions such as differentiation into new cell type/tissues, mount an immunological response, or signal for other complex cascades like apoptosis. As researchers and clinicians, it is often desired to engineer synthetic controls of biological processes to create complex gene networks or to control a cellular function with the use of a synthetic ligand.

SUMMARY

The methods and compositions described herein are based, in part, on the development of a platform to create modular and customizable cellular biosensors in which the user can specifically define the input ligand the cell senses to generate a customized genetic output or protein release response. In one embodiment, the methods and compositions described herein permit the detection of free floating or bound small molecules, peptides, or proteins and generate output responses like gene activation, split protein complementation, or cleavage mediated protein activity. The sensors described herein vary from previous sensors in that they do not comprise a Notch regulatory region (NRR), which can render the sensors insensitive to force or stretch of the cell membrane in which the engineered receptor is expressed.

Accordingly, provided herein in one aspect is an engineered receptor polypeptide construct comprising: (i) an extracellular ligand binding domain having at least one ligand binding site, (ii) an optional flexible polypeptide linker, (iii) an intramolecular peptide that binds to the at least one ligand binding site in the extracellular ligand binding domain, (iv) a transmembrane domain comprising at least one γ-secretase cleavage site, and (v) an intracellular effector domain, wherein when the intramolecular peptide is bound to the at least one ligand binding site, the extracellular ligand binding domain is maintained in a position that sterically inhibits γ-secretase from cleaving the construct at the at least one γ-secretase cleavage site, and wherein, in the presence of a cognate ligand, the intramolecular peptide is displaced, thereby releasing the extracellular ligand binding domain to a conformation that permits gγ-secretase to cleave the construct at the at least one γ-secretase cleavage site and the intracellular effector domain is released, thereby producing an effect in the cell in which the engineered receptor construct is expressed.

In one embodiment, the extracellular ligand binding domain does not comprise a Notch regulatory region (NRR). In another embodiment, the extracellular ligand binding domain is insensitive to force or stretch of the cell membrane in which the engineered receptor is expressed.

In one embodiment of this aspect and all other aspects provided herein, the optional flexible linker comprises at least 2 amino acids and no more than 300 amino acids.

In one embodiment of this aspect and all other aspects provided herein, the transmembrane domain comprises the sequence:

```
                                        (SEQ ID NO: 49)
       PVEPPLPSQLHLMYVAAAAFVLLFFVGCGVLLSRKRRR.
```

In another embodiment of this aspect and all other aspects provided herein, the intramolecular peptide has a lower, equal or greater affinity of binding to the ligand binding site than the cognate ligand.

In another embodiment of this aspect and all other aspects provided herein, the intramolecular peptide does not inhibit gamma-secretase binding when placed at the juxtacrine position of the transmembrane domain.

In another embodiment of this aspect and all other aspects provided herein, the intramolecular peptide is an engineered peptide or a naturally occurring peptide.

In another embodiment of this aspect and all other aspects provided herein, the engineered peptide is derived from phage display, directed evolution, or rational design.

In another embodiment of this aspect and all other aspects provided herein, the intracellular effector domain comprises a transcription factor, a fluorescent protein, a protein marker, an enzyme, an enzyme subdomain, a cytotoxic protein, a dominant negative polypeptide, a nucleic acid, a therapeutic protein, a epigenetic regulator protein, or a peptide.

In another embodiment of this aspect and all other aspects provided herein, the nucleic acid comprises an mRNA, an miRNA, an shRNA, an siRNA, a dsRNA, or an antisense nucleotide.

In another embodiment of this aspect and all other aspects provided herein, the fluorescent protein comprises green fluorescence protein (GFP), yellow fluorescence protein (YFP), enhanced GFP (EGFP), enhanced YFP (EYFP), blue fluorescent protein (BFP), superfolder GFP (sfGFP), cyan fluorescent protein (ECFP), FITC, rhodamine, mCherry, mOrange, or mStrawberry.

In another embodiment of this aspect and all other aspects provided herein, the enzyme comprises Cas9, dCas9, a zinc finger protease, a chemiluminescent enzyme, a therapeutic enzyme, a metabolic enzyme, an apoptotic enzyme, or a DNA repair enzyme.

In another embodiment of this aspect and all other aspects provided herein, the cytotoxic protein comprises a pro-apoptotic protein, diphtheria toxin A fragment, botulinum toxin, exotoxin A, ricin A chain, abrin A chain, modeccin A chain, α-sacrin, curcin, crotin, gelonin, mitogillin, restrictocin, phenomycin, neomycin, a *Shigella* toxin, pertussis toxin, CagA, VopQ, or YopH.

In another embodiment of this aspect and all other aspects provided herein, the therapeutic protein comprises replacement of a damaged or missing protein in a given disease or disorder.

In another embodiment of this aspect and all other aspects provided herein, the intracellular effector domain further comprises an intracellular targeting or localization sequence.

In another embodiment of this aspect and all other aspects provided herein, the intracellular targeting or localization sequence comprises a nuclear targeting sequence, a mitochondrial targeting sequence, an endoplasmic reticulum targeting sequence, a peroxisomal targeting sequence, a plasma membrane targeting sequence, a trans-Golgi targeting sequence or a lysosomal targeting sequence.

In another embodiment of this aspect and all other aspects provided herein, the extracellular ligand binding domain further comprises at least a second ligand binding site that does not bind the intramolecular peptide and binding of the ligand to this site does not induce cleavage of the intracellular effector domain, wherein when a ligand binds to the second ligand binding sites, the overall conformation is such that it is easier for a ligand to displace the intramolecular peptide from the first ligand binding site than if the ligand is not bound to the second ligand binding site, or wherein binding of a ligand to the second ligand binding sites increases the avidity of the ligand to the first ligand binding site and increases the length of time that the ligand binds by altering the dynamic equilibrium kinetics.

In another embodiment of this aspect and all other aspects provided herein, the transmembrane domain comprises a Notch receptor transmembrane domain.

In another embodiment of this aspect and all other aspects provided herein, the extracellular ligand binding domain comprises a receptor binding domain, an antibody binding domain, a single-chain variable fragments (scFv), a nanobody, a naturally occurring protein binding domain, a peptide, or a rationally designed protein with ligand affinity.

In another embodiment of this aspect and all other aspects provided herein, the cognate ligand is soluble or tethered.

In another embodiment of this aspect and all other aspects provided herein, the cognate ligand is an antigen, a drug, an analyte, a protein, a peptide, a nucleic acid, a glycoprotein, a small molecule, a carbohydrate, a lipid, a glycolipid, a lipoprotein, or a lipopolysaccharide.

Another aspect provided herein relates to a nucleic acid sequence encoding the engineered receptor polypeptide construct as described herein.

Also provided herein, in another embodiment, is a cell expressing an engineered receptor polypeptide construct as described herein.

In one embodiment of this aspect and all other aspects provided herein, the cell is a human cell.

In another embodiment of this aspect and all other aspects provided herein, the cell is a therapeutic cell.

In another embodiment of this aspect and all other aspects provided herein, the cell is a chimeric antigen receptor T cell (CAR T cell), an embryonic stem cell, an induced pluripotent stem cell, a progenitor cell, or a differentiated cell.

In another embodiment of this aspect and all other aspects provided herein, the cell is a bacterial cell, a prokaryotic cell, an animal cell, a eukaryotic cell, or a plant cell.

Another aspect provided herein relates to a method of modulating expression of a gene product in a cell, the method comprising: (i) expressing the engineered receptor polypeptide construct as described herein in a cell, wherein the intracellular domain comprises a transcription factor, a dominant negative polypeptide, or an epigenetic regulator protein, (ii) optionally providing the cognate ligand, wherein in the presence of the cognate ligand, the intracellular effector domain is released from the engineered receptor polypeptide by γ-secretase cleavage, thereby modulating expression of the gene product in the cell.

In one embodiment of this aspect and all other aspects provided herein, the gene product is a nucleic acid gene product or a protein gene product.

In another embodiment of this aspect and all other aspects provided herein, the nucleic acid gene product comprises mRNA, miRNA, shRNA, siRNA, dsRNA, or an antisense nucleotide.

In another embodiment of this aspect and all other aspects provided herein, the protein gene product is a secreted protein.

In another embodiment of this aspect and all other aspects provided herein, expression of the gene product is increased.

In another embodiment of this aspect and all other aspects provided herein, expression of the gene product is reduced or inhibited.

In another embodiment of this aspect and all other aspects provided herein, the intracellular effector domain comprises an intracellular targeting sequence.

In another embodiment of this aspect and all other aspects provided herein, the intracellular targeting sequence comprises a nuclear targeting sequence, a mitochondrial targeting sequence, an endoplasmic reticulum targeting sequence, a peroxisomal targeting sequence, a plasma membrane targeting sequence, a trans-Golgi targeting sequence or a lysosomal targeting sequence.

In another embodiment of this aspect and all other aspects provided herein, the cognate ligand is a drug, an antigen, or a secreted protein expressed by the cell or a neighboring cell.

In another embodiment of this aspect and all other aspects provided herein, the drug is an FDA-approved drug.

In another embodiment of this aspect and all other aspects provided herein, the cognate ligand is a naturally occurring ligand or antigen.

Another aspect provided herein relates to a method of inducing cell death selectively in a cell, the method comprising: (i) expressing the engineered receptor polypeptide construct as described in any embodiment herein in a cell, wherein the cell is a therapeutic cell, an unwanted cell type in a cell manufacturing procedure, or a bacterial cell, wherein the intracellular domain comprises a cytotoxic protein or a pro-apoptotic protein, (ii) optionally providing the cognate ligand, wherein in the presence of the cognate ligand, the intracellular effector domain is released from the engineered receptor polypeptide by γ-secretase cleavage, thereby inducing cell death in the cell.

In one embodiment of this aspect and all other aspects provided herein, the cognate ligand is a drug.

In another embodiment of this aspect and all other aspects provided herein, the drug is an FDA-approved drug.

In another embodiment of this aspect and all other aspects provided herein, the cognate ligand is a naturally occurring ligand or antigen.

In another embodiment of this aspect and all other aspects provided herein, the therapeutic cell comprises a CAR T cell, an embryonic stem cell, an induced pluripotent stem cell, a progenitor cell, a probiotic or a differentiated cell.

Another aspect provided herein relates to a method of sensing an analyte, the method comprising: expressing the engineered receptor polypeptide construct as described herein in a cell, wherein the intracellular effector domain comprises a detectable product, wherein the analyte displaces the intramolecular peptide and binds to the at least one ligand binding site on the extracellular ligand binding domain, wherein in the presence of the analyte, the intracellular effector domain is released from the engineered receptor polypeptide by γ-secretase cleavage, thereby inducing expression of the detectable product in the cell.

In one embodiment of this aspect and all other aspects provided herein, the intracellular effector domain comprises a fluorescent protein, a chemiluminescent enzyme, a colorimetric marker, or an enzyme.

In another embodiment of this aspect and all other aspects provided herein, the analyte is detected in a cellular microenvironment or in solution.

In another embodiment of this aspect and all other aspects provided herein, the cellular microenvironment comprises a tumor microenvironment.

Also provided herein, in another aspect, is a method of inducing expression of a chimeric antigen receptor in a T cell in the presence of a target antigen, the method comprising: expressing the engineered receptor polypeptide construct of claim 1 in a T cell that also comprises a nucleic acid construct encoding a chimeric antigen receptor under the control of an inducible promoter, wherein the intracellular effector domain comprises an agent that binds the inducible promoter to induce expression of the chimeric antigen receptor, wherein when the ligand binding site on the extracellular ligand binding domain is bound to an antigen present on a target cell or bound to a soluble antigen present in a target cellular microenvironment, the intracellular effector domain is released from the engineered receptor polypeptide construct by γ-secretase cleavage, thereby inducing expression of the chimeric antigen receptor in the cell.

In another embodiment of this aspect and all other aspects provided herein, the target cell is a cancer cell.

In another embodiment of this aspect and all other aspects provided herein, the target cellular microenvironment comprises a tumor microenvironment.

In another embodiment of this aspect and all other aspects provided herein, the antigen present on a target cell comprises a cancer cell antigen.

In another embodiment of this aspect and all other aspects provided herein, the soluble antigen present in the target cellular microenvironment comprises a soluble protein secreted from a cancer cell.

In another embodiment of this aspect and all other aspects provided herein, the soluble protein secreted from a cancer cell comprises a growth factor, a cytokine, a chemokine, an interferon, or an extracellular matrix degrading enzyme.

Also provided herein, in another aspect, is a method for inducing an immune response in a subject, the method comprising: expressing the engineered receptor polypeptide construct as described herein in an immune cell, wherein the intracellular effector domain comprises an agent that activates the immune cell or induces expression of a secreted protein that activates a second immune cell, wherein when the engineered receptor polypeptide construct binds a target antigen present on a target cell or binds a soluble target antigen present in a target cellular microenvironment, the intracellular effector domain is released from the engineered receptor polypeptide by γ-secretase cleavage, thereby inducing an immune response in the subject.

In another embodiment of this aspect and all other aspects provided herein, the agent that activates the immune cell or the secreted protein that activates a second immune cell comprises a cytokine, a chemokine, an interferon, an interleukin.

In another embodiment of this aspect and all other aspects provided herein, the agent that activates the immune cell comprises a Toll-like receptor or ligand thereof.

In another embodiment of this aspect and all other aspects provided herein, the immune cell or second immune cell comprises a T cell, a B cell, a mast cell, a granulocyte, a basophil, a neutrophil, an eosinophil, a monocyte, a dendritic cell, or a natural killer cell.

In another embodiment of this aspect and all other aspects provided herein, the immune cell expressing the engineered receptor polypeptide construct is the same or different from the second immune cell.

Another aspect provided herein relates to an engineered receptor polypeptide construct with enhanced avidity, the construct comprising: (i) an extracellular ligand binding domain having a first and second ligand binding site, (ii) an optional flexible polypeptide linker, (iii) an intramolecular peptide that binds to a ligand binding site in the extracellular ligand binding domain, (iv) a transmembrane domain comprising at least one γ-secretase cleavage site, and (v) an intracellular effector domain, wherein the first ligand binding site does not bind to the intramolecular peptide, wherein the second ligand binding site binds to the intramolecular peptide, wherein when the intramolecular peptide is bound to the second ligand binding site, the extracellular ligand binding domain is maintained in a position that sterically inhibits γ-secretase from cleaving the construct at the at least one γ-secretase cleavage site, wherein, in the presence of a cognate ligand, the intramolecular peptide is displaced from the second ligand binding site, thereby releasing the extracellular ligand binding domain to a conformation that permits γ-secretase to cleave the construct at the at least one γ-secretase cleavage site and the intracellular effector domain is released, and wherein binding of the ligand to the first ligand binding site increases the avidity of the engineered receptor polypeptide construct by modulating the dynamic equilibrium of ligand on/off time and increasing the amount of time the ligand is bound to the second ligand binding site.

In one embodiment of this aspect and all other aspects provided herein, the first ligand binding site and second ligand binding sites bind the same ligand.

In another embodiment of this aspect and all other aspects provided herein, the first ligand binding site and second ligand binding sites bind different ligands.

In another embodiment of this aspect and all other aspects provided herein, the amount of time the ligand is bound to the second ligand binding site is increased by at least 10%.

Another aspect provided herein relates to a template nucleic acid encoding an engineered receptor polypeptide construct operably linked to a promoter.

In one embodiment of this aspect and all other aspects provided herein, the promoter is a tissue-specific promoter.

Another aspect provided herein relates to a viral vector or plasmid containing the template nucleic acid as described herein.

In another embodiment of this aspect and all other aspects provided herein, the viral vector is a lentivirus, a parvovirus, an adenovirus, or an adenovirus associated vector (AAV).

Another aspect provided herein relates to a lipofection reagent in an admixture with the template nucleic acid or a viral vector or plasmid as described herein.

In one embodiment of any aspect provided herein, the extracellular ligand binding domain does not comprise a Notch regulatory region (NRR). In another embodiment, the extracellular ligand binding domain is insensitive to force or stretch of the cell membrane in which the engineered receptor is expressed.

BRIEF DESCRIPTION OF THE DRAWINGS

(FIG. 2A) Schematic of antiviral drug sensor which is designed to sense Hepatitis C Virus NS3 inhibitors. (FIG. 2B) Two sensors with varying sensitivity to antiviral drug based on the affinity of their intramolecular peptide. Activity of the sensor is shown as histograms of intracellular domain driven H2B-mCherry expression in clonal cell lines, measured by flow cytometry, 48 hours post-drug addition. In the high sensitivity sensor, peptide is low affinity cut site amino acid sequence, DEEMEEC (SEQ ID NO: 54). In the intermediate sensitivity sensor, peptide is high affinity peptide, CP5-46A-4D5E. Red arrows are drawn to highlight differences in sensitivity to ligand. Drug is grazoprevir or delivery vehicle control, DMSO.

(FIG. 5A) Myc epitope is fused to the N-terminus of each construct. (FIG. 5B) Surface staining is detected via anti-myc tag antibody conjugated to Alexafluor 647 dye, followed by fixation with paraformaldehyde. A fluorescent transfection marker is shown as a smaller corresponding image. Surface staining was performed 48 hours after transfection and appropriate drug inducer. Drug concentrations are as follows: NS3 inducer, grazoprevir 3 μM; BCL-xL inducer, ABT-737 3 μM. Scale bar 20 μm.

(FIG. 7B) Upon presentation of surface bound ligand anti-myc antibody, the myc epitope of the sensor is engaged and results in ICD driven H2B-mCherry expression. In absence of ligand on fibronectin (Fn), no minimal H2B-mCherry expression is observed. Cells were imaged 24 hours after transfection and ligand addition. A fluorescent transfection marker is shown in blue. Scale bar 100 μm.

(FIG. 10B) Upon presentation of fibronectin (Fn) with GFP tagged with HA peptide epitope, the sensor ICD is cleaved to drive expression of H2B-mCherry reporter gene. Presentation of Fn in absence of GFP-HA ligand results in minimal H2B-mCherry activation. Fold activation of H2B-mCherry is normalized to a control of a iRFP fluorescent marker only. Fluorescence was measured with flow cytometry, 48 hours post transfection and ligand presentation. Non-coated plates were treated with either Fn (5 μg/mL) or Fn supplemented with 6.6 μM GFP-HA for 1 hr at room temperature, followed by three PBS washes before seeding.

DETAILED DESCRIPTION

Figure 1:
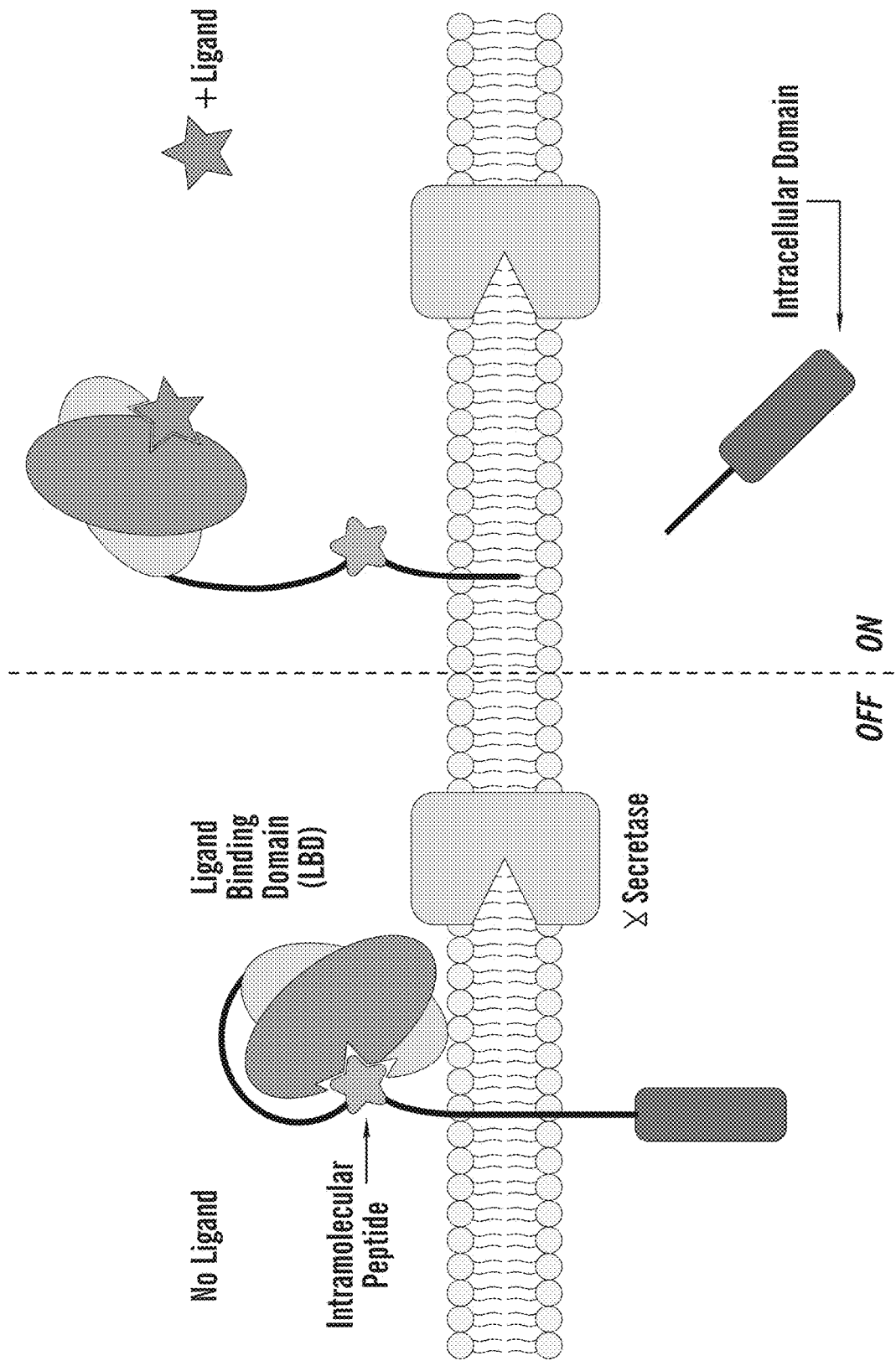
FIG. 1 Schematic of a generic MIMOsensor design. In the case of no ligand, the ligand binding domain is intramolecularly bound to an autoinhibitory peptide. This conformation intramolecularly inhibits the gamma secretase complex from cleaving its transmembrane substrate. In the presence of ligand, the ligand binding domain is competitively displaced from the intramolecular peptide and allows access to gamma secretase to cleave the transmembrane domain. Gamma secretase cleavage triggers the release an intracellular domain.

Provided herein are engineered receptor polypeptide constructs that can be designed in a modular fashion to bind to a desired ligand and produce a desired ligand-mediated output in a cell. The engineered receptor polypeptides comprise an extracellular ligand binding domain that can be designed to bind to a ligand, such as an antigen, a small molecule, a drug, an analyte, among others. The engineered receptor polypeptide constructs described herein differ from other engineered receptors because they comprise a single unit, lack a Notch regulatory region and can bind soluble ligands. Also provided herein are methods of using such engineered receptor polypeptide constructs for e.g., modulating expression of a gene product in a cell (e.g., an endogenous or heterologous gene product), improving targeting of chimeric antigen receptor T cells (CAR T cells), sensing an analyte in a cell, cellular microenvironment or solution, or for selectively killing a cell. In one embodiment, the extracellular ligand binding domain does not comprise a Notch regulatory region (NRR). In another embodiment, the extracellular ligand binding domain is insensitive to force or stretch of the cell membrane in which the engineered receptor is expressed.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

Definitions of common terms in cellular and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

As used herein, the term "flexible polypeptide linker" refers to a polypeptide sequence having sufficient flexibility that the extracellular binding domain tethered to one end of the flexible linker can curl back and bind the intramolecular peptide within or at the opposite end of the flexible polypeptide linker. In addition, the linker must have sufficient length that when the intramolecular peptide is displaced from the ligand binding site, the extracellular ligand binding domain can move sufficiently far away to remove the steric hindrance and permit access of cell membrane γ-secretase to the γ-secretase cleavage site in the transmembrane domain of the engineered receptor polypeptide construct. As will be appreciated by those of skill in the art, a flexible linker will comprise less than 3, 2, or 1 inflexible amino acid(s) (e.g., proline). In some embodiments, the flexible linker lacks inflexible amino acids. In some embodiments, the flexible polypeptide linker comprises at least 2 amino acids but fewer than 300 amino acids. In some embodiments, the engineered receptor does not comprise a flexible linker and rather utilizes a flexible region that is part of the extracellular ligand binding domain (e.g., a naturally occurring flexibility in the selected extracellular ligand binding domain). Exemplary linker sequences include, but are not limited to, GGGS (SEQ ID NO: 55) repeats, GGS (SEQ ID NO: 58) repeats, or flexible linker sequences with rigid linker sub-domains (ex. EAAAK (SEQ ID NO: 56)) aka "semi-flexible linkers."

As used herein, the term "intramolecular peptide" refers to a peptide that binds to at least one ligand binding site on the extracellular ligand binding domain and comprises a weaker affinity than the cognate ligand to which the engineered receptor polypeptide construct is designed to respond to. That is, the intramolecular peptide comprises a lower affinity than the cognate ligand such that the cognate ligand can displace the intramolecular peptide via competitive binding kinetics at a given concentration.

As used herein, the term "cognate ligand" is used herein to refer to the ligand to which the extracellular ligand binding site is designed to bind. The cognate ligand need not be a naturally occurring ligand for the ligand binding site.

As used herein, the term "therapeutic cell" refers to any cell that is administered to a subject for the purpose of treating a disease or disorder. Examples of therapeutic cells include CAR T cells, other immune cells, embryonic stem cells, induced pluripotent stem cells, progenitor cells, hematopoietic stem cells, engineered cells or differentiated cells. In some embodiments, the therapeutic cell comprises a kill switch using the engineered receptor polypeptide constructs described herein to allow a clinician to selectively kill cells that have been administered, for example, to stop their effect or to prevent widespread cytokine storms associated with administered cells.

The terms "decrease", "reduced", "reduction", or "inhibit" are all used herein to mean a decrease or lessening of a property, level, or other parameter by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased," "increase," "increases," or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

The term "statistically significant" or "significantly" refers to statistical significance and generally means a two standard deviation (2SD) or greater difference.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean ±1%.

Engineered Receptors (MIMOsensors)

The engineered receptor constructs described herein (also referred to as a "MIMOsensor" (Modular Input Modular Output Sensor)) are composed of variable elements. The subdomains of the sensor comprise or consist essentially of (i) a Ligand Binding Domain, (ii) an intramolecular peptide, (iii) a transmembrane domain, and (iv) an intracellular domain. The extracellular ligand binding domain when bound to the intramolecular peptide exists in a conformation that sterically prohibits access of γ-secretase in the cell membrane with the γ-secretase cleavage domain in the receptor, thus the intracellular domain is retained as part of the engineered receptor. However, upon competitive inhibition of a ligand (e.g., a high affinity ligand) in an amount sufficient to displace the intramolecular peptide, the extracellular ligand binding domain conformation opens up to permit access and cleavage of the γ-secretase cleavage domain by γ-secretase, thus releasing the intracellular domain from the inner surface of the membrane and the engineered receptor. Each element of this construct can be modified or selected in a modular manner based on the desired function of the engineered receptor polypeptide construct in a cell.

Extracellular Ligand Binding Domain: the extracellular ligand binding domain (LBD) can comprise any chimeric protein or protein domain that displays affinity toward any substance and comprises at least one ligand binding site for a desired ligand. This includes, but is not limited to, small molecules, peptide motifs, 3D protein epitopes, and large macromolecular structures. Examples of ligand binding domains are antibody binding domains, single-chain variable fragments (scFv), nanobodies, naturally occurring protein binding domains, peptides, and rationally designed proteins with ligand affinity. In one embodiment, the extracellular ligand binding domain does not comprise a Notch regulatory region (NRR). In another embodiment, the extracellular ligand binding domain is insensitive to force or stretch of the cell membrane in which the engineered receptor is expressed.

In some embodiments, the extracellular ligand binding domain comprises a naturally occurring or "built-in" flexible or hinge-like linker domain at the C-terminus, thus the engineered receptor does not comprise a flexible linker.

Intramolecular peptide: the intramolecular peptide comprises any peptide motif, either engineered or naturally occurring, which does not inhibit gamma-secretase binding when placed at the juxtacrine position of the transmembrane domain and can bind to the extracellular ligand binding domain with sufficient strength that the extracellular ligand binding domain is held in a conformation that sterically prevents γ-secretase cleavage and subsequent release of the intracellular effector domain. This includes naturally occurring peptide domains known to interact with a ligand binding domain or engineered peptides derived from techniques such as phage display, directed evolution, or rational design. An intramolecular peptide should be designed to have sufficient affinity of binding to the ligand binding site in the extracellular ligand binding domain to retain the closed conformation of the engineered receptor polypeptide construct, however the affinity should be lower than the cognate ligand such that the cognate ligand can displace the intramolecular peptide at an appropriate concentration of the ligand (e.g., a concentration that does not adversely affect cell viability or induce an undesirable effect in a subject). In some embodiments, the $K_D$ of the intramolecular peptide is within the range of 0.001 μM to 50 μM.

Without wishing to be bound by theory, the sensitivity of the sensors is likely approximated at least in part by standard competitive inhibition models (e.g., Michaelis Menten kinetics), so while there aren't necessarily limits to fold difference between ligand binding domain and intramolecular peptide, the resultant sensitivity will be affected (e.g. the stronger the intramolecular peptide binding, the lower the sensitivity of the sensor). Thus, in some embodiments, the sensors described herein can comprise approximately 100-fold difference/increased affinity of ligand binding domain to ligand vs. intramolecular peptide to maintain sensitivity of the sensor.

Transmembrane domain: the transmembrane domain can comprise any transmembrane domain that can be cleaved by the intramembrane protease, gamma secretase (γ-secretase). There are many naturally occurring transmembrane domains that are known to be cleaved by γ-secretase, but these domains could also be engineered as well. Exemplary γ-secretase transmembrane domains include the transmembrane domains of CD43 (GMLPVAVLVAL-LAVIVLVALLLL; SEQ ID NO: 50), CD44 (LIILASLLA-LALILAVCIAV; SEQ ID NO: 51), Klotho (LLAFIAFLFFASIISLSLIFY; SEQ ID NO: 52) and VE-Cadheren (AVVAILLCILTITVITLLIFL; SEQ ID NO: 53). Additional transmembrane domains having a g-secretase cleavage site are known in the art and can be found, for example, in Haapasolo, A et al. (2011) *J Alzheimer Dis* 25(1):3-28. In some embodiments, transmembrane domains having a low ability to oligomerize are selected for use with the sensors described herein. The ability to oligomerize can be determined using computational tools such as PREDDI-MER available on the world wide web at preddimer.nmr.ru/ manual.

Intracellular effector domain: the intracellular effector domain can comprise any chimeric protein, chimeric protein domain, or peptide that results in differential activity upon transmembrane proteolytic cleavage. Exemplary intracellular effector domains include, but are not limited to, transcription factors, fluorescent protein or protein markers, enzymes or enzyme subdomains, and peptides.

Each of these domains is discussed in further detail below.

Extracellular Ligand-Binding Domains and Ligands

The engineered receptors or sensors described herein comprise an extracellular ligand-binding domain having at least one binding site for a given ligand to bind (e.g., at least 2, 3, or 4 binding sites for the same or different ligands). In addition, the engineered receptors described herein utilize a closed confirmation induced by binding of the ligand binding site to an intramolecular peptide that is within or at the end of the flexible linker that also binds the transmembrane domain (see e.g., FIG. 1 for a schematic depiction of the engineered receptors described herein). Displacement of the intramolecular peptide is required to release the closed conformation of the receptor such that the γ-secretase cleavage site is sterically available to the γ-secretase enzyme. Thus, any ligand-binding domain can be used provided that a cognate ligand exists or can be designed to displace an intramolecular peptide as described herein. That is, the cognate ligand comprises sufficient affinity as compared to the intramolecular peptide that the ligand can displace the intramolecular peptide to activate the engineered receptor.

In one embodiment, the extracellular ligand binding domain does not comprise a Notch regulatory region (NRR). In another embodiment, the extracellular ligand binding domain is insensitive to force or stretch of the cell membrane in which the engineered receptor is expressed.

Extracellular ligand binding domains can, for example, be derived from either an existing receptor ligand-binding domain or from an engineered ligand binding domain. Existing ligand-binding domains include, but are not limited to, cytokine receptors, chemokine receptors, innate immune receptors (TLRs, etc.), olfactory receptors, steroid and hormone receptors, growth factor receptors, mutant receptors that occur in cancer, or neurotransmitter receptors. Engineered ligand-binding domains can be, for example, single-chain antibodies, engineered fibronectin-based binding proteins, antigen binding fragments (Fabs), single chain variable fragments (scFvs) and engineered consensus-derived binding proteins (e.g., based upon leucine-rich repeats or ankyrin-rich repeats, such as DARPins). Exemplary receptors include, but are not limited to, a growth factor receptor (e.g., a VEGF receptor); a killer cell lectin-like receptor subfamily K, member 1 (NKG2D) polypeptide (receptor for MICA, MICB, and ULB6); a cytokine receptor (e.g., an IL-13 receptor; an TL-2 receptor; etc.); an epidermal growth factor (EGF) receptor; Her2; CD27; a natural cytotoxicity receptor (NCR) (e.g., NKP30 (NCR3/CD337) polypeptide (receptor for HLA-B-associated transcript 3 (BAT3) and B7-H6); etc.); a T cell antigen receptor; a dihydrofolate receptor; a chimeric cytokine receptor; an Fc receptor; an extracellular matrix receptor (e.g. an integrin); a cell adhesion receptor (e.g. a cadherin); an immunoregulatory receptor including both positive co-receptors (e.g. CD28) and negative (immunosuppressive) co-receptors (e.g., PD1); a cytokine receptor; and a receptor for a immunoregulatory molecule (e.g. TGFβ), etc. In some cases, the receptor is truncated, relative to the wild-type receptor.

The cognate ligand can be a soluble ligand, or can be present on the surface of a cell. Alternatively, the ligand can be immobilized on an insoluble support, scaffold, matrix or present in a cellular microenvironment (e.g., a tumor microenvironment or extracellular matrix). The ligand can be, for example, a small molecule, a chemokine, a cytokine, a hormone, an antibody or antigen-binding fragment thereof, a peptide, a polypeptide, a neurotransmitter, a cell surface protein, an extracellular matrix component, nucleic acids, glycoproteins, small molecules, carbohydrates, lipids, glycolipids, lipoproteins, lipopolysaccharides and the like. The ligand can be present on the surface of a second cell, can be immobilized on an insoluble substrate, can be present in an extracellular matrix, can be present in an artificial matrix, or can be soluble.

In some embodiments, the extracellular ligand binding domain comprises an antigen-antibody specific binding pair, for example, the extracellular ligand binding domain can comprise an antibody (or antigen binding fragment thereof) that binds specifically to an antigen, or vice versa. The antigen can be any antigen, e.g., a naturally-occurring (endogenous) antigen or a synthetic or modified antigen; etc. In some cases, the antigen is a disease-associated antigen, e.g., a cancer-associated antigen, an autoimmune disease-associated antigen, a pathogen-associated antigen, an inflammation-associated antigen, or the like.

Where the ligand binding domain comprises an antibody specific for a cancer-associated antigen, the antigen can be a cancer-associated antigen such as e.g., CD19, CD20, CD38, CD30, Her2/neu, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (IMW-MAA), MAGE-A1, IL-13R-a2, GD2, and the like. Cancer-associated antigens also include, e.g., 4-1BB, 5T4, adenocarcinoma antigen, alpha-fetoprotein, BAFF, B-lymphoma cell, C242 antigen, CA-125, carbonic anhydrase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGI, L1-CAM, IL-13, IL-6, insulin-like growth factor I receptor, integrin α5β1, integrin αvβ, MORAb-009, MS4A1, MUC1, mucin CanAg, N-glycolylneuraminic acid, NPC-1C, PDGF-R α, PDL192, phosphatidylserine, prostatic carcinoma cells, RANKL, RON, ROR1, SCH 900105, SDC1, SLAMF7, TAG-72, tenascin C, TGF beta 2, TGF-β, TRAIL-R1, TRAIL-R2, tumor antigen CTAA16.88, VEGF-A, VEGFR-1, VEGFR2, or vimentin.

The antigen can be associated with an inflammatory disease. Non-limiting examples of antigens associated with inflammatory disease include, e.g., AOC3 (VAP-1), CAM-3001, CCL11 (eotaxin-1), CD125, CD147 (basigin), CD154 (CD40L), CD2, CD20, CD23 (IgE receptor), CD25 (α chain of IL-2 receptor), CD3, CD4, CD5, IFN-α, IFN-γ, IgE, IgE Fc region, IL-1, IL-12, IL-23, IL-13, IL-17, IL-17A, IL-22, IL-4, IL-5, IL-5, IL-6, IL-6 receptor, integrin α4, integrin α4β7, LFA-1 (CD11a), myostatin, OX-40, scleroscin, SOST, TGF beta 1, TNF-α, and VEGF-A.

Flexible Linkers

The engineered receptor polypeptide constructs described herein can comprise an optional flexible linker that links the extracellular binding domain to the transmembrane domain. In some embodiments, the extracellular ligand binding domain comprises a naturally occurring or "built-in" flexible or hinge-like linker domain at the C-terminus, thus the engineered receptor does not comprise a flexible linker. That is, the flexible linker is optional.

Where a flexible linker is used, the flexible linker can further comprise an intramolecular peptide attached at the opposite end or within the flexible linker. Such flexible linkers are designed with a good degree of freedom that allows the extracellular ligand binding domain to bend back to interact with the intramolecular peptide but are also of sufficient length to allow the extracellular binding domain to swing a distance that is far enough to remove any steric hindrance of the extracellular ligand binding domain to the γ-secretase cleavage site. In embodiments where a flexible linker is not used, the extracellular ligand binding domain comprises the intramolecular peptide to permit steric control of the sensor.

The linkers can comprise, without limitation, leucine zipper, SH2 domains, PDZ domains, antibody domains, and the like. Any other flexible linker could be used as well. In one embodiment, the flexible linker is least 2, at least 3, at least 4, or at least 5 amino acids in length. In another embodiment the flexible linker is at least 6 or at least 7 amino acids in length. In another embodiment the flexible linker is at least 8, 9, 10, 11 or 12 amino acids in length. In other embodiments, the flexible linker is between 2 to 300 amino acids in length, inclusive. For example, the flexible linker can be 2 to 250, 2 to 200, 2 to 175, 2 to 150, 2 to 100, 2 to 75, 2 to 50, 2 to 40, 2 to 30, 2 to 25, 2 to 20, 2 to 15, 2 to 10, 2 to 5, 275 to 300, 250 to 300, 225 to 300, 200 to 300, 175 to 300, 150 to 300, 125 to 300, 100 to 300, 75 to 300, 50 to 300, 25 to 300, 10 to 50, 25 to 50, 25 to 75, 50 to 100, 50 to 200, 75 to 100, 75 to 200, 75 to 300, 100 to 200, or any range therebetween. In one embodiment, the flexible linker length is determined based on one or more theoretical models of flexible linkers and their effect on local concentration as discussed in Valen et al., 2009. *Biophysical Journal* 96(4): 1275-1292.

Intramolecular Peptides

The intramolecular peptide is designed to have a lower, equal to or higher binding affinity to the ligand binding site as compared to the cognate ligand to which the engineered receptor senses and responds. The binding affinity of the intramolecular peptide will alter the sensitivity of the engineered receptor. In some embodiments, the intramolecular peptide comprises a lower affinity compared to the cognate ligand to ensure maximum sensitivity such that the intramolecular peptide can be displaced from the ligand binding site by the cognate ligand. The intramolecular peptide can be designed using techniques such as phage display, directed evolution, or rational design. Competitive binding of peptides to ligand binding sites and their manipulation thereof is well understood by those of skill in the art and are therefore not described in detail herein.

The binding affinity of the ligand can be further influenced and adjusted by adjusting suitable conditions in a solution, such as, e.g., the pH value, the concentration of ligand, and/or the selection and concentration of suitable buffer salts.

Transmembrane Domain

The engineered receptors described herein comprise a transmembrane domain that tethers the engineered receptor construct in the cell membrane and can be cleaved by a membrane protease, such as γ-secretase. The transmembrane domain can comprise any receptor transmembrane domain (e.g., G-protein coupled receptor (GPCR) domain) that comprises a γ-secretase cleavage site (e.g., a Notch transmembrane domain). In some embodiments, the transmembrane domain is that of a monomeric receptor (e.g., not a tyrosine kinase domain). The engineered receptors described herein rely on processing by γ-secretase, which naturally cleaves and processes type 1 integral membrane proteins, such as Notch, ErbB4, E-cadherin, N-cadherin, ephrin-B2, and CD44. Thus, transmembrane domains derived from Notch, ErbB4, E-cadherin, N-cadherin, ephrin-B2 and Cd44 are specifically contemplated for use with the methods and compositions described herein.

In some embodiments, the transmembrane domain comprises a single γ-secretase cleavage site. In other embodiments, the transmembrane domain comprises 2, 3 or 4 γ-secretase cleavage sites. A γ-secretase cleavage site can comprise a Gly-Val dipeptide sequence, where the enzyme cleaves between the Gly and the Val. For example, in some cases, an S3 ligand-inducible proteolytic cleavage site has the amino acid sequence VGCGVLLS (SEQ ID NO: 1), where cleavage occurs between the "GV" sequence. In some cases, an S3 ligand-inducible proteolytic cleavage site comprises the amino acid sequence GCGVLLS (SEQ ID NO: 2).

In some embodiments, the engineered receptors described herein comprise a transmembrane domain from the Notch receptor and comprises an amino acid sequence that is at least 75%, at least 80%, at least 85%, at least 90%, at least 95%, at least 98%, at least 99%, or 100%, amino acid sequence identity to the following amino acid sequence: HLMYVAAAAFVLLFFVGCGVLL (SEQ ID NO: 3). In such embodiments, the engineered receptor comprises at least one γ-secretase cleavage domain (e.g., at least 2, at least 3 or at least 4 γ-secretase cleavage domains).

In other embodiments, In some cases, the engineered receptors described herein comprise a Notch receptor polypeptide comprising a transmembrane domain and having an amino acid sequence with at least 75%, at least 80%, at least 85%, at least 90%, at least 95%, at least 98%, at least 99%, or 100%, amino acid sequence identity to the following amino acid sequence: IPYKIEAVKSEPVEPPLP-SQLHLMYVAAAAFVLLFFVGCGVLLSRKRRRQLCI-QKL (SEQ ID NO: 4); where the TM domain is underlined; wherein the Notch receptor polypeptide has a length of from 50 amino acids (aa) to 65 aa, e.g., 50, 51, 52, 53, 54, 55, 56, 57, 58, 59, 60, 61, 62, 63, 64, or 65 aa.

In some embodiments, the transmembrane domain or other domains of the engineered receptor polypeptide construct can comprise one or more non-gamma-secretase cleavage sites such as e.g., a metalloproteinase cleavage site, e.g., a cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). For example, the cleavage sequence of MMP-9 is Pro-X-X-Hy (wherein, X represents an arbitrary residue; Hy, a hydrophobic residue), e.g., Pro-X-X-Hy-(Ser/Thr), e.g., Pro-Leu/Gln-Gly-Met-Thr-Ser (SEQ ID NO: 5) or Pro-Leu/Gln-Gly-Met-Thr (SEQ ID NO: 6).

In one embodiment, the transmembrane domain comprises the sequence:

(SEQ ID NO: 49)
PVEPPLPSQLHLMYVAAAAFVLLFFVGCGVLLSRKRRR.

Intracellular Effector Domains

The engineered receptors described herein comprise an intracellular effector domain, which is an effector molecule that is released following cleavage by γ-secretase. Ligand binding to the at least one ligand binding site within the extracellular ligand binding domain opens a conformation of the engineered receptor that permits cleavage by γ-secretase and release of the intracellular domain. The intracellular domain, when released from the engineered receptor, provides an effector function such as e.g., altered transcription of a gene product; expression of a fluorescent protein or other cellular marker; increased production of one or more cytokines by the cell; reduced production of one or more cytokines by the cell; increased or decreased production of a hormone by the cell; production of an antibody by the cell; a change in organelle activity; a change in trafficking of a polypeptide within the cell; a change in transcription of a target gene; a change in activity of a protein; a change in cell behavior, e.g., cell death; cellular proliferation; effects on cellular differentiation; effects on cell survival; modulation of cellular signaling responses; etc. In some cases, the released intracellular domain provides for a change in transcription of a target gene (e.g., an increase or decrease in transcription of the target gene; modulation of expression of an endogenous or heterologous gene).

The intracellular domain can be any of a wide variety of polypeptides or nucleic acids, where examples include, but are not limited to, transcriptional activators; transcriptional repressors; transcriptional co-activators; transcriptional co-repressors; DNA binding polypeptides; RNA binding polypeptides; microRNAs; RNA interference molecules (e.g., shRNA, siRNA, dsRNA and the like); translational regulatory polypeptides; hormones; cytokines; toxins; antibodies; chromatin modulators; cytotoxic or suicide proteins; organelle specific polypeptides (e.g., a nuclear pore regulator, a mitochondrial regulator, an endoplasmic reticulum regulator, and the like); pro-apoptosis polypeptides; anti-apoptosis polypeptides; other polypeptides that promote cell death through other mechanisms; pro-proliferation polypeptides; anti-proliferative polypeptides; immune co-stimulatory polypeptides; site-specific nucleases; recombinases; inhibitory immunoreceptors; an activating immunoreceptor; Cas9 and variants of RNA targeted nucleases; and DNA recognition polypeptides; dominant negative variants of a polypeptide; a signaling polypeptide; a polypeptide that promotes differentiation; a split-enzyme and the like.

In some cases, the intracellular effector domain comprises a signaling polypeptide. Suitable signaling polypeptides include, e.g., STAT3/5, Akt, Myc, and the like. In some cases, the signaling polypeptide is a part of a PI3K/mTOR-, NFκB-, MAPK-, STAT-, FAK-, MYC-, or TGF-β mediated signaling pathway. In some cases, the signaling polypeptide is a part of a Ras/Raf/Mek/Erk1/2, a JAK/STAT3, or a PI3K/Akt signaling pathway.

In some cases, the intracellular effector domain comprises a dominant negative variant of a polypeptide to inhibit action of a given endogenous polypeptide, e.g., a dominant negative variant of a signaling polypeptide. Examples of dominant negative variants include, e.g., a dominant negative TGF-β receptor; a dominant negative variant of STAT3 comprising one or more mutations affecting the DNA binding domain of STAT3 that functions as a dominant negative variant; and the like.

In some cases, the intracellular domain is a recombinase, such as a Cre recombinase; a Flp recombinase; a Dre recombinase; and the like. A suitable recombinase is a FLPe recombinase (see, e.g., Akbudak and Srivastava (2011) Mol. Biotechnol. 49:82). A suitable recombinase is a Flpo recombinase. A recombinase, as described herein, can be an intact recombinase or a split recombinase. Portions of a split recombinase can be expressed from the same or different expression constructs. In some instances, two parts of a split recombinase can be operably linked to different engineered receptors or other trigger switches. In other instances, a first part of a split recombinase can be operably linked to an engineered receptor as described herein and the second part of the split recombinase can be separately expressed from an expression construct.

Where split recombinases are utilized, the portions of the split recombinase may be arranged in and expressed from one or more expression cassettes with other components in various ways essentially as described below regarding split transcription factors.

Accordingly, activation of one or more engineered receptors can induce expression of portions of split recombinases resulting in heterodimerization and/or complex formation of the split recombinase portions resulting in formation of a functional recombinase. Alternatively, activation of one or more engineered receptors can result in release of recombinase portions from the one or more engineered receptors resulting in heterodimerization and/or complex formation of the split recombinase portions resulting in formation of a functional recombinase. In addition, induction and release of split recombinase portions can be combined, e.g., where activation of one or more engineered receptors can induce expression of portions of split recombinases and release of split recombinase portions from the one or more engineered receptor resulting in heterodimerization and/or complex formation of the split recombinase portions resulting in formation of a functional recombinase.

Suitable split recombinases that can be used with the engineered receptors described herein include, but are not limited to, e.g., split Cre recombinase as described in e.g., Beckervordersandforth R et al., Stem Cell Reports. 2014; 2(2):153-62Wen M et al., PLoS One. 2014; 9(10):e110290 O'Brien S P et al., Biotechnol J. 2014; 9(3):355-61Wang P et al., Sci Rep. 2012; 2:497 Hirrlinger J et al., PLoS One. 2009; 4(12):e8354 Hirrlinger J et al., PLoS One. 2009; 4(1):e4286; the disclosures of which are incorporated herein by reference in their entirety.

A suitable Cre recombinase can comprise an amino acid sequence having at least about 75%, at least about 80%, at least about 85%, at least about 90%, at least about 95%, at least about 98%, or 100%, amino acid sequence identity to the following amino acid sequence: VSNLLTVHQNL-PALPVDATS-
DEVRKNLMDMFRDRQAFSEHTWKMLLSVCR-SWAAWC
KLNNRKWFPAEPEDVRDYLLYLQARGLAVK-TIQQHLGQLNMLHRRSGLPRPSDSNAVS LVMR-RIRKENVDAGERAKQALAFERTDFDQVRSL- MENSDRCQDIRNLAFLGIAYNTLLR
IAEIARIRVKDISRTDGGRMLIHI-
GRTKTLVSTAGVEKALSLGVTKLVERWISVSGVADDP
NNYLFCRVRKNGVAAPSATSQLSTRALEGIFEATH-
RLIYGAKDDSGQRYLAWSGHSAR VGAARD-
MARAGVSIPEIMQAGGWTNVNIVMNYIRNLDSET-
GAMVRLLEDGD (SEQ ID NO: 7); and can have a length
of from 335 amino acids (aa) to 350 aa.

A suitable FLPe recombinase can comprise an amino acid sequence having at least about 75%, at least about 80%, at least about 85%, at least about 90%, at least about 95%, at least about 98%, or 100%, amino acid sequence identity to the following amino acid sequence: MSQFDILCK-
TPPKVLVRQFVERFERPSGEKIASCAAELTYL-
CWMITHNGTAIKRATFMSY NTIISNSLSFDI-
VNKSLQFKYKTQKATILEASLKKLIPAWEFTIIPYNG-
QKHQSDITDIVSSL QLQFESSEEADKGNSHSKKML-
KALLSEGESIWEITEKILNSFEYTSRFTKTKTLYQFL-
FLA TFINCGRFSDIKNVDPKSFKLVQN-
KYLGVIIQCLVTETKTSVSRHIYFFSARGRIDPLVYL
DEFLRN-
SEPVLKRVNRTGNSSSNKQEYQLLKDNLVRSYNKA-
LKKNAPYPIFAIKNGPKS
HIGRHLMTSFLSMKGLTELTNVVGNWSDKRASA-
VARTTYTHQITAIPDHYFALVSRYY AYDPISKEMI-
ALKDETNPIEEWQHIEQLKGSAEGSIRYPAWNGI-
ISQEVLDYLSSYINRRIG PVEQKLISEEDL (SEQ ID NO: 8); and can have a length of from 430 amino acids to 445 amino acids.

Suitable site-specific nucleases include, but are not limited to, an RNA-guided DNA binding protein having nuclease activity, e.g., a Cas9 polypeptide; a transcription activator-like effector nuclease (TALEN); Zinc-finger nucleases; and the like.

Exemplary Cas9 polypeptides are known in the art; see, e.g., Fonfara et al. (2014) Nucl. Acids Res. 42:2577; and Sander and Joung (2014) Nat. Biotechnol. 32:347. A Cas9 polypeptide can comprise an amino acid sequence having at least about 75%, at least about 80%, at least about 85%, at least about 90%, at least about 95%, at least about 98%, or 100%, amino acid sequence identity to the amino acid sequence of Met Lys Trp Lys Ala Leu Phe Thr Ala Ala Ile Leu Gln Ala Gln Leu Pro Ile Thr Glu Ala Gln Ser Phe Gly Leu Leu Asp Pro Lys Leu Cys Tyr Leu Leu Asp Gly Ile Leu Phe Ile Tyr Gly Val Ile Leu Thr Ala Leu Phe Leu Arg Val Lys Phe Ser Arg Ser Ala Asp Ala Pro Ala Tyr Gln Gln Gly Gln Asn Gln Leu Tyr Asn Glu Leu Asn Leu Gly Arg Arg Glu Glu Tyr Asp Val Leu Asp Lys Arg Arg Gly Arg Asp Pro Glu Met Gly Gly Lys Pro Arg Arg Lys Asn Pro Gln Glu Gly Leu Tyr Asn Glu Leu Gln Lys Asp Lys Met Ala Glu Ala Tyr Ser Glu Ile Gly Met Lys Gly Glu Arg Arg Arg Gly Lys Gly His Asp Gly Leu Tyr Gln Gly Leu Ser Thr Ala Thr Lys Asp Thr Tyr Asp Ala Leu His Met Gln Ala Leu Pro Pro Arg (SEQ ID NO: 9).

In some cases, the intracellular domain is a Cas9 variant that lacks nuclease activity, but retains DNA target-binding activity. Such a Cas9 variant is referred to herein as a "dead Cas9" or "dCas9." See, e.g., Qi et al. (2013) Cell 152:1173. A dCas9 polypeptide can comprise a D10A and/or an H840A amino acid substitution of the amino acid sequence set forth in SEQ ID NO: 9 or corresponding amino acids in another Cas9 polypeptide.

In some cases, the intracellular domain is a chimeric dCas9, e.g., a fusion protein comprising dCas9 and a fusion partner, where suitable fusion partners include, e.g., a non-Cas9 enzyme that provides for an enzymatic activity, where the enzymatic activity is methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity. In some cases, the intracellular domain is a chimeric dCas9, e.g., a fusion protein comprising dCas9 and a fusion partner, where suitable fusion partners include, e.g., a non-Cas9 enzyme that provides for an enzymatic activity, where the enzymatic activity is nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity.

In some cases, the intracellular domain is a chimeric dCas9, e.g., a fusion protein comprising dCas9 and a fusion partner, where suitable fusion partners include, e.g., transcription activator or a transcription repressor domain (e.g., the Kruppel associated box (KRAB or SKD); the Mad mSIN3 interaction domain (SID); the ERF repressor domain (ERD), etc.); zinc-finger-based artificial transcription factors (see, e.g., Sera (2009) Adv. Drug Deliv. 61:513); TALE-based artificial transcription factors (see, e.g., Liu et al. (2013) Nat. Rev. Genetics 14:781); and the like.

In some cases, the intracellular domain is an apoptosis inducer. A suitable apoptosis inducer includes tBID. The term "tBID" refers to the C-terminal truncated fragment of the BH3 interacting death agonist (BID) protein which results from the enzymatic cleavage of cytosolic BID (e.g., by active caspase). At an early stage of apoptosis, tBID translocates to the mitochondria and mediates the release of cytochrome c therefrom. Non-limiting examples of tBID proteins include human tBID (amino acids 61-195 of the amino acid sequence provided in GenBank Accession No. CAG30275).

Human tBID has the following amino acid sequence: gnrsshsrlgrieadsesgediirniarhlagvgdsmdrsippglvnglae-
drnrdlataleqllqayprdmekektmlvlalllakkvas htpsllrdvfhttvnf-
ingnlrtyvrslarngmd (SEQ ID NO: 10).

In some embodiments, the intracellular domain comprises an amino acid sequence having at least 75%, at least 80%, at least 85%, at least 90%, at least 95%, at least 98%, at least 99%, or 100%, amino acid sequence identity to the human tBID amino acid sequence provided above; and has a length of from about 120 amino acids (aa) to 150 aa, e.g., from 120 aa to 125 aa, from 125 aa to 130 aa, from 130 aa to 135 aa, from 135 aa to 140 aa, from 140 aa to 145 aa, or from 145 aa to 150 aa. In some cases, the intracellular domain comprises an amino acid sequence having at least 75%, at least 80%, at least 85%, at least 90%, at least 95%, at least 98%, at least 99%, or 100%, amino acid sequence identity to the human tBID amino acid sequence provided above; and has a length of 135 aa.

In some cases, the intracellular domain is a transcription factor. Examples of suitable transcription factors are those presented in Table 1 of U.S. Patent Application No. 2014/0308746, the contents of which are incorporated herein by reference in their entirety. In some cases, the intracellular domain is a transcriptional regulator. Non-limiting examples of suitable transcriptional regulators include, but are not limited to e.g., ABT1, ACYP2, AEBP1, AEBP2, AES, AFF1, AFF3, AHR, ANK1, ANK2, ANKFY1, ANKIB1, ANKRD1, ANKRD10, ANKRD2, ANKRD32, ANKRD46, ANKRD49, ANKRD56, ANKRD57, ANKS4B, AR, ARHGAP17, ARID1A, ARID1B, ARID3A, ARID4A, ARID5B, ARNT, ARNT2, ARNTL, ARNTL2, ARX, ASB10, ASB11, ASB12, ASB15, ASB2, ASB5, ASB8, ASB9, ASH1L, ASH2L, ASXL1, ASZ1, ATF1, ATF3, ATF4, ATF4, ATF5, ATF6, ATF7, ATF7IP, ATM, ATOH1, ATXN3, 1300003B13RIK, B3GAT3, B930041F14RIK, BACH1, BACH2, BARX1, BARX2, BATF, BATF2, BATF3, BAZ2A, BBX, BC003267, BCL11A, BCL11B, BCL3, BCL6, BCL6B, BCLAF1, BCOR, BHLHA15, BHLHE40, BHLHE41, BLZF1, BMYC, BNC1, BNC2, BPNT1, BRCA1, BRWD1, BTBD11, BTF3, 6030408C04RIK, CAMK4, CARHSP1, CARM1, CBX4, CBX7, CCNC, CCNH, CCNT1, CCNT2, CDC5L, CDK2, CDK4, CDK9, CDKN2C, CDX1, CDX1, CDX2, CEBPA, CEBPB, CEBPD, CEBPG, CEBPG, CEBPZ, CHD4, CHD7, CHGB, CIC, CIITA, CITED1, CITED2, CITED4, CLOCK, CLPB, CML3, CNOT7, COPS2, CREB1, CREB3, CREB3L1, CREB3L1, CREB3L2, CREB3L3, CREB5, CREBBP, CREBL2, CREM, CSDA, CSDA, CSDC2, CSDE1, CTBP2, CTCF, CTCFL, CTNNB1, CTNNBL1, CXXC1, D11BWG0517E, 2300002D11RIK, DACH1, DAXX, DBP, DDIT3, DDX20, DDX54, DDX58, DEAF1, DEK, DIDO1, DLX2, DMRT1, DMRT2, DMRTB1, DNMT1, DNMT3A, DR1, DRG1, DUSP26, DYSFIP1, E2F1, E2F2, E2F3, E2F5, E2F6, EBF1, EBF2, EBF3, EBF3, EED, EGR1, EGR2, EGR3, EHF, EHMT2, EID2, ELAVL2, ELF1, ELF1, ELF2, ELF3, ELF4, ELF5, ELK3, ELK4, ELL2, EMX2, EMX2, EN2, ENPP2, EOMES, EP300, EPAS1, ERF, ERG, ESR1, ESRRA, ESRRB, ESRRG, ETS1, ETS2, ETV1, ETV3, ETV4, ETV5, ETV6, EVI1, EWSR1, EZH1, EZH2, FAH, FBXL10, FBXL11, FBXW7, FEM1A, FEM1B, FEM1C, FHL2, FLII, FMNL2, FOS, FOSB, FOSL1, FOSL2, FOXA1, FOXA2, FOXA3, FOXC1, FOXD1, FOXD2, FOXD3, FOXF1, FOXF1A, FOXF2, FOXG1, FOXI1, FOXJ2, FOXJ3, FOXK1, FOXK2, FOXL1, FOXL2, FOXM1, FOXN1, FOXN2, FOXN3, FOXO1, FOXO3, FOXP1, FOXP2, FOXP3, FOXP4, FOXQ1, FUS, FUSIP1, 2810021G02RIK, GABPA, GABPB1, GARNL1, GAS7, GATA1, GATA2, GATA3, GATA4, GATA5, GATA5, GATA6, GBX2, GCDH, GCM1, GFI1, GFI1B, GLI2, GLI3, GLIS1, GLIS2, GLIS3, GLS2, GMEB1, GMEB2, GRHL1, GRHL2, GRHL3, GRLF1, GTF2A1, GTF2B, GTF2E2, GTF2F1, GTF2F2, GTF2H2, GTF2H4, GTF2I, GTF2IRD1, GTF2IRD1, GZF1, HAND2, HBP1, HCLS1, HDAC10, HDAC11, HDAC2, HDAC5, HDAC9, HELZ, HES1, HES4, HES5, HES6, HEXIM1, HEY2, HEYL, HHEX, HHEX, HIC1, HIC2, HIF1A, HIF1AN, HIPK2, HIVEP1, HIVEP2, HIVEP2, HIVEP3, HLF, HLTF, HLX, HMBOX1, HMG20A, HMGA2, HMGB2, HMGB3, HNF1B, HNF4A, HNF4G, HOMEZ, HOXA10, HOXA11, HOXA13, HOXA2, HOXA3, HOXA4, HOXA5, HOXA6, HOXA7, HOXA9, HOXB1, HOXB2, HOXB3, HOXB4, HOXB6, HOXB7, HOXB8, HOXB9, HOXC10, HOXC10, HOXC11, HOXC5, HOXC6, HOXC8, HOXC9, HOXD8, HOXD9, HR, HSBP1, HSF2BP, HTATIP2, HTATSF1, HUWE1, 5830417I10RIK, ID1, ID2, ID3, ID3, IFNAR2, IKBKB, IKBKG, IKZF1, IKZF2, IKZF3, IKZF4, IL31RA, ILF3, ING1, ING2, ING3, ING4, INSM1, INTS12, IQWD1, IRF1, IRF1, IRF2, IRF3, IRF4, IRF5, IRF6, IRF7, IRF8, IRF8, IRX1, IRX2, IRX3, IRX4, IRX5, ISL1, ISL2, ISX, ISX, IVNS1ABP, 2810021J22RIK, JARID1A, JARID1B, JARID1C, JARID1D, JDP2, JUN, JUNB, JUND, KLF1, KLF10, KLF11, KLF12, KLF13, KLF15, KLF16, KLF2, KLF3, KLF3, KLF4, KLF5, KLF6, KLF7, KLF8, KLF9, KRR1, 6330416L07RIK, L3MBTL2, LASS2, LASS4, LASS6, LBA1, LBH, LBX1, LCOR, LDB1, LDB2, LEFT, LHX1, LHX2, LHX5, LIMD1, LIN28, LMO1, LMO4, LMX1A, LSM11, LSM4, LYL1, 9030612M13RIK, 1810007M14RIK, 3632451006RIK, MAF, MAFA, MAFB, MAFF, MAFG, MAFK, MAGED1, MAP3K12, MAPK1, MAPK3, MAPK8, MAPK8IP1, MAX, MAZ, MBD2, MCM2, MCM4, MCM5, MCM6, MCMI, MECOM, MECP2, MED12, MED5, MEF2A, MEF2B, MEF2C, MEF2D, MEIS1, MEIS1, MEIS2, MEOX2, MESP2, MID1, MITF, MKI67IP, MKL1, MLL1, MLL3, MLLT10, MLLT3, MLX, MLXIP, MLXIPL, MNT, MNX1, MPL, MSC, MSRB2, MSX2, MTA3, MTF1, MTF2, MTPN, MXD1, MXD4, MXI1, MYB, MYBBP1A, MYBL2, MYC, MYCBP, MYCL1, MYCN, MYEF2, MYF6, MYNN, MYOCD, MYOD1, MYOG, MYST3, MYST4, MYT 1L, MZF1, NAB1, NAB2, NANOG, NARG1, NCOA1, NCOA2, NCOA3, NCOR1, NCOR2, NDN, NEUROD1, NEUROD4, NEUROD6, NEUROG1, NEUROG2, NFAT5, NFATC1, NFATC2, NFATC2IP, NFATC3, NFATC3, NFATC4, NFE2, NFE2L1, NFE2L2, NFIA, NFIA, NFIB, NFIC, NFIL3, NFIX, NFKB1, NFKB2, NFKBIB, NFKBIE, NFKBIZ, NFX1, NFXL1, NFYA, NFYB, NHLH1, NKX2-2, NKX2-3, NKX2-5, NKX2-6, NKX6-2, NMI, NOTCH1, NOTCH2, NOTCH3, NOTCH4, NPAS1, NPAS2, NPAS3, NROB1, NROB2, NR1D1, NR1D2, NR1H3, NR1H4, NR1I2, NR1I3, NR2C1, NR2C2, NR2E3, NR2F1, NR2F2, NR2F6, NR3C1, NR3C2, NR4A1, NR4A2, NR4A2, NR4A3, NR5A1, NR5A2, NRARP, NRIP1, NRIP2, NSBP1, NSD1, NUDT12, NULL, NUPR1, 1700065O13RIK, OLIG1, OLIG2, OLIG2, ONECUT1, ONECUT2, ONECUT3, ORC2L, OSGIN1, OSR1, OSR2, OSTF1, OVOL1, OVOL2, PAPOLA, PAPOLG, PAPPA2, PATZ1, PAWR, PAX2, PAX5, PAX6, PAX7, PAX8, PAX9, PBX1, PBX2, PBX3, PBX4, PCBD1, PCGF6, PDCD11, PDLIM4, PDX1, PEG3, PER1, PFDN1, PGR, PHF1, PHF10, PHF12, PHF13, PHF14, PHF20, PHF21A, PHF5A, PHF7, PHOX2A, PHOX2B, PIAS2, PIR, PITX1, PITX2, PKNOX1, PKNOX2, PLA2G6, PLAGL1, PLAGL2, PLRG1, PML, POGK, POLR2B, POLR2E, POLR2H, POLR3E, POLR3H, POLRMT, POU1F1, POU2AF1, POU2F1, POU2F2, POU3F2, POU3F3, POU3F3, POU5F1, POU6F1, PPARA, PPARD, PPARG, PPARGC1A, PPARGC1B, PPP1R12C, PPP1R13B, PPP1R16B, PPP1R1B, PPP2R1A, PPP3CB, PQBP1, PRDM1, PRDM14, PRDM15, PRDM16, PRDM2, PRDM4, PRDM5, PRDM6, PRDM8, PREB, PRKAR1A, PRKCBP1, PROX1, PRRX1, PRRX2, PSMC5, PSMD10, PSMD9, PTF1A, PTGES2, PURB, PWP1, RAB11A, RAB11B, RAB15, RAB18, RAB1B, RAB25, RAB8A, RAB8B, RAI14, RARA, RARB, RARG, RASSF7, RB1, RBBP7, RBL1, RBM14, RBM39, RBM9, RBPJ, RBPJL, RCOR2, REL, RELA, RELB, RERE, REST, REXO4, RFC1, RFX1, RFX2, RFX3, RFX5, RFX7, RFX8, RHOX5, RHOX6, RHOX9, RIPK4, RNF12, RNF14, RNF141, RNF38, RNF4, RORA, RORA, RORB, RORC, RPS6KA4, RREB1, RSRC1, RUNX1, RUNX1T1, RUNX2, RUNX2, RUNX3, RUVBL1, RUVBL2, RXRA, RXRG, RYBP, SAFB2, SALL1, SALL1, SALL2, SALL4, SAP30, SAP30BP, SATB1, SATB2, SATB2, SCAND1, SCAP, SCRT2, SEC14L2, SERTAD1, SF1, SFPI1, SFRS5, SH3D19, SH3PXD2B, SHANK3, SHOX2, SHPRH, SIN3A, SIN3B, SIRT2, SIRT3, SIRT5, SIX1, SIX1, SIX2, SIX3, SIX4, SIX5, SKI, SMAD1, SMAD2, SMAD3, SMAD7, SMARCA1, SMARCA2, SMARCA5, SMARCB1, SMYD1, SNAI1, SNAI2, SNAPC2, SNAPC4, SNIP1, SOLH, SOX1, SOX10, SOX11, SOX12, SOX13, SOX15, SOX17, SOX18, SOX2, SOX21, SOX4, SOX5, SOX6, SOX7, SOX8, SOX9, SP1, SP110, SP140L, SP2, SP3, SP4, SP6, SP8, SPDEF, SPEN, SPIl, SPIB, SQSTM1, SREBF1, SREBF2, SREBF2, SRF, SSBP2, SSBP3, SSBP4, SSRP1, ST18, STAG1, STAT1, STAT1, STAT2, STAT3, STAT4, STAT5A, STAT5B, STAT5B, STATE, SUB1, SUZ12, TADA2L, TAF13, TAF5, TAF5L, TAF7, TAF9, TALI, TALI, TARDBP, TBPL1, TBR1, TBX1, TBX10, TBX15, TBX18, TBX2, TBX2, TBX20, TBX21, TBX3, TBX4, TBX5, TBX6, TCEA1, TCEA3, TCEAL1, TCEB3, TCERG1, TCF12, TCF15, TCF19, TCF20, TCF21, TCF21, TCF3, TCF4, TCF7, TCF7L2, TCFAP2A, TCFAP2B, TCFAP2C, TCFCP2L1, TCFE2A, TCFE3, TCFEB, TCFEC, TCFL5, TEAD1, TEAD2, TEAD3, TEAD4, TEF, TFAP2A, TFAP2C, TFCP2L1, TFDP2, TFEB, TFEC, TGFB1I1, TGIF1, TGIF2, TGIF2LX, THRA, THRAP3, THRB, THRSP, TIAL1, TLE1, TLE6, TMEM131, TMPO, TNFAIP3, TOB1, TOX4, TP63, TRERFI, TRIB3, TRIM24, TRIM28, TRIM30, TRIP13, TRIP4, TRIP6, TRP53, TRP53BP1, TRP63, TRPS1, TRPS1, TSC22D1, TSC22D2, TSC22D3, TSC22D4, TSHZ1, TSHZ1, TSHZ3, TTRAP, TUB, TULP4, TWISTI, TWIST2, TYSND1, UBE2W, UBN1, UBP1, UBTF, UGP2, UHRF1, UHRF2, UNCX, USF1, USF2, UTF1, VDR, VEZF1, VGLL2, VSX1, WASL, WHSC1, WHSC2, WT1, WWP1, WWTR1, XBP1, YAF2, YY1, ZBED1, ZBED4, ZBTB1, ZBTB10, ZBTB16, ZBTB16, ZBTB17, ZBTB2, ZBTB20, ZBTB22, ZBTB25, ZBTB32, ZBTB38, ZBTB4, ZBTB43, ZBTB45, ZBTB47, ZBTB7A, ZBTB7B, ZBTB7C, ZCCHC8, ZDHHC13, ZDHHC16, ZDHHC21, ZDHHC5, ZDHHC6, ZEB2, ANK2ZEB2, ZFHX2, ZFHX3, ZFHX4, ZFP105, ZFP110, ZFP143, ZFP148, ZFP161, ZFP192, ZFP207, ZFP219, ZFP238, ZFP263, ZFP275, ZFP277, ZFP281, ZFP287, ZFP292, ZFP35, ZFP354C, ZFP36, ZFP36L1, ZFP386, ZFP407, ZFP42, ZFP423, ZFP426, ZFP445, ZFP451, ATF5ZFP451, ZFP467, ZFP52, ZFP57, ZFP592, ZFP593, ZFP597, ZFP612, ZFP637, ZFP64, ZFP647, ZFP748, ZFP810, ZFP9, ZFP91, ZFPM1, ZFPM2, ZFX, ZHX2, ZHX3, ZIC1, ZIC2, ZIC3, ZIC4, ZIC5, ZKSCAN1, ZKSCAN3, ZMYND 11, ZNF143, ZNF160, ZNF175, ZNF184, ZNF192, ZNF213, ZNF217, ZNF219, ZNF22, ZNF238, ZNF24, ZNF267, ZNF273, ZNF276, ZNF280D, ZNF281, ZNF292, ZNF311, ZNF331, ZNF335, ZNF337, ZNF33B, ZNF366, ZNF394, ZNF398, ZNF41, ZNF410, ZNF415, ZNF423, ZNF436, ZNF444, ZNF445, ZNF451, ZNF460, ZNF496, ZNF498, ZNF516, ZNF521, ZNF532, ZNF536, ZNF546, ZNF552, ZNF563, ZNF576, ZNF580, ZNF596, ZNF621, ZNF628, ZNF648, ZNF649, ZNF652, ZNF655, ZNF664, ZNF668, ZNF687, ZNF692, ZNF696, ZNF697, ZNF710, ZNF80, ZNF91, ZNF92, ZNRD1, ZSCAN10, ZSCAN16, ZSCAN20, ZSCAN21, ZXDC, and ZZZ3.

In some cases, the intracellular domain is a transcription factor. Suitable transcription factors for use as intracellular domains include, e.g., ASCL1, BRN2, CDX2, CDX4, CTNNB1, EOMES, JUN, FOS, HNF4a, HOXAs (e.g., HOXA1, HOXA2, HOXA3, HOXA4, HOXA5, HOXA10, HOXA11, HOXA13), HOXBs (e.g., HOXB9), HOXCs (e.g., HOXC4, HOXC5, HOXC6, HOXC8, HOXC9, HOXC10, HOXC11, HOXC12, HOXC13), HOXDs (e.g., HOXD1, HOXD3, HOXD4, HOXD8, HOXD9, HOXD10, HOXD 11, HOXD12, HOXD13), SNAIL-3, MYOD1, MYOG, NEUROD1-6 (e.g., NEUROD1, NEUROD2, NEUROD4, NEUROD6), PDX1, PU.1, SOX2, Nanog, Klf4, BCL-6, SOX9, STAT1-6, TBET, TCF, TEAD1-4 (e.g., TEAD1, TEAD2, TEAD3, TEAD4), TAF6L, CLOCK, CREB, GATA3, IRF7, MycC, NFkB, RORyt, RUNX1, SRF, TBX21, NFAT, MEF2D, and FoxP3.

In some cases, the intracellular domain is a transcription factor having a regulatory role in one or more immune cells (i.e., an immune cell regulatory transcription factor). Suitable immune cell regulatory transcription factors include, e.g., 2210012G02Rik, Akap81, Appl2, Arid4b, Arid5b, Ashl1, Atf7, Atm, C430014K11Rik, Chd9, Dmtf1, Fos, Foxo1, Foxp1, Hmbox1, Kdm5b, Klf2, Mga, Mll1, Mll3, Myst4, Pcgf6, Rev31, Scm14, Scp2, Smarca2, Ssbp2, Suhw4, Tcf7, Tfdp2, Tox, Zbtb20, Zbtb44, Zeb1, Zfm1, Zfp1, Zfp319, Zfp329, Zfp35, Zfp386, Zfp445, Zfp518, Zfp652, Zfp827, Zhx2, Eomes, Arnt1, Bbx, Hbp1, Jun, Mef2d, Mterfd1, Nfat5, Nfe212, Nrld2, Phf21a, Taf4b, Trf, Zbtb25, Zfp326, Zfp451, Zfp58, Zfp672, Egr2, Ikzf2, Taf1d, Chrac1, Dnajb6, Ap1p2, Batf, Bhlhe40, Fosb, Hist1h1c, Hopx, Ifih1, Ikzf3, Lass4, Lin54, Mxd1, Mxi1, Prdm1, Prf1, Rora, Rpa2, Sap30, Stat2, Stat3, Taf9b, Tbx21, Trps1, Xbp1, Zeb2, Atf3, Cenpe1, Lass6, Rb1, Zbtb41, Crem, Fos12, Gtf2b, Irf7, Maff, Nr4a1, Nr4a2, Nr4a3, Obfc2a, Rbl2, Re1, Rybp, Sra1, Tgif1, Tnfaip3, Uhrf2, Zbtb1, Ccdc124, Csda, E2f3, Epas1, H1f0, H2afz, Hif1a, Ikzf5, Irf4, Nsbp1, Pim1, Rfc2, Swap70, Tfb1m, 2610036L11Rik, 5133400G04Rik, Apitd1, Blm, Brca1, Brip1, C1d, C79407, Cenpa, Cfl1, Clspn, Ddx1, Dscc1, E2f7, E2f8, Ercc61, Ezh2, Fen1, Foxm1, Gen1, Gsg2, H2afx, Hdac1, Hdgf, Hells, Hist1h1e, Hist3h2a, Hjurp, Hmgb2, Hmgb3, Irf1, Irf8, Kif22, Kif4, Lig1, Lmo2, Lnp, Mbd4, Mcm2, Mcm3, Mcm4, Mcm5, Mcm6, Mcm7, Myb12, Neil3, Nusap1, Orc61, Pola1, Pola2, Pole, Pole2, Polh, Polr2f, Polr2j, Ppp1r8, Prim2, Psmc3ip, Rad51, Rad51c, Rad541, Rfc3, Rfc4, Rnps1, Rpa1, Smarcc1, Spic, Ssrp1, Taf9, Tfdp1, Tmpo, Topbp1, Trdmt1, Uhrf1, Wdhd1, Whsc1, Zbp1, Zbtb32, Zfp367, Carl, Polg2, Atr, Lef1, Myc, Nucb2, Satb1, Taf1a, Ift57, Apex1, Chd7, Chtf8, Ctnnb1, Etv3, Irf9, Myb, Mybbp1a, Pms2, Preb, Sp110, Stat1, Trp53, Zfp414, App, Cdk9, Ddb1, Hsf2, Lbr, Pa2g4, Rbms1, Rfc1, Rfc5, Tada21, Tex261, Xrcc6, and the like.

In some cases, a transcription factor can be an artificial transcription factor (ATF) including but not limited to e.g., Zinc-finger-based artificial transcription factors (including e.g., those described in Sera T. Adv Drug Deliv Rev. 2009 61(7-8):513-26; Collins et al. Curr Opin Biotechnol. 2003 14(4):371-8; Onori et al. BMC Mol Biol. 2013 14:3 the disclosures of which are incorporated herein by reference in their entirety).

In some cases, the intracellular domain comprises a toxin or pro-apoptotic protein. Such intracellular domains are useful for targeted killing of cells administered as a therapy, including CAR T cells, stem cells, progenitor cells, and the like. Examples of toxins include, e.g., diphtheria toxin A fragment, nonbinding active fragments of diphtheria toxin, exotoxin A (from *Pseudomonas aeruginosa*), ricin A chain, abrin A chain, modeccin A chain, α-sacrin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogillin, restrictocin, phenomycin, and neomycin. In some cases, the intracellular domain comprises a protein that is normally secreted by a bacterial pathogen via a Type II secretion system. In some cases, the intracellular domain comprises a toxic bacterial effector from Type III (e.g., *Salmonella, Shigella, Yersinia, Vibrio*) and type IV (e.g., *Bordetella pertussis, Legionella pneumophila, Agrobacterium tumefaciens*) secretion systems. Examples of toxic bacterial effectors from Type III bacterial secretion systems include, e.g., VopQ, YopH, and the like. See, e.g., Dean (2011) FEMS Microbiol. Rev. 35:1100. Examples of toxic bacterial effectors from Type IV bacterial secretion systems include, e.g., pertussis toxin, CagA, and the like.

In some cases, the intracellular domain can be a hormone. Examples of suitable hormones include, e.g., erythropoietin (EPO), insulin, secretins, glucagon-like polypeptide 1 (GLP-1), and the like. Further examples of such hormones include, but are not limited to, activin, inhibin, adiponectin, adipose-derived hormones, adrenocorticotropic hormone, Afamelanotide, agouti signaling peptide, Allatostatin, Amylin, Amylin family, angiotensin, atrial natriuretic peptide, gastrin, somatotropin, bradykinin, brain-derived neurotrophic factor, calcitonin, cholecystokinin, ciliary neurotrophic factor, corticotropin-releasing hormone, cosyntropin, endothelian, enteroglucagon, fibroblast growth factor 15 (FGF15), GFG15/19, follicle-stimulating hormone, gastrin, gastroinhibitory peptide, ghrelin, glucagon, glucagon-like peptide-1, gonadotropin, gonadotropin-releasing hormone, granulocyte-colony-stimulating factor, growth hormone, growth-hormone-releasing hormone, hepcidin, human chorionic gonadotropin, human placental lactogen, incretin, insulin, insulin analog, insulin aspart, insulin degludec, insulin glargine, insulin lispro, insulin-like growth factor, insulin-like growth factor-1, insulin-like growth factor-2, leptin, liraglutide, luteinizing hormone, melanocortin, melanocyte-stimulating hormone, alpha-melanocyte-stimulating hormone, melanotin II, minigastrin, N-terminal prohormone of brain natriuretic peptide, nerve growth factor, neurotrophin-3, neurotrophin-4, NPH insulin, obestatin, orexin, osteocalcin, pancreatic hormone, parathyroid hormone, peptide hormone, peptide YY, plasma renin activity, pramlintide, preprohormone, prolactin, relaxin, relaxin family peptide hormone, renin, salcatonin, secretin, secretin family peptide hormone, sincalide, teleost leptins, temporin, tesamorelin, thyroid-stimulating hormone, thyrotropin-releasing hormone, urocortin, urocortin II, urocortin III, vasoactive intestinal peptide, and vitellogenin.

In some cases, the intracellular domain comprises a growth factor. Examples of suitable growth factors include, but are not limited to, hepatocyte stimulating factor, plasmacytoma growth factor, brain derived neurotrophic factor (BDNF), glial derived neurotrophic factor (GDNF), neurotrophic factor 3 (NT3), fibroblast growth factor (FGF), transforming growth factor (TGF), platelet transforming growth factor, milk growth factor, endothelial growth factors (EGF), endothelial cell-derived growth factors (ECDGF), alpha-endothelial growth factor, beta-endothelial growth factor, neurotrophic growth factor, nerve growth factor (NGF), vascular endothelial growth factor (VEGF), 4-1 BB receptor (4-1BBR), TRAIL (TNF-related apoptosis inducing ligand), artemin (GFRalpha3-RET ligand), BCA-1 (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, megakaryocyte derived growth factor (MGDF), keratinocyte growth factor (KGF), thrombopoietin, platelet-derived growth factor (PGDF), megakaryocyte derived growth factor (MGDF), keratinocyte growth factor (KGF), platelet-derived growth factor (PGDF), neurotrophin-2 (NT-2), neurotrophin-3 (NT-3), neurotrophin-4 (NT4), neurotrophin-5 (NT-5), glial cell line-derived neurotrophic factor (GDNF), ciliary neurotrophic factor (CNTF), bone Morphogenetic protein 2 (BMP2), granulocyte macrophage colony stimulating factor (GM-CSF), granulocyte colony stimulating factor (G-CSF), macrophage colony stimulating factor (M-CSF), colony stimulating factor (CSF), and the like.

In some cases, the intracellular domain comprises a cytokine (e.g., pro-inflammatory or anti-inflammatory cytokine). Examples of suitable cytokines include, e.g., interferons (e.g., an alpha-interferon, a beta-interferon, a gamma-interferon); interleukins (e.g., IL-1, IL-1α, IL-2, IL-3, IL-4, IL-5, IL-6, IL-7, IL-8, IL-9, IL-10 IL-11, IL-12; IL-13, IL-14, IL-15, IL-16, IL-17, IL-17A, IL-18, IL-19, IL-20, IL-24); tumor necrosis factors (e.g., TNF-α); transforming growth factor-beta; TRAIL; and the like. Examples of suitable cytokines also include flexi-12 (Anderson et al. (1997) Hum. Gene Ther. 8:1125), a single chain polypeptide that combines the two polypeptide chains of an IL-12 heterodimer); IL-12 superkine H9 (Levin et al. (2012) Nature 484:529); and the like.

In some cases, the intracellular domain comprises a chemokine. Examples of suitable chemokines include, e.g., MIP-1, MIP-1β, MCP-1, RANTES, IP10, and the like. Additional examples of suitable chemokines include, but are not limited to, chemokine (C-C motif) ligand-2 (CCL2; also referred to as monocyte chemotactic protein-1 or MCP1); chemokine (C-C motif) ligand-3 (CCL3; also known as macrophage inflammatory protein-1A or MIP1A); chemokine (C-C motif) ligand-5 (CCLS; also known as RANTES); chemokine (C-C motif) ligand-17 (CCL17; also known as thymus and activation regulated chemokine or TARC); chemokine (C-C motif) ligand-19 (CCL19; also known as EBI1 ligand chemokine or ELC); chemokine (C-C motif) ligand-21 (CCL21; also known as 6Ckine); C-C chemokine receptor type 7 (CCR7); chemokine (C-X-C motif) ligand 9 (CXCL9; also known as monokine induced by gamma interferon or MIG); chemokine (C-X-C motif) ligand 10 (CXCL10; also known as interferon gamma-induced protein 10 or IP-10); chemokine (C-X-C motif) ligand 11 (CXCL11; also called interferon-inducible T-cell alpha chemoattractant or I-TAC); chemokine (C-X-C motif) ligand 16 (CXCL16; chemokine (C motif) ligand (XCL1; also known as lymphotactin); and macrophage colony-stimulating factor (MCSF).

In some cases, the intracellular domain comprises an antibody or an antigen-binding fragment of an antibody. Suitable antibodies include, e.g., Natalizumab (Tysabri; Biogen Idec/Elan) targeting a4 subunit of a4131 and a407 integrins (as used in the treatment of MS and Crohn's disease); Vedolizumab (MLN2; Millennium Pharmaceuticals/Takeda) targeting a407 integrin (as used in the treatment of UC and Crohn's disease); Belimumab (Benlysta; Human Genome Sciences/GlaxoSmithKline) targeting BAFF (as used in the treatment of SLE); Atacicept (TACI-Ig; Merck/Serono) targeting BAFF and APRIL (as used in the treatment of SLE); Alefacept (Amevive; Astellas) targeting CD2 (as used in the treatment of Plaque psoriasis, GVHD); Otelixizumab (TRX4; Tolerx/GlaxoSmithKline) targeting CD3 (as used in the treatment of TlD); Teplizumab (MGA031; MacroGenics/Eli Lilly) targeting CD3 (as used in the treatment of TlD); Rituximab (Rituxan/Mabthera; Genentech/Roche/Biogen Idec) targeting CD20 (as used in the treatment of Non-Hodgkin's lymphoma, RA (in patients with inadequate responses to TNF blockade) and CLL); Ofatumumab (Arzerra; Genmab/GlaxoSmithKline) targeting CD20 (as used in the treatment of CLL, RA); Ocrelizumab (2H7; Genentech/Roche/Biogen Idec) targeting CD20 (as used in the treatment of RA and SLE); Epratuzumab (hLL2; Immunomedics/UCB) targeting CD22 (as used in the treatment of SLE and non-Hodgkin's lymphoma); Alemtuzumab (Campath/MabCampath; Genzyme/Bayer) targeting CD52 (as used in the treatment of CLL, MS); Abatacept (Orencia; Bristol-Myers Squibb) targeting CD80 and CD86 (as used in the treatment of RA and JIA, UC and Crohn's disease, SLE); Eculizumab (Soliris; Alexion pharmaceuticals) targeting C5 complement protein (as used in the treatment of Paroxysmal nocturnal haemoglobinuria); Omalizumab (Xolair; Genentech/Roche/Novartis) targeting IgE (as used in the treatment of Moderate to severe persistent allergic asthma); Canakinumab (Ilaris; Novartis) targeting IL-1β (as used in the treatment of Cryopyrin-associated periodic syndromes, Systemic JIA, neonatal-onset multisystem inflammatory disease and acute gout); Mepolizumab (Bosatria; GlaxoSmithKline) targeting IL-5 (as used in the treatment of Hyper-eosinophilic syndrome); Reslizumab (SCH55700; Ception Therapeutics) targeting IL-5 (as used in the treatment of Eosinophilic oesophagitis); Tocilizumab (Actemra/RoActemra; Chugai/Roche) targeting IL-6R (as used in the treatment of RA, JIA); Ustekinumab (Stelara; Centocor) targeting IL-12 and IL-23 (as used in the treatment of Plaque psoriasis, Psoriatic arthritis, Crohn's disease); Briakinumab (ABT-874; Abbott) targeting IL-12 and IL-23 (as used in the treatment of Psoriasis and plaque psoriasis); Etanercept (Enbrel; Amgen/Pfizer) targeting TNF (as used in the treatment of RA, JIA, psoriatic arthritis, AS and plaque psoriasis); Infliximab (Remicade; Centocor/Merck) targeting TNF (as used in the treatment of Crohn's disease, RA, psoriatic arthritis, UC, AS and plaque psoriasis); Adalimumab (Humira/Trudexa; Abbott) targeting TNF (as used in the treatment of RA, JIA, psoriatic arthritis, Crohn's disease, AS and plaque psoriasis); Certolizumab pegol (Cimzia; UCB) targeting TNF (as used in the treatment of Crohn's disease and RA); Golimumab (Simponi; Centocor) targeting TNF (as used in the treatment of RA, psoriatic arthritis and AS); and the like. In some cases, the antibody whose production is induced by the intracellular domain is a therapeutic antibody for the treatment of cancer. Such antibodies include, e.g., Ipilimumab targeting CTLA-4 (as used in the treatment of Melanoma, Prostate Cancer, RCC); Tremelimumab targeting CTLA-4 (as used in the treatment of CRC, Gastric, Melanoma, NSCLC); Nivolumab targeting PD-1 (as used in the treatment of Melanoma, NSCLC, RCC); MK-3475 targeting PD-1 (as used in the treatment of Melanoma); Pidilizumab targeting PD-1 (as used in the treatment of Hematologic Malignancies); BMS-936559 targeting PD-L1 (as used in the treatment of Melanoma, NSCLC, Ovarian, RCC); MEDI4736 targeting PD-Li; MPDL33280A targeting PD-L1 (as used in the treatment of Melanoma); Rituximab targeting CD20 (as used in the treatment of Non-Hodgkin's lymphoma); Ibritumomab tiuxetan and tositumomab (as used in the treatment of Lymphoma); Brentuximab vedotin targeting CD30 (as used in the treatment of Hodgkin's lymphoma); Gemtuzumab ozogamicin targeting CD33 (as used in the treatment of Acute myelogenous leukemia); Alemtuzumab targeting CD52 (as used in the treatment of Chronic lymphocytic leukemia); IGN101 and adecatumumab targeting EpCAM (as used in the treatment of Epithelial tumors (breast, colon and lung)); Labetuzumab targeting CEA (as used in the treatment of Breast, colon and lung tumors); huA33 targeting gpA33 (as used in the treatment of Colorectal carcinoma); Pemtumomab and oregovomab targeting Mucins (as used in the treatment of Breast, colon, lung and ovarian tumors); CC49 (minretumomab) targeting TAG-72 (as used in the treatment of Breast, colon and lung tumors); cG250 targeting CAIX (as used in the treatment of Renal cell carcinoma); J591 targeting PSMA (as used in the treatment of Prostate carcinoma); MOv18 and MORAb-003 (farletuzumab) targeting Folate-binding protein (as used in the treatment of Ovarian tumors); 3F8, ch14.18 and KW-2871 targeting Gangliosides (such as GD2, GD3 and GM2) (as used in the treatment of Neuroectodermal tumors and some epithelial tumors); hu3 S193 and IgN311 targeting Le y (as used in the treatment of Breast, colon, lung and prostate tumors); Bevacizumab targeting VEGF (as used in the treatment of Tumor vasculature); IM-2C6 and CDP791 targeting VEGFR (as used in the treatment of Epithelium-derived solid tumors); Etaracizumab targeting Integrin_V_3 (as used in the treatment of Tumor vasculature); Volociximab targeting Integrin_5_1 (as used in the treatment of Tumor vasculature); Cetuximab, panitumumab, nimotuzumab and 806 targeting EGFR (as used in the treatment of Glioma, lung, breast, colon, and head and neck tumors); Trastuzumab and pertuzumab targeting ERBB2 (as used in the treatment of Breast, colon, lung, ovarian and prostate tumors); MM-121 targeting ERBB3 (as used in the treatment of Breast, colon, lung, ovarian and prostate, tumors); AMG 102, METMAB and SCH 900105 targeting MET (as used in the treatment of Breast, ovary and lung tumors); AVE1642, IMC-A12, MK-0646, R1507 and CP 751871 targeting IGF1R (as used in the treatment of Glioma, lung, breast, head and neck, prostate and thyroid cancer); KB004 and IIIA4 targeting EPHA3 (as used in the treatment of Lung, kidney and colon tumors, melanoma, glioma and hematological malignancies); Mapatumumab (HGS-ETR1) targeting TRAILR1 (as used in the treatment of Colon, lung and pancreas tumors and hematological malignancies); HGS-ETR2 and CS-1008 targeting TRAILR2; Denosumab targeting RANKL (as used in the treatment of Prostate cancer and bone metastases); Sibrotuzumab and F19 targeting FAP (as used in the treatment of Colon, breast, lung, pancreas, and head and neck tumors); 8106 targeting Tenascin (as used in the treatment of Glioma, breast and prostate tumors); Blinatumomab (Blincyto; Amgen) targeting CD3 (as used in the treatment of ALL); pembrolizumab targeting PD-1 as used in cancer immunotherapy; 9E10 antibody targeting c-Myc; and the like.

Antibodies that can find use, in whole or in part, as an intracellular domain of an engineered receptor as described herein also include, but are not limited to, 8H9, Abagovomab, Abciximab, Abituzumab, Abrilumab, Actoxumab, Aducanumab, Afelimomab, Afutuzumab, Alacizumab pegol, ALD518, Alirocumab, Altumomab pentetate, Amatuximab, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab/tocilizumab, Atorolimumab, Bapineuzumab, Basiliximab, Bavituximab, Bectumomab, Begelomab, Benralizumab, Bertilimumab, Besilesomab, Bevacizumab/Ranibizumab, Bezlotoxumab, Biciromab, Bimagrumab, Bimekizumab, Bivatuzumab mertansine, Blosozumab, Bococizumab, Brentuximabvedotin, Brodalumab, Brolucizumab, Brontictuzumab, Cantuzumab mertansine, Cantuzumab ravtansine, Caplacizumab, Capromab pendetide, Carlumab, Catumaxomab, cBR96-doxorubicin immunoconjugate, Cedelizumab, Ch.14.18, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Dacetuzumab, Daclizumab, Dalotuzumab, Dapirolizumab pegol, Daratumumab, Dectrekumab, Demcizumab, Denintuzumab mafodotin, Derlotuximab biotin, Detumomab, Dinutuximab, Diridavumab, Dorlimomab aritox, Drozitumab, Duligotumab, Dupilumab, Durvalumab, Dusigitumab, Ecromeximab, Edobacomab, Edrecolomab, Efalizumab, Efungumab, Eldelumab, Elgemtumab, Elotuzumab, Elsilimomab, Emactuzumab, Emibetuzumab, Enavatuzumab, Enfortumab vedotin, Enlimomab pegol, Enoblituzumab, Enokizumab, Enoticumab, Ensituximab, Epitumomab cituxetan, Erlizumab, Ertumaxomab, Etrolizumab, Evinacumab, Evolocumab, Exbivirumab, Fanolesomab, Faralimomab, Farletuzumab, Fasinumab, FBTA05, Felvizumab, Fezakinumab, Ficlatuzumab, Figitumumab, Firivumab, Flanvotumab, Fletikumab, Fontolizumab, Foralumab, Foravirumab, Fresolimumab, Fulranumab, Futuximab, Galiximab, Ganitumab, Gantenerumab, Gavilimomab, Gevokizumab, Girentuximab, Glembatumumab vedotin, Gomiliximab, Guselkumab, Ibalizumab, Ibalizumab, Icrucumab, Idarucizumab, Igovomab, IMAB362, Imalumab, Imciromab, Imgatuzumab, Inclacumab, Indatuximab ravtansine, Indusatumab vedotin, Inolimomab, Inotuzumab ozogamicin, Intetumumab, Iratumumab, Isatuximab, Itolizumab, Ixekizumab, Keliximab, Lambrolizumab, Lampalizumab, Lebrikizumab, Lemalesomab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Margetuximab, Maslimomab, Matuzumab, Mavrilimumab, Metelimumab, Milatuzumab, Minretumomab, Mirvetuximab soravtansine, Mitumomab, Mogamulizumab, Morolimumab, Morolimumab immune, Motavizumab, Moxetumomab pasudotox, Muromonab-CD3, Nacolomab tafenatox, Namilumab, Naptumomab estafenatox, Narnatumab, Nebacumab, Necitumumab, Nemolizumab, Nerelimomab, Nesvacumab, Nofetumomab merpentan, Obiltoxaximab, Obinutuzumab, Ocaratuzumab, Odulimomab, Olaratumab, Olokizumab, Onartuzumab, Ontuxizumab, Opicinumab, Oportuzumab monatox, Orticumab, Otlertuzumab, Oxelumab, Ozanezumab, Ozoralizumab, Pagibaximab, Palivizumab, Pankomab, Panobacumab, Parsatuzumab, Pascolizumab, Pasotuxizumab, Pateclizumab, Patritumab, Perakizumab, Pexelizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Rilotumumab, Rinucumab, Robatumumab, Roledumab, Romosozumab, Rontalizumab, Rovelizumab, Ruplizumab, Sacituzumab govitecan, Samalizumab, Sarilumab, Satumomab pendetide, Secukinumab, Seribantumab, Setoxaximab, Sevirumab, SGN-CD19A, SGN-CD33A, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Tefibazumab, Telimomab aritox, Tenatumomab, Teneliximab, Teprotumumab, Tesidolumab, Tetulomab, TGN1412, Ticilimumab/tremelimumab, Tigatuzumab, Tildrakizumab, TNX-650, Toralizumab, Tosatoxumab, Tovetumab, Tralokinumab, TRBS07, Tregalizumab, Trevogrumab, Tucotuzumab celmoleukin, Tuvirumab, Ublituximab, Ulocuplumab, Urelumab, Urtoxazumab, Vandortuzumab vedotin, Vantictumab, Vanucizumab, Vapaliximab, Varlilumab, Vatelizumab, Veltuzumab, Vepalimomab, Vesencumab, Visilizumab, Vorsetuzumab mafodotin, Votumumab, Zalutumumab, Zanolimumab, Zatuximab, Ziralimumab, Zolimomab aritox, and the like.

In some cases, the intracellular domain comprises a neuropeptide. Examples of suitable neuropeptides include, but are not limited to, N-Acetylaspartylglutamic acid, agouti-related peptide, alpha-endorphin, big dynorphin, bombesin, bombesin-like peptides, carbetocin, cocaine-and-amphetamine regulated transcript (CART), cholecystokinin, corazonin, corticotropin-like intermediate peptide, cortistatin, demoxytocin, dynorphin A, dynorphin B, eledoisin, enkephalin, galanin, galanin-like peptide, galmic, galnon, gamma-endorphin, ghrelin, hemopressin, kisspeptin, neurokinin B, neuromedin B, neuromedin N, neuromedin S, neuromedin U, neuromedin S, neuromedin Y, neuropeptide Y, neurotensin, nociceptin, opiorphin, orexin, orexin-A, oxytocin, physalaemin, preprotachykinin, proctolin, proenkephalin, poopiomelanocortin, protein episteme, relaxin-3, somatostatin, substance P, TAC1, tachykinin peptides, vasopressin, and vasotocin.

In certain embodiments, the intracellular effector domain comprises a detectable protein. Suitable detectable proteins include, e.g., fluorescent proteins; enzymes that catalyze a reaction that generates a detectable signal as a product; and the like. Exemplary fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) Nat. Methods 2:905-909), and the like. Any of a variety of fluorescent and colored proteins from Anthozoan species, as described in, e.g., Matz et al. (1999) Nature Biotechnol. 17:969-973, is suitable for use.

Non-limiting examples of enzymes that produce a detectable product include, but are not limited to, horse radish peroxidase (HRP), alkaline phosphatase (AP), beta-galactosidase (GAL), glucose-6-phosphate dehydrogenase, beta-N-acetylglucosaminidase, 0-glucuronidase, invertase, Xanthine Oxidase, firefly luciferase, glucose oxidase (GO), and the like.

In some embodiments, the intracellular effector domain comprises a nucleic acid, such as a messenger RNA (mRNA), micro RNA (miRNA), double-stranded DNA (dsDNA), cDNA, or an RNA interference molecule, such as a small hairpin RNA (shRNA), small interfering RNA (siRNA) and the like.

In some embodiments, the intracellular effector domain can comprise a suitable intracellular localization signal to direct the intracellular effector domain to a particular subcellular compartment. For example, Suitable nuclear localization signals ("NLS"; also referred to herein as "nuclear localization sequences") include, e.g., PKKKRKV (SEQ ID NO: 11); KRPAATKKAGQAKKKK (SEQ ID NO: 12); MVPKKKRK (SEQ ID NO: 13); MAPKKKRKVGIHGVPAA (SEQ ID NO: 14); and the like. Additional exemplary localization sequences are found herein in Table 1.

TABLE 1

Subcellular localization sequences

| SEQ ID NO: | Amino Terminal Sequence | Subcellular Compartment |
|---|---|---|
| 15 | GCVCSSNP | plasma membrane |
| 16 | GQTVTTPL | plasma membrane |
| 17 | GQELSQHE | plasma membrane |
| 18 | GNSPSYNP | plasma membrane |
| 19 | GVSGSKGQ | plasma membrane |
| 20 | GQTTTTPL | plasma membrane |
| 21 | GQIFSRSA | plasma membrane |
| 22 | GQIHGLSP | plasma membrane |
| 23 | GARASVLS | plasma membrane |
| 24 | GCTLSAEE | plasma membrane |
| 25 | GQNLSTSN | endoplasmic reticulum |
| 26 | GAALTILV | nucleus |
| 27 | GAALTLLG | nucleus |
| 28 | GAQVSSQK | cytoplasm (soluble), endoplasmic reticulum |
| 29 | GAQLSRNT | cytoplasm (soluble), cytoplasm, endoplasmic reticulum |
| 30 | GNAAAAKK | Golgi, cytoplasm, nucleus |
| 31 | GNEASYPL | cytoplasm |
| 32 | GSSKSKPK | plasma membrane, cytoplasm |

Gene Products Induced by a Released Intracellular Domain

In some cases, the intracellular domain is a polypeptide that, when released upon binding of the ligand to the ligand binding domain induces production of a gene product (e.g., a protein or nucleic acid). In some embodiments, the gene product is a nucleic acid. In other embodiments, the gene product is a polypeptide.

Polypeptide gene products induced by the released intracellular domain include endogenous polypeptides (e.g., polypeptides naturally encoded by the cell) and heterologous polypeptides (e.g., polypeptides not naturally encoded by the cell; polypeptides encoded by a heterologous nucleic acid used to genetically modify the cell). Polypeptide gene products induced by the released intracellular domain include secreted polypeptides. Polypeptide gene products induced by the released intracellular domain include cell surface polypeptides. Polypeptide gene products induced by the released intracellular domain include intracellular polypeptides (polypeptides that normally are present intracellularly, such as transcription factors). Polypeptide gene products induced by the released intracellular domain include receptors, cytokines, hormones, growth factors, chemokines, cell surface polypeptides, transcription factors (e.g., transcription activators; transcription repressors), apoptosis inducers, apoptosis inhibitors, dominant-negative variants, etc.

Polypeptide gene products whose production can be induced by the released intracellular domain include transcriptional activators, transcriptional repressors, a chimeric antigen receptor, a T-cell receptor (TCR), a chimeric Notch polypeptide (e.g., synNotch), a CAR, a translation regulator, an immune inhibitory receptor, an immune inhibitory protein, an immune activating protein, a cytokine receptor, a chemokine receptor, a DNA-binding protein, an epigenetic regulator, an RNA-guided endonuclease (e.g., a Cas9 polypeptide), an enzymatically inactive Cas9 polypeptide, a site-specific nuclease, a recombinase, a transcription factor that induces differentiation, a transcription factor that induces dedifferentiation, and the like.

In some cases, the intracellular domain released as described herein induces production of an endogenous gene product in a cell that expresses the engineered receptor. Endogenous gene products include, e.g., a chemokine, a chemokine receptor, a cytokine, a cytokine receptor, a differentiation factor, a growth factor, a growth factor receptor, a hormone, a metabolic enzyme, a proliferation inducer, a receptor, a small molecule second messenger synthesis enzyme, a T cell receptor, a transcription activator, a transcription repressor, a transcriptional activator, a transcriptional repressor, a translation regulator, a translational activator, a translational repressor, an activating immunoreceptor, an apoptosis in inhibitor, an apoptosis inducer, an immunoactivator, an immunoinhibitor, and an inhibiting immunoreceptor.

In some cases, the intracellular domain, when released upon binding the ligand binding domain to its cognate ligand, induces production of a heterologous gene product in a cell that expresses the engineered receptor. Heterologous gene products include gene products not normally produced by the cell. For example, the cell can be genetically modified with a nucleic acid comprising a nucleotide sequence encoding a heterologous gene product. Heterologous gene products include, e.g., a chemokine, a chemokine receptor, a chimeric antigen receptor, a cytokine, a cytokine receptor, a differentiation factor, a growth factor, a growth factor receptor, a hormone, a metabolic enzyme, a pathogen derived protein, a proliferation inducer, a receptor, a RNA guided nuclease, a site-specific nuclease, a small molecule second messenger synthesis enzyme, a T cell receptor, a toxin derived protein, a transcription activator, a transcription repressor, a transcriptional activator, a transcriptional repressor, a translation regulator, a translational activator, a translational repressor, an activating immunoreceptor, an antibody, an apoptosis in inhibitor, an apoptosis inducer, an engineered T cell receptor, an immunoactivator, an immunoinhibitor, an inhibiting immunoreceptor, an RNA guided DNA binding protein, a T-cell receptor (TCR), a MESA polypeptide, a TANGO polypeptide, and a second engineered receptor (where the second engineered receptor is different from the engineered receptor whose intracellular domain induced production of the second engineered receptor polypeptide).

Polypeptide gene products that can be induced by the released intracellular domain include secreted polypeptides. Non-limiting examples of secreted polypeptides include, e.g., IL-2, IL-7, TNFalpha, IL-12, GMCSF, EGF, TGFbeta, IL-10, IL-17, IL-4, IL-5, IL-13, IFNalpha, IFNgamma, HMG-B1, secreted PTEN, Wnt, and single chain antibodies. Polypeptide gene products that can be induced by the released intracellular domain include dominant negative polypeptides. Examples of dominant negative polypeptides include, e.g., a dominant negative TGF-β receptor; a dominant negative variant of STAT3 comprising one or more mutations affecting the DNA binding domain of STAT3 that functions as a dominant negative variant; and the like.

In some cases, the released intracellular domain induces production of a hormone in a cell that expresses the engineered receptor. Examples of such hormones include, e.g., erythropoietin (EPO), insulin, secretins, glucagon-like polypeptide 1 (GLP-1), and the like. Further examples of such hormones include, but are not limited to, activin, inhibin, adiponectin, adipose-derived hormones, adrenocorticotropic hormone, afamelanotide, agouti signaling peptide, allatostatin, amylin, angiotensin, atrial natriuretic peptide, gastrin, somatotropin, bradykinin, brain-derived neurotrophic factor, calcitonin, cholecystokinin, ciliary neurotrophic factor, corticotropin-releasing hormone, cosyntropin, endothelian, enteroglucagon, fibroblast growth factor 15 (FGF15), GFG15/19, follicle-stimulating hormone, gastrin, gastroinhibitory peptide, ghrelin, glucagon, glucagon-like peptide-1, gonadotropin, gonadotropin-releasing hormone, granulocyte-colony-stimulating factor, growth hormone, growth-hormone-releasing hormone, hepcidin, human chorionic gonadotropin, human placental lactogen, incretin, insulin, insulin analog, insulin aspart, insulin degludec, insulin glargine, insulin lispro, insulin-like growth factor, insulin-like growth factor-1, insulin-like growth factor-2, leptin, liraglutide, luteinizing hormone, melanocortin, melanocyte-stimulating hormone, alpha-melanocyte-stimulating hormone, melanotin II, minigastrin, N-terminal prohormone of brain natriuretic peptide, nerve growth factor, neurotrophin-3, neurotrophin-4, NPH insulin, obestatin, orexin, osteocalcin, pancreatic hormone, parathyroid hormone, peptide hormone, peptide YY, plasma renin activity, pramlintide, preprohormone, prolactin, relaxin, relaxin family peptide hormone, renin, salcatonin, secretin, secretin family peptide hormone, sincalide, teleost leptins, temporin, tesamorelin, thyroid-stimulating hormone, thyrotropin-releasing hormone, urocortin, urocortin II, urocortin III, vasoactive intestinal peptide, and vitellogenin.

In some cases, the intracellular domain released as described herein induces production of a growth factor in a cell that expresses the engineered receptor. Examples of such growth factors include, but are not limited to, hepatocyte stimulating factor, plasmacytoma growth factor, brain derived neurotrophic factor (BDNF), glial derived neurotrophic factor (GDNF), neurotrophic factor 3 (NT3), fibroblast growth factor (FGF), transforming growth factor (TGF), platelet transforming growth factor, milk growth factor, endothelial growth factors (EGF), endothelial cell-derived growth factors (ECDGF), alpha-endothelial growth factor, beta-endothelial growth factor, neurotrophic growth factor, nerve growth factor (NGF), vascular endothelial growth factor (VEGF), 4-1 BB receptor (4-1BBR), TRAIL (TNF-related apoptosis inducing ligand), artemin (GFRalpha3-RET ligand), BCA-1 (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, megakaryocyte derived growth factor (MGDF), keratinocyte growth factor (KGF), thrombopoietin, platelet-derived growth factor (PGDF), megakaryocyte derived growth factor (MGDF), keratinocyte growth factor (KGF), platelet-derived growth factor (PGDF), neurotrophin-2 (NT-2), neurotrophin-3 (NT-3), neurotrophin-4 (NT4), neurotrophin-5 (NT-5), glial cell line-derived neurotrophic factor (GDNF), ciliary neurotrophic factor (CNTF), bone Morphogenetic protein 2 (BMP2), granulocyte macrophage colony stimulating factor (GM-CSF), granulocyte colony stimulating factor (G-CSF), macrophage colony stimulating factor (M-CSF), colony stimulating factor (CSF), and the like.

In some cases, the intracellular domain released as described herein induces production of a cytokine in a cell that expresses the engineered receptor. Examples of such cytokines include, e.g., interferons (e.g., an alpha-interferon, a beta-interferon, a gamma-interferon); interleukins (e.g., IL-1, IL-1α, IL-2, IL-3, IL-4, IL-5, IL-6, IL-7, IL-8, IL-9, IL-10 IL-11, IL-12; IL-13, IL-14, IL-15, IL-16, IL-17, IL-17A, IL-18, IL-19, IL-20, IL-24); tumor necrosis factors (e.g., TNF-α); transforming growth factor-beta; TRAIL; and the like. Examples of such cytokines also include flexi-12 (Anderson et al. (1997) Hum. Gene Ther. 8:1125), a single chain polypeptide that combines the two polypeptide chains of an IL-12 heterodimer); IL-12 superkine H9 (Levin et al. (2012) Nature 484:529); and the like.

In some cases, the intracellular domain, when released upon binding of the ligand to the ligand binding domain, induces production of a chemokine in a cell that expresses the engineered receptor. Examples of such chemokines include, e.g., MIP-1, MIP-10, MCP-1, RANTES, IP10, and the like. Additional examples of suitable chemokines include, but are not limited to, chemokine (C-C motif) ligand-2 (CCL2; also referred to as monocyte chemotactic protein-1 or MCP1); chemokine (C-C motif) ligand-3 (CCL3; also known as macrophage inflammatory protein-1A or MIP1A); chemokine (C-C motif) ligand-5 (CCLS; also known as RANTES); chemokine (C-C motif) ligand-17 (CCL17; also known as thymus and activation regulated chemokine or TARC); chemokine (C-C motif) ligand-19 (CCL19; also known as EBI1 ligand chemokine or ELC); chemokine (C-C motif) ligand-21 (CCL21; also known as 6Ckine); C-C chemokine receptor type 7 (CCR7); chemokine (C-X-C motif) ligand 9 (CXCL9; also known as monokine induced by gamma interferon or MIG); chemokine (C-X-C motif) ligand 10 (CXCL10; also known as interferon gamma-induced protein 10 or IP-10); chemokine (C-X-C motif) ligand 11 (CXCL11; also called interferon-inducible T-cell alpha chemoattractant or I-TAC); chemokine (C-X-C motif) ligand 16 (CXCL16; chemokine (C motif) ligand (XCL1; also known as lymphotactin); and macrophage colony-stimulating factor (MCSF).

In some cases, the intracellular domain of an engineered receptor, when released upon binding of ligand to the ligand binding domain, induces production of an antibody in a cell that expresses the engineered receptor as described herein. Such antibodies include, e.g., Natalizumab (Tysabri; Biogen Idec/Elan) targeting a4 subunit of a4131 and a407 integrins (as used in the treatment of MS and Crohn's disease); Vedolizumab (MLN2; Millennium Pharmaceuticals/Takeda) targeting a407 integrin (as used in the treatment of UC and Crohn's disease); Belimumab (Benlysta; Human Genome Sciences/GlaxoSmithKline) targeting BAFF (as used in the treatment of SLE); Atacicept (TACI-Ig; Merck/Serono) targeting BAFF and APRIL (as used in the treatment of SLE); Alefacept (Amevive; Astellas) targeting CD2 (as used in the treatment of Plaque psoriasis, GVHD); Otelixizumab (TRX4; Tolerx/GlaxoSmithKline) targeting CD3 (as used in the treatment of TID); Teplizumab (MGA031; MacroGenics/Eli Lilly) targeting CD3 (as used in the treatment of TID); Rituximab (Rituxan/Mabthera; Genentech/Roche/Biogen Idec) targeting CD20 (as used in the treatment of Non-Hodgkin's lymphoma, RA (in patients with inadequate responses to TNF blockade) and CLL); Ofatumumab (Arzerra; Genmab/GlaxoSmithKline) targeting CD20 (as used in the treatment of CLL, RA); Ocrelizumab (2H7; Genentech/Roche/Biogen Idec) targeting CD20 (as used in the treatment of RA and SLE); Epratuzumab (hLL2; Immunomedics/UCB) targeting CD22 (as used in the treatment of SLE and non-Hodgkin's lymphoma); Alemtuzumab (Campath/MabCampath; Genzyme/Bayer) targeting CD52 (as used in the treatment of CLL, MS); Abatacept (Orencia; Bristol-Myers Squibb) targeting CD80 and CD86 (as used in the treatment of RA and JIA, UC and Crohn's disease, SLE); Eculizumab (Soliris; Alexion pharmaceuticals) targeting C5 complement protein (as used in the treatment of Paroxysmal nocturnal haemoglobinuria); Omalizumab (Xolair; Genentech/Roche/Novartis) targeting IgE (as used in the treatment of Moderate to severe persistent allergic asthma); Canakinumab (Ilaris; Novartis) targeting IL-10 (as used in the treatment of Cryopyrin-associated periodic syndromes, Systemic JIA, neonatal-onset multisystem inflammatory disease and acute gout); Mepolizumab (Bosatria; GlaxoSmithKline) targeting IL-5 (as used in the treatment of Hyper-eosinophilic syndrome); Reslizumab (SCH55700; Ception Therapeutics) targeting IL-5 (as used in the treatment of Eosinophilic oesophagitis); Tocilizumab (Actemra/RoActemra; Chugai/Roche) targeting IL-6R (as used in the treatment of RA, JIA); Ustekinumab (Stelara; Centocor) targeting IL-12 and IL-23 (as used in the treatment of Plaque psoriasis, Psoriatic arthritis, Crohn's disease); Briakinumab (ABT-874; Abbott) targeting IL-12 and IL-23 (as used in the treatment of Psoriasis and plaque psoriasis); Etanercept (Enbrel; Amgen/Pfizer) targeting TNF (as used in the treatment of RA, JIA, psoriatic arthritis, AS and plaque psoriasis); Infliximab (Remicade; Centocor/Merck) targeting TNF (as used in the treatment of Crohn's disease, RA, psoriatic arthritis, UC, AS and plaque psoriasis); Adalimumab (Humira/Trudexa; Abbott) targeting TNF (as used in the treatment of RA, JIA, psoriatic arthritis, Crohn's disease, AS and plaque psoriasis); Certolizumab pegol (Cimzia; UCB) targeting TNF (as used in the treatment of Crohn's disease and RA); Golimumab (Simponi; Centocor) targeting TNF (as used in the treatment of RA, psoriatic arthritis and AS); and the like. In some cases, the antibody whose production is induced by the intracellular domain is a therapeutic antibody for the treatment of cancer. Such antibodies include, e.g., Ipilimumab targeting CTLA-4 (as used in the treatment of Melanoma, Prostate Cancer, RCC); Tremelimumab targeting CTLA-4 (as used in the treatment of CRC, Gastric, Melanoma, NSCLC); Nivolumab targeting PD-1 (as used in the treatment of Melanoma, NSCLC, RCC); MK-3475 targeting PD-1 (as used in the treatment of Melanoma); Pidilizumab targeting PD-1 (as used in the treatment of Hematologic Malignancies); BMS-936559 targeting PD-L1 (as used in the treatment of Melanoma, NSCLC, Ovarian, RCC); MEDI4736 targeting PD-Li; MPDL33280A targeting PD-L1 (as used in the treatment of Melanoma); Rituximab targeting CD20 (as used in the treatment of Non-Hodgkin's lymphoma); Ibritumomab tiuxetan and tositumomab (as used in the treatment of Lymphoma); Brentuximab vedotin targeting CD30 (as used in the treatment of Hodgkin's lymphoma); Gemtuzumab ozogamicin targeting CD33 (as used in the treatment of Acute myelogenous leukemia); Alemtuzumab targeting CD52 (as used in the treatment of Chronic lymphocytic leukemia); IGN101 and adecatumumab targeting EpCAM (as used in the treatment of Epithelial tumors (breast, colon and lung)); Labetuzumab targeting CEA (as used in the treatment of Breast, colon and lung tumors); huA33 targeting gpA33 (as used in the treatment of Colorectal carcinoma); Pemtumomab and oregovomab targeting Mucins (as used in the treatment of Breast, colon, lung and ovarian tumors); CC49 (minretumomab) targeting TAG-72 (as used in the treatment of Breast, colon and lung tumors); cG250 targeting CAIX (as used in the treatment of Renal cell carcinoma); J591 targeting PSMA (as used in the treatment of Prostate carcinoma); MOv18 and MORAb-003 (farletuzumab) targeting Folate-binding protein (as used in the treatment of Ovarian tumors); 3F8, chl4.18 and KW-2871 targeting Gangliosides (such as GD2, GD3 and GM2) (as used in the treatment of Neuroectodermal tumors and some epithelial tumors); hu3S193 and IgN311 targeting Le y (as used in the treatment of Breast, colon, lung and prostate tumors); Bevacizumab targeting VEGF (as used in the treatment of Tumor vasculature); IM-2C6 and CDP791 targeting VEGFR (as used in the treatment of Epithelium-derived solid tumors); Etaracizumab targeting Integrin_V_3 (as used in the treatment of Tumor vasculature); Volociximab targeting Integrin_5_1 (as used in the treatment of Tumor vasculature); Cetuximab, panitumumab, nimotuzumab and 806 targeting EGFR (as used in the treatment of Glioma, lung, breast, colon, and head and neck tumors); Trastuzumab and pertuzumab targeting ERBB2 (as used in the treatment of Breast, colon, lung, ovarian and prostate tumors); MM-121 targeting ERBB3 (as used in the treatment of Breast, colon, lung, ovarian and prostate, tumors); AMG 102, METMAB and SCH 900105 targeting MET (as used in the treatment of Breast, ovary and lung tumors); AVE1642, IMC-A12, MK-0646, R1507 and CP 751871 targeting IGF1R (as used in the treatment of Glioma, lung, breast, head and neck, prostate and thyroid cancer); KB004 and IIIA4 targeting EPHA3 (as used in the treatment of Lung, kidney and colon tumors, melanoma, glioma and hematological malignancies); Mapatumumab (HGS-ETR1) targeting TRAILR1 (as used in the treatment of Colon, lung and pancreas tumors and hematological malignancies); HGS-ETR2 and CS-1008 targeting TRAILR2; Denosumab targeting RANKL (as used in the treatment of Prostate cancer and bone metastases); Sibrotuzumab and F19 targeting FAP (as used in the treatment of Colon, breast, lung, pancreas, and head and neck tumors); 81C6 targeting Tenascin (as used in the treatment of Glioma, breast and prostate tumors); Blinatumomab (Blincyto; Amgen) targeting CD3 (as used in the treatment of ALL); pembrolizumab targeting PD-1 as used in cancer immunotherapy; 9E10 antibody targeting c-Myc; and the like.

Antibodies that may be expressed, in whole or in part, as the result of activation of an engineered receptor polypeptide construct, as described herein, also include but are not limited to 8H9, Abagovomab, Abciximab, Abituzumab, Abrilumab, Actoxumab, Aducanumab, Afelimomab, Afutuzumab, Alacizumab pegol, ALD518, Alirocumab, Altumomab pentetate, Amatuximab, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab/tocilizumab, Atorolimumab, Bapineuzumab, Basiliximab, Bavituximab, Bectumomab, Begelomab, Benralizumab, Bertilimumab, Besilesomab, Bevacizumab/Ranibizumab, Bezlotoxumab, Biciromab, Bimagrumab, Bimekizumab, Bivatuzumab mertansine, Blosozumab, Bococizumab, Brentuximabvedotin, Brodalumab, Brolucizumab, Brontictuzumab, Cantuzumab mertansine, Cantuzumab ravtansine, Caplacizumab, Capromab pendetide, Carlumab, Catumaxomab, cBR96-doxorubicin immunoconjugate, Cedelizumab, Ch.14.18, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Dacetuzumab, Daclizumab, Dalotuzumab, Dapirolizumab pegol, Daratumumab, Dectrekumab, Demcizumab, Denintuzumab mafodotin, Derlotuximab biotin, Detumomab, Dinutuximab, Diridavumab, Dorlimomab aritox, Drozitumab, Duligotumab, Dupilumab, Durvalumab, Dusigitumab, Ecromeximab, Edobacomab, Edrecolomab, Efalizumab, Efungumab, Eldelumab, Elgemtumab, Elotuzumab, Elsilimomab, Emactuzumab, Emibetuzumab, Enavatuzumab, Enfortumab vedotin, Enlimomab pegol, Enoblituzumab, Enokizumab, Enoticumab, Ensituximab, Epitumomab cituxetan, Erlizumab, Ertumaxomab, Etrolizumab, Evinacumab, Evolocumab, Exbivirumab, Fanolesomab, Faralimomab, Farletuzumab, Fasinumab, FBTA05, Felvizumab, Fezakinumab, Ficlatuzumab, Figitumumab, Firivumab, Flanvotumab, Fletikumab, Fontolizumab, Foralumab, Foravirumab, Fresolimumab, Fulranumab, Futuximab, Galiximab, Ganitumab, Gantenerumab, Gavilimomab, Gevokizumab, Girentuximab, Glembatumumab vedotin, Gomiliximab, Guselkumab, Ibalizumab, Ibalizumab, Icrucumab, Idarucizumab, Igovomab, IMAB362, Imalumab, Imciromab, Imgatuzumab, Inclacumab, Indatuximab ravtansine, Indusatumab vedotin, Inolimomab, Inotuzumab ozogamicin, Intetumumab, Iratumumab, Isatuximab, Itolizumab, Ixekizumab, Keliximab, Lambrolizumab, Lampalizumab, Lebrikizumab, Lemalesomab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Margetuximab, Maslimomab, Matuzumab, Mavrilimumab, Metelimumab, Milatuzumab, Minretumomab, Mirvetuximab soravtansine, Mitumomab, Mogamulizumab, Morolimumab, Morolimumab immune, Motavizumab, Moxetumomab pasudotox, Muromonab-CD3, Nacolomab tafenatox, Namilumab, Naptumomab estafenatox, Narnatumab, Nebacumab, Necitumumab, Nemolizumab, Nerelimomab, Nesvacumab, Nofetumomab merpentan, Obiltoxaximab, Obinutuzumab, Ocaratuzumab, Odulimomab, Olaratumab, Olokizumab, Onartuzumab, Ontuxizumab, Opicinumab, Oportuzumab monatox, Orticumab, Otlertuzumab, Oxelumab, Ozanezumab, Ozoralizumab, Pagibaximab, Palivizumab, Pankomab, Panobacumab, Parsatuzumab, Pascolizumab, Pasotuxizumab, Pateclizumab, Patritumab, Perakizumab, Pexelizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Rilotumumab, Rinucumab, Robatumumab, Roledumab, Romosozumab, Rontalizumab, Rovelizumab, Ruplizumab, Sacituzumab govitecan, Samalizumab, Sarilumab, Satumomab pendetide, Secukinumab, Seribantumab, Setoxaximab, Sevirumab, SGN-CD19A, SGN-CD33A, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Tefibazumab, Telimomab aritox, Tenatumomab, Teneliximab, Teprotumumab, Tesidolumab, Tetulomab, TGN1412, Ticilimumab/tremelimumab, Tigatuzumab, Tildrakizumab, TNX-650, Toralizumab, Tosatoxumab, Tovetumab, Tralokinumab, TRBS07, Tregalizumab, Trevogrumab, Tucotuzumab celmoleukin, Tuvirumab, Ublituximab, Ulocuplumab, Urelumab, Urtoxazumab, Vandortuzumab vedotin, Vantictumab, Vanucizumab, Vapaliximab, Varlilumab, Vatelizumab, Veltuzumab, Vepalimomab, Vesencumab, Visilizumab, Vorsetuzumab mafodotin, Votumumab, Zalutumumab, Zanolimumab, Zatuximab, Ziralimumab, Zolimomab aritox, and the like.

In some cases, the intracellular domain of an engineered receptor as described herein induces production of a neuropeptide in a cell that expresses the engineered polypeptide, upon release of the intracellular domain by way of γ-secretase cleavage. Examples of such neuropeptides include, but are not limited to, N-Acetylaspartylglutamic acid, agouti-related peptide, alpha-endorphin, big dynorphin, bombesin, bombesin-like peptides, carbetocin, cocaine-and-amphetamine regulated transcript (CART), cholecystokinin, corazonin, corticotropin-like intermediate peptide, cortistatin, demoxytocin, dynorphin A, dynorphin B, eledoisin, enkephalin, galanin, galanin-like peptide, galmic, galnon, gamma-endorphin, ghrelin, hemopressin, kisspeptin, neurokinin B, neuromedin B, neuromedin N, neuromedin S, neuromedin U, neuromedin S, neuromedin Y, neuropeptide Y, neurotensin, nociceptin, opiorphin, orexin, orexin-A, oxytocin, physalaemin, preprotachykinin, proctolin, proenkephalin, poopiomelanocortin, protein episteme, relaxin-3, somatostatin, substance P, TAC1, tachykinin peptides, vasopressin, and vasotocin.

In some cases, the intracellular domain as described herein and upon release induces production of a transcriptional regulator (e.g., a transcription factor; a transcription inducer; a transcription repressor) in a cell that expresses the engineered receptor. Examples of transcriptional regulators include, e.g., ABT1, ACYP2, AEBP1, AEBP2, AES, AFF1, AFF3, AHR, ANK1, ANK2, ANKFY1, ANKIB1, ANKRD1, ANKRD10, ANKRD2, ANKRD32, ANKRD46, ANKRD49, ANKRD56, ANKRD57, ANKS4B, AR, ARHGAP17, ARID1A, ARID1B, ARID3A, ARID4A, ARID5B, ARNT, ARNT2, ARNTL, ARNTL2, ARX, ASB10, ASB11, ASB12, ASB15, ASB2, ASB5, ASB8, ASB9, ASH1L, ASH2L, ASXL1, ASZ1, ATF1, ATF3, ATF4, ATF4, ATF5, ATF6, ATF7, ATF7IP, ATM, ATOH1, ATXN3, 1300003B13RIK, B3GAT3, B930041F14RIK, BACH1, BACH2, BARX1, BARX2, BATF, BATF2, BATF3, BAZ2A, BBX, BC003267, BCL11A, BCL11B, BCL3, BCL6, BCL6B, BCLAF1, BCOR, BHLHA15, BHLHE40, BHLHE41, BLZF1, BMYC, BNC1, BNC2, BPNT1, BRCA1, BRWD1, BTBD11, BTF3, 6030408C04RIK, CAMK4, CARHSP1, CARM1, CBX4, CBX7, CCNC, CCNH, CCNT1, CCNT2, CDC5L, CDK2, CDK4, CDK9, CDKN2C, CDX1, CDX1, CDX2, CEBPA, CEBPB, CEBPD, CEBPG, CEBPG, CEBPZ, CHD4, CHD7, CHGB, CIC, CIITA, CITED1, CITED2, CITED4, CLOCK, CLPB, CML3, CNOT7, COPS2, CREB1, CREB3, CREB3L1, CREB3L1, CREB3L2, CREB3L3, CREB5, CREBBP, CREBL2, CREM, CSDA, CSDA, CSDC2, CSDE1, CTBP2, CTCF, CTCFL, CTNNB1, CTNNBL1, CXXC1, D11BWG0517E, 2300002D11RIK, DACH1, DAXX, DBP, DDIT3, DDX20, DDX54, DDX58, DEAF1, DEK, DIDO1, DLX2, DMRT1, DMRT2, DMRTB1, DNMT1, DNMT3A, DR1, DRG1, DUSP26, DYSFIP1, E2F1, E2F2, E2F3, E2F5, E2F6, EBF1, EBF2, EBF3, EBF3, EED, EGR1, EGR2, EGR3, EHF, EHMT2, EID2, ELAVL2, ELF1, ELF1, ELF2, ELF3, ELF4, ELF5, ELK3, ELK4, ELL2, EMX2, EMX2, EN2, ENPP2, EOMES, EP300, EPAS1, ERF, ERG, ESR1, ESRRA, ESRRB, ESRRG, ETS1, ETS2, ETV1, ETV3, ETV4, ETV5, ETV6, EVIl, EWSR1, EZH1, EZH2, FAH, FBXL10, FBXL11, FBXW7, FEM1A, FEM1B, FEM1C, FHL2, FLIl, FMNL2, FOS, FOSB, FOSL1, FOSL2, FOXA1, FOXA2, FOXA3, FOXC1, FOXD1, FOXD2, FOXD3, FOXF1, FOXF1A, FOXF2, FOXG1, FOXI1, FOXJ2, FOXJ3, FOXK1, FOXK2, FOXL1, FOXL2, FOXM1, FOXN1, FOXN2, FOXN3, FOXO1, FOXO3, FOXP1, FOXP2, FOXP3, FOXP4, FOXQ1, FUS, FUSIP1, 2810021G02RIK, GABPA, GABPB1, GARNL1, GAS7, GATA1, GATA2, GATA3, GATA4, GATA5, GATA5, GATA6, GBX2, GCDH, GCM1, GFI1, GFI1B, GLI2, GLI3, GLIS1, GLIS2, GLIS3, GLS2, GMEB1, GMEB2, GRHL1, GRHL2, GRHL3, GRLF1, GTF2A1, GTF2B, GTF2E2, GTF2F1, GTF2F2, GTF2H2, GTF2H4, GTF2I, GTF2IRD1, GTF2IRD1, GZF1, HAND2, HBP1, HCLS1, HDAC10, HDAC11, HDAC2, HDAC5, HDAC9, HELZ, HES1, HES4, HES5, HES6, HEXIM1, HEY2, HEYL, HHEX, HHEX, HIC1, HIC2, HIF1A, HIF1AN, HIPK2, HIVEP1, HIVEP2, HIVEP2, HIVEP3, HLF, HLTF, HLX, HMBOX1, HMG20A, HMGA2, HMGB2, HMGB3, HNF1B, HNF4A, HNF4G, HOMEZ, HOXA10, HOXA11, HOXA13, HOXA2, HOXA3, HOXA4, HOXA5, HOXA6, HOXA7, HOXA9, HOXB1, HOXB2, HOXB3, HOXB4, HOXB6, HOXB7, HOXB8, HOXB9, HOXC10, HOXC10, HOXC11, HOXC5, HOXC6, HOXC8, HOXC9, HOXD8, HOXD9, HR, HSBP1, HSF2BP, HTATIP2, HTATSF1, HUWE1, 5830417I10RIK, ID1, ID2, ID3, ID3, IFNAR2, IKBKB, IKBKG, IKZF1, IKZF2, IKZF3, IKZF4, IL31RA, ILF3, ING1, ING2, ING3, ING4, INSM1, INTS12, IQWD1, IRF1, IRF1, IRF2, IRF3, IRF4, IRF5, IRF6, IRF7, IRF8, IRF8, IRX1, IRX2, IRX3, IRX4, IRX5, ISL1, ISL2, ISX, ISX, IVNS1ABP, 2810021J22RIK, JARID1A, JARID1B, JARID1C, JARID1D, JDP2, JUN, JUNB, JUND, KLF1, KLF10, KLF11, KLF12, KLF13, KLF15, KLF16, KLF2, KLF3, KLF3, KLF4, KLF5, KLF6, KLF7, KLF8, KLF9, KRR1, 6330416L07RIK, L3MBTL2, LASS2, LASS4, LASS6, LBA1, LBH, LBX1, LCOR, LDB1, LDB2, LEFT, LHX1, LHX2, LHX5, LIMD1, LIN28, LMO1, LMO4, LMX1A, LSM11, LSM4, LYL1, 9030612M13RIK, 1810007M14RIK, 3632451006RIK, MAF, MAFA, MAFB, MAFF, MAFG, MAFK, MAGEDI, MAP3K12, MAPK1, MAPK3, MAPK8, MAPK8IP1, MAX, MAZ, MBD2, MCM2, MCM4, MCM5, MCM6, MCM1, MECOM, MECP2, MED12, MEDS, MEF2A, MEF2B, MEF2C, MEF2D, MEIS1, MEIS1, MEIS2, MEOX2, MESP2, MIDI, MITF, MKI67IP, MKL1, MLL1, MLL3, MLLT10, MLLT3, MLX, MLXIP, MLXIPL, MNT, MNX1, MPL, MSC, MSRB2, MSX2, MTA3, MTF1, MTF2, MTPN, MXD1, MXD4, MXI1, MYB, MYBBP1A, MYBL2, MYC, MYCBP, MYCL1, MYCN, MYEF2, MYF6, MYNN, MYOCD, MYOD1, MYOG, MYST3, MYST4, MYT1L, MZF1, NAB1, NAB2, NANOG, NARG1, NCOA1, NCOA2, NCOA3, NCOR1, NCOR2, NDN, NEUROD1, NEUROD4, NEUROD6, NEUROG1, NEUROG2, NFAT5, NFATC1, NFATC2, NFATC2IP, NFATC3, NFATC3, NFATC4, NFE2, NFE2L1, NFE2L2, NFIA, NFIA, NFIB, NFIC, NFIL3, NFIX, NFKB1, NFKB2, NFKBIB, NFKBIE, NFKBIZ, NFX1, NFXL1, NFYA, NFYB, NHLH1, NKX2-2, NKX2-3, NKX2-5, NKX2-6, NKX6-2, NMI, NOTCHI, NOTCH2, NOTCH3, NOTCH4, NPAS1, NPAS2, NPAS3, NROB1, NROB2, NR1D1, NR1D2, NR1H3, NR1H4, NR1I2, NR1I3, NR2C1, NR2C2, NR2E3, NR2F1, NR2F2, NR2F6, NR3C1, NR3C2, NR4A1, NR4A2, NR4A2, NR4A3, NR5A1, NR5A2, NRARP, NRIP1, NRIP2, NSBP1, NSD1, NUDT12, NULL, NUPR1, 1700065013RIK, OLIG1, OLIG2, OLIG2, ONECUT1, ONECUT2, ONECUT3, ORC2L, OSGIN1, OSR1, OSR2, OSTF1, OVOL1, OVOL2, PAPOLA, PAPOLG, PAPPA2, PATZ1, PAWR, PAX2, PAX5, PAX6, PAX7, PAX8, PAX9, PBX1, PBX2, PBX3, PBX4, PCBD1, PCGF6, PDCD11, PDLIM4, PDX1, PEG3, PER1, PFDN1, PGR, PHF1, PHF10, PHF12, PHF13, PHF14, PHF20, PHF21A, PHF5A, PHF7, PHOX2A, PHOX2B, PIAS2, PIR, PITX1, PITX2, PKNOX1, PKNOX2, PLA2G6, PLAGLI, PLAGL2, PLRG1, PML, POGK, POLR2B, POLR2E, POLR2H, POLR3E, POLR3H, POLRMT, POU1F1, POU2AF1, POU2F1, POU2F2, POU3F2, POU3F3, POU3F3, POUSF1, POU6F1, PPARA, PPARD, PPARG, PPARGC1A, PPARGC1B, PPP1R12C, PPP1R13B, PPP1R16B, PPP1R1B, PPP2R1A, PPP3CB, PQBP1, PRDM1, PRDM14, PRDM15, PRDM16, PRDM2, PRDM4, PRDM5, PRDM6, PRDM8, PREB, PRKAR1A, PRKCBP1, PROX1, PRRX1, PRRX2, PSMC5, PSMD10, PSMD9, PTF1A, PTGES2, PURB, PWP1, RAB11A, RAB11B, RAB15, RAB18, RAB1B, RAB25, RAB8A, RAB8B, RAI14, RARA, RARB, RARG, RASSF7, RB1, RBBP7, RBL1, RBM14, RBM39, RBM9, RBPJ, RBPJL, RCOR2, REL, RELA, RELB, RERE, REST, REXO4, RFC1, RFX1, RFX2, RFX3, RFX5, RFX7, RFX8, RHOX5, RHOX6, RHOX9, RIPK4, RNF12, RNF14, RNF141, RNF38, RNF4, RORA, RORA, RORB, RORC, RPS6KA4, RREB1, RSRC1, RUNX1, RUNX1T1, RUNX2, RUNX2, RUNX3, RUVBL1, RUVBL2, RXRA, RXRG, RYBP, SAFB2, SALL1, SALL1, SALL2, SALL4, SAP30, SAP30BP, SATB1, SATB2, SATB2, SCANDI, SCAP, SCRT2, SEC14L2, SERTADI, SF1, SFPI1, SFRS5, SH3D19, SH3PXD2B, SHANK3, SHOX2, SHPRH, SIN3A, SIN3B, SIRT2, SIRT3, SIRT5, SIX1, SIX1, SIX2, SIX3, SIX4, SIX5, SKI, SMAD1, SMAD2, SMAD3, SMAD7, SMARCA1, SMARCA2, SMARCA5, SMARCB1, SMYD1, SNAI1, SNAI2, SNAPC2, SNAPC4, SNIP1, SOLH, SOX1, SOX10, SOX11, SOX12, SOX13, SOX15, SOX17, SOX18, SOX2, SOX21, SOX4, SOX5, SOX6, SOX7, SOX8, SOX9, SP1, SP 110, SP140L, SP2, SP3, SP4, SP6, SP8, SPDEF, SPEN, SPIT, SPIB, SQSTM1, SREBF1, SREBF2, SREBF2, SRF, SSBP2, SSBP3, SSBP4, SSRP1, ST18, STAG1, STAT1, STAT1, STAT2, STAT3, STAT4, STAT5A, STAT5B, STAT5B, STATE, SUB1, SUZ12, TADA2L, TAF13, TAF5, TAF5L, TAF7, TAF9, TALI, TALI, TARDBP, TBPL1, TBR1, TBX1, TBX10, TBX15, TBX18, TBX2, TBX2, TBX20, TBX21, TBX3, TBX4, TBX5, TBX6, TCEA1, TCEA3, TCEAL1, TCEB3, TCERG1, TCF12, TCF15, TCF19, TCF20, TCF21, TCF21, TCF3, TCF4, TCF7, TCF7L2, TCFAP2A, TCFAP2B, TCFAP2C, TCFCP2L1, TCFE2A, TCFE3, TCFEB, TCFEC, TCFL5, TEAD1, TEAD2, TEAD3, TEAD4, TEF, TFAP2A, TFAP2C, TFCP2L1, TFDP2, TFEB, TFEC, TGFB1l1, TGIF1, TGIF2, TGIF2LX, THRA, THRAP3, THRB, THRSP, TIAL1, TLE1, TLE6, TMEM131, TMPO, TNFAIP3, TOB1, TOX4, TP63, TRERF1, TRIB3, TRIM24, TRIM28, TRIM30, TRIP13, TRIP4, TRIPE, TRP53, TRP53BP1, TRP63, TRPS1, TRPS1, TSC22D1, TSC22D2, TSC22D3, TSC22D4, TSHZ1, TSHZ1, TSHZ3, TTRAP, TUB, TULP4, TWIST1, TWIST2, TYSND1, UBE2W, UBN1, UBP1, UBTF, UGP2, UHRF1, UHRF2, UNCX, USF1, USF2, UTF1, VDR, VEZF1, VGLL2, VSX1, WASL, WHSC1, WHSC2, WT1, WWP1, WWTR1, XBP1, YAF2, YY1, ZBED1, ZBED4, ZBTB1, ZBTB10, ZBTB16, ZBTB16, ZBTB17, ZBTB2, ZBTB20, ZBTB22, ZBTB25, ZBTB32, ZBTB38, ZBTB4, ZBTB43, ZBTB45, ZBTB47, ZBTB7A, ZBTB7B, ZBTB7C, ZCCHC8, ZDHHC13, ZDHHC16, ZDHHC21, ZDHHC5, ZDHHC6, ZEB2, ANK2ZEB2, ZFHX2, ZFHX3, ZFHX4, ZFP105, ZFP110, ZFP143, ZFP148, ZFP161, ZFP192, ZFP207, ZFP219, ZFP238, ZFP263, ZFP275, ZFP277, ZFP281, ZFP287, ZFP292, ZFP35, ZFP354C, ZFP36, ZFP36L1, ZFP386, ZFP407, ZFP42, ZFP423, ZFP426, ZFP445, ZFP451, ATF5ZFP451, ZFP467, ZFP52, ZFP57, ZFP592, ZFP593, ZFP597, ZFP612, ZFP637, ZFP64, ZFP647, ZFP748, ZFP810, ZFP9, ZFP91, ZFPM1, ZFPM2, ZFX, ZHX2, ZHX3, ZIC1, ZIC2, ZIC3, ZIC4, ZIC5, ZKSCAN1, ZKSCAN3, ZMYND11, ZNF143, ZNF160, ZNF175, ZNF184, ZNF192, ZNF213, ZNF217, ZNF219, ZNF22, ZNF238, ZNF24, ZNF267, ZNF273, ZNF276, ZNF280D, ZNF281, ZNF292, ZNF311, ZNF331, ZNF335, ZNF337, ZNF33B, ZNF366, ZNF394, ZNF398, ZNF41, ZNF410, ZNF415, ZNF423, ZNF436, ZNF444, ZNF445, ZNF451, ZNF460, ZNF496, ZNF498, ZNF516, ZNF521, ZNF532, ZNF536, ZNF546, ZNF552, ZNF563, ZNF576, ZNF580, ZNF596, ZNF621, ZNF628, ZNF648, ZNF649, ZNF652, ZNF655, ZNF664, ZNF668, ZNF687, ZNF692, ZNF696, ZNF697, ZNF710, ZNF80, ZNF91, ZNF92, ZNRD1, ZSCAN10, ZSCAN16, ZSCAN20, ZSCAN21, ZXDC, and ZZZ3. Additional examples of transcriptional regulators are as described above.

Additional examples of transcriptional regulators as described above include but are not limited to transcription factors having a regulatory role in one or more immune cells (i.e., immune cell regulatory transcription factors). Suitable immune cell regulatory transcription factors include, e.g., 2210012G02Rik, Akap81, Appl2, Arid4b, Arid5b, Ashl1, Atf7, Atm, C430014K11Rik, Chd9, Dmtf1, Fos, Foxo1, Foxp1, Hmbox1, Kdm5b, Klf2, Mga, Mll1, M113, Myst4, Pcgf6, Rev31, Scm14, Scp2, Smarca2, Ssbp2, Suhw4, Tcf7, Tfdp2, Tox, Zbtb20, Zbtb44, Zeb1, Zfm1, Zfp1, Zfp319, Zfp329, Zfp35, Zfp386, Zfp445, Zfp518, Zfp652, Zfp827, Zhx2, Eomes, Arnt1, Bbx, Hbp1, Jun, Mef2d, Mterfd1, Nfat5, Nfe212, Nrld2, Phf21a, Taf4b, Trf, Zbtb25, Zfp326, Zfp451, Zfp58, Zfp672, Egr2, Ikzf2, Tafid, Chracl, Dnajb6, Ap1p2, Batf, Bhlhe40, Fosb, Hist1h1c, Hopx, Ifih1, Ikzf3, Lass4, Lin54, Mxd1, Mxi1, Prdm1, Prf1, Rora, Rpa2, Sap30, Stat2, Stat3, Taf9b, Tbx21, Trps1, Xbp1, Zeb2, Atf3, Cenpcl, Lass6, Rb1, Zbtb41, Crem, Fos12, Gtf2b, Irf7, Maff, Nr4al, Nr4a2, Nr4a3, Obfc2a, Rbl2, Re1, Rybp, Sra1, Tgif1, Tnfaip3, Uhrf2, Zbtb1, Ccdc124, Csda, E2f3, Epas1, H1f0, H2afz, Hif1a, Ikzf5, Irf4, Nsbp1, Pim1, Rfc2, Swap70, Tfb1m, 2610036L11Rik, 5133400G04Rik, Apitd1, Blm, Brca1, Brip1, C1d, C79407, Cenpa, Cfl1, Clspn, Ddx1, Dscc1, E2f7, E2f8, Ercc61, Ezh2, Fen1, Foxm1, Gen1, Gsg2, H2afx, Hdac1, Hdgf, Hells, Hist1h1e, Hist3h2a, Hjurp, Hmgb2, Hmgb3, Irf1, Irfo, Kif22, Kif4, Lig1, Lmo2, Lnp, Mbd4, Mcm2, Mcm3, Mcm4, Mcm5, Mcm6, Mcm7, Myb12, Neil3, Nusap1, Orc61, Pola1, Pola2, Pole, Pole2, Polh, Polr2f, Polr2j, Ppp1r8, Prim2, Psmc3ip, Rad51, Rad51c, Rad541, Rfc3, Rfc4, Rnps1, Rpa1, Smarcc1, Spic, Ssrp1, Taf9, Tfdp1, Tmpo, Topbp1, Trdmt1, Uhrf1, Wdhd1, Whsc1, Zbp1, Zbtb32, Zfp367, Carl, Polg2, Atr, Lef1, Myc, Nucb2, Satb1, Taf1a, Ift57, Apex1, Chd7, Chtf8, Ctnnb1, Etv3, Irf9, Myb, Mybbp1a, Pms2, Preb, Sp110, Stat1, Trp53, Zfp414, App, Cdk9, Ddb1, Hsf2, Lbr, Pa2g4, Rbms1, Rfc1, Rfc5, Tada21, Tex261, Xrcc6, and the like.

In some cases, a transcription factor may be an artificial transcription factor (ATF) including but not limited to e.g., Zinc-finger-based artificial transcription factors (including e.g., those described in Sera T. Adv Drug Deliv Rev. 2009 61(7-8):513-26; Collins et al. Curr Opin Biotechnol. 2003 14(4):371-8; Onori et al. BMC Mol Biol. 2013 14:3 the disclosures of which are incorporated herein by reference in their entirety).

In some cases, the intracellular domain of an engineered receptor as described herein can induce production of an immunoreceptor (e.g., an activating immunoreceptor or an inhibitory immunoreceptor) in a cell upon release of the intracellular domain from the engineered receptor. Examples of such immunoreceptors include activating immunoreceptors. A suitable activating immunoreceptor can comprise an immunoreceptor tyrosine-based activation motif (ITAM). An ITAM motif is YX1X2L/I, where X1 and X2 are independently any amino acid. A suitable immunoreceptor can comprise an ITAM motif-containing portion that is derived from a polypeptide that contains an ITAM motif. For example, a suitable immunoreceptor can comprise an ITAM motif-containing domain from any ITAM motif-containing protein. Thus, a suitable immunoreceptor need not contain the entire sequence of the entire protein from which it is derived. Examples of suitable ITAM motif-containing polypeptides include, but are not limited to: DAP12; FCER1G (Fc epsilon receptor I gamma chain); CD3D (CD3 delta); CD3E (CD3 epsilon); CD3G (CD3 gamma); CD3Z (CD3 zeta); and CD79A (antigen receptor complex-associated protein alpha chain). Further examples of suitable ITAM motif-containing polypeptides are as described above.

In some embodiments, release of the intracellular domain can be used to induce production of a T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.) in a cell that expresses the engineered receptor. In some embodiments, release of the intracellular domain can be used to induce production of a T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.) in a cell that expresses the engineered receptor as described herein.

In some embodiments, release of the intracellular domain can be used to induce production of a co-stimulatory polypeptide in a cell that expresses the engineered receptor as described herein. Non-limiting examples of suitable co-stimulatory polypeptides include, but are not limited to, 4-1BB (CD137), CD28, ICOS, OX-40, BTLA, CD27, CD30, GITR, and HVEM. Further examples of suitable co-stimulatory polypeptides are as described above.

In some embodiments, release of the intracellular domain can be used to induce production of an inhibitory immunoreceptor in a cell that expresses the engineered receptor as described herein. An inhibitory immunoreceptor can comprise an immunoreceptor tyrosine-based inhibition motif (ITIM), an immunoreceptor tyrosine-based switch motif (ITSM), an NpxY motif, or a YXXΦ motif. Suitable inhibitor immunoreceptors include PD1; CTLA4; BTLA; CD160; KRLG-1; 2B4; Lag-3; and Tim-3. See, e.g., Odorizzi and Wherry (2012) J. Immunol. 188:2957; and Baitsch et al. (2012) PLoSOne 7:e30852. Further examples of inhibitory immunoreceptors are as described above.

In some embodiments, release of the intracellular domain can be used to induce production of a recombinase in a cell that expresses the engineered receptor as described herein. Non-limiting examples of recombinases include a Cre recombinase; a Flp recombinase; a Dre recombinase; and the like. A further example of a recombinase is a FLPe recombinase (see, e.g., Akbudak and Srivastava (2011) Mol. Biotechnol. 49:82). A suitable recombinase is a Flpo recombinase. Further examples of recombinases are as described above.

In some embodiments, release of the intracellular domain can be used to induce production of a site-specific nuclease in a cell that expresses the engineered receptor as described herein. Non-limiting examples of site-specific nucleases include, but are not limited to, an RNA-guided DNA binding protein having nuclease activity, e.g., a Cas9 polypeptide; a transcription activator-like effector nuclease (TALEN); Zinc-finger nucleases; and the like. Further examples of site-specific nucleases are as described above.

In some embodiments, release of the intracellular domain can be used to induce production of an apoptosis inducer in a cell that expresses the engineered receptor as described herein. Non-limiting examples of apoptosis inducers are tBID polypeptides. The term "tBID" refers to the C-terminal truncated fragment of the BH3 interacting death agonist (BID) protein which results from the enzymatic cleavage of cytosolic BID (e.g., by active caspase). At an early stage of apoptosis, tBID translocates to the mitochondria and mediates the release of Cyt c therefrom. Non-limiting examples of tBID proteins include human tBID (amino acids 61-195 of the amino acid sequence provided in GenBank Accession No. CAG30275).

In some embodiments, release of the intracellular domain can be used to induce production of a TCR in a cell that expresses an engineered receptor as described herein. The TCR is in some cases specific for an epitope of an antigen. Examples of such antigens include, e.g., tumor antigens; cancer cell-associated antigens; hematological malignancy antigens; solid tumor antigens; cell surface antigens (e.g., cell surface antigens targeted by a T cell receptor (TCR); intracellular antigens; and the like. Examples of hematological malignancy antigens include, e.g., CD19 (as expressed in e.g., B-cells), CD20 (as expressed in e.g., B-cells), CD22 (as expressed in e.g., B-cells), CD30 (as expressed in e.g., B-cells), CD33 (as expressed in e.g., Myeloid cells), CD70 (as expressed in e.g., B-cell/T-cells), CD123 (as expressed in e.g., Myeloid cells), Kappa (as expressed in e.g., B-cells), Lewis Y (as expressed in e.g., Myeloid cells), NKG2D ligands (as expressed in e.g., Myeloid cells), ROR1 (as expressed in e.g., B-cells), SLAMF7/CS1 (as expressed in e.g., myeloma cells, natural killer cells, T cells, and most B-cell types), CD138 (as expressed in e.g., malignant plasma cells in multiple myelomas), CD56 (as expressed in e.g., myeloma cells, neural cells, natural killer cells, T cells, and trabecular osteoblasts) CD38 (as expressed in e.g., B-cell/T-cells) and CD160 (as expressed in e.g., NK cells/T-cells), and the like. Examples of solid tumor antigens include, e.g., B7H3 (as expressed in e.g., Sarcoma, glioma), CAIX (as expressed in e.g., Kidney), CD44 v6/v7 (as expressed in e.g., Cervical), CD171 (as expressed in e.g., Neuroblastoma), CEA (as expressed in e.g., Colon), EGFRvIII (as expressed in e.g., Glioma), EGP2 (as expressed in e.g., Carcinomas), EGP40 (as expressed in e.g., Colon), EphA2 (as expressed in e.g., Glioma, lung), ErbB2(HER2) (as expressed in e.g., Breast, lung, prostate, glioma), ErbB receptor family (as expressed in e.g., Breast, lung, prostate, glioma), ErbB3/4 (as expressed in e.g., Breast, ovarian), HLA-A1/MAGE1 (as expressed in e.g., Melanoma), HLA-A2/NY-ESO-1 (as expressed in e.g., Sarcoma, melanoma), FR-a (as expressed in e.g., Ovarian), FAP1 (as expressed in e.g., Cancer associated fibroblasts), FAR (as expressed in e.g., Rhabdomyosarcoma), GD2 (as expressed in e.g., Neuroblastoma, sarcoma, melanoma), GD3 (as expressed in e.g., Melanoma, lung cancer), HMW-MAA (as expressed in e.g., Melanoma), IL11Ra (as expressed in e.g., Osteosarcoma), IL13Ra2 (as expressed in e.g., Glioma), Lewis Y (as expressed in e.g., Breast/ovarian/pancreatic), Mesothelin (as expressed in e.g., Mesothelioma, breast, pancreas), Muc (as expressed in e.g., Ovarian, breast, prostate), NCAM (as expressed in e.g., Neuroblastoma, colorectal), NKG2D ligands (as expressed in e.g., Ovarian, sarcoma), PSCA (as expressed in e.g., Prostate, pancreatic), PSMA (as expressed in e.g., Prostate), TAG72 (as expressed in e.g., Colon), VEGFR-2 (as expressed in e.g., Tumor vasculature), Axl (as expressed in e.g., Lung cancer), Met (as expressed in e.g., Lung cancer), α5β3 (as expressed in e.g., Tumor vasculature), α5β1 (as expressed in e.g., Tumor vasculature), TRAIL-R1/TRAIL-R2 (as expressed in e.g., Solid tumors (colon, lung, pancreas) and hematological malignancies), RANKL (as expressed in e.g., Prostate cancer and bone metastases), Tenacin (as expressed in e.g., Glioma, epithelial tumors (breast, prostate)), EpCAM (as expressed in e.g., Epithelial tumors (breast, colon, lung)), CEA (as expressed in e.g., Epithelial tumors (breast, colon, lung)), gpA33 (as expressed in e.g., Colorectal carcinoma), Mucins (as expressed in e.g., Epithelial tumors (breast, colon, lung, ovarian)), TAG-72 (as expressed in e.g., Epithelial tumors (breast, colon, lung)), EphA3 (as expressed in e.g., Lung, kidney, melanoma, glioma, hematological malignancies) and IGF1R (as expressed in e.g., Lung, breast, head and neck, prostate, thyroid, glioma). Examples of surface and intracellular antigens include, e.g., Her2 (gene symbol ERBB2), MAGE-A1 (gene symbol MAGEA1), MART-1 (gene symbol MLANA), NY-ESO (gene symbol CTAG1), WT1 (gene symbol WT1), MUC17 and MUC13. Examples of other antigens include, e.g., BCMA (gene symbol TNFRSF17), B7H6 (gene symbol NCR3LG1), CAIX (gene symbol CA9), CD123 (gene symbol IL3RA), CD138 (gene symbol SDC1), CD171 (gene symbol L1CAM), CD19 (gene symbol CD19), CD20 (gene symbol CD20), CD22 (gene symbol CD22), CD30 (gene symbol TNFRSF8), CD33 (gene symbol CD33), CD38 (gene symbol CD38), CD44, splice variants inc 7 and 8 (denoted vX in literature) (gene symbol CD44), CEA, CS1 (gene symbol SLAMF7), EGFRvIII (gene symbol EGFR, viii deletion variant), EGP2, EGP40 (gene symbol EPCAM), Erb family member (gene symbol ERBB1, ERBB2, ERBB3, ERBB4), FAP (gene symbol FAP), fetal acetylcholine receptor (gene symbol AChR), Folate receptor alpha (gene symbol FOLR1), Folate receptor beta (gene symbol FOLR2), GD2, GD3, GPC3 (gene symbol GPC3), Her2/neu (gene symbol ERBB2), IL-13Ra2 (gene symbol IL13RA2), Kappa light chain (gene symbol IGK), Lewis-Y, Mesothelin (gene symbol MSLN), Mucin-1 (gene symbol MUC1), Mucin-16 (gene symbol MUC16), NKG2D ligands, prostate specific membrane antigen (PSMA) (gene symbol FOLH1), prostate stem cell antigen (PSCA) (gene symbol PSCA), receptor tyrosine kinase-like orphan receptor 1 (gene symbol ROR1), and Anaplastic Lymphoma Receptor Tyrosine Kinase (gene symbol ALK).

In some embodiments, release of the intracellular domain can be used to induce production of a MESA polypeptide in a cell that expresses the engineered receptor. The MESA polypeptide in some cases comprises a domain that specifically binds an antigen. Examples of such antigens include, e.g., tumor antigens; cancer cell-associated antigens; hematological malignancy antigens; solid tumor antigens; cell surface antigens (e.g., cell surface antigens targeted by a T cell receptor (TCR); intracellular antigens; and the like. Examples of hematological malignancy antigens include, e.g., CD19 (as expressed in e.g., B-cells), CD20 (as expressed in e.g., B-cells), CD22 (as expressed in e.g., B-cells), CD30 (as expressed in e.g., B-cells), CD33 (as expressed in e.g., Myeloid cells), CD70 (as expressed in e.g., B-cell/T-cells), CD123 (as expressed in e.g., Myeloid cells), Kappa (as expressed in e.g., B-cells), Lewis Y (as expressed in e.g., Myeloid cells), NKG2D ligands (as expressed in e.g., Myeloid cells), ROR1 (as expressed in e.g., B-cells), SLAMF7/CS1 (as expressed in e.g., myeloma cells, natural killer cells, T cells, and most B-cell types), CD138 (as expressed in e.g., malignant plasma cells in multiple myelomas), CD56 (as expressed in e.g., myeloma cells, neural cells, natural killer cells, T cells, and trabecular osteoblasts)

CD38 (as expressed in e.g., B-cell/T-cells) and CD160 (as expressed in e.g., NK cells/T-cells), and the like. Examples of solid tumor antigens include, e.g., B7H3 (as expressed in e.g., Sarcoma, glioma), CAIX (as expressed in e.g., Kidney), CD44 v6/v7 (as expressed in e.g., Cervical), CD171 (as expressed in e.g., Neuroblastoma), CEA (as expressed in e.g., Colon), EGFRvIII (as expressed in e.g., Glioma), EGP2 (as expressed in e.g., Carcinomas), EGP40 (as expressed in e.g., Colon), EphA2 (as expressed in e.g., Glioma, lung), ErbB2(HER2) (as expressed in e.g., Breast, lung, prostate, glioma), ErbB receptor family (as expressed in e.g., Breast, lung, prostate, glioma), ErbB3/4 (as expressed in e.g., Breast, ovarian), HLA-A1/MAGE1 (as expressed in e.g., Melanoma), HLA-A2/NY-ESO-1 (as expressed in e.g., Sarcoma, melanoma), FR-a (as expressed in e.g., Ovarian), FAP1 (as expressed in e.g., Cancer associated fibroblasts), FAR (as expressed in e.g., Rhabdomyosarcoma), GD2 (as expressed in e.g., Neuroblastoma, sarcoma, melanoma), GD3 (as expressed in e.g., Melanoma, lung cancer), HMW-MAA (as expressed in e.g., Melanoma), IL11Ra (as expressed in e.g., Osteosarcoma), IL13Ra2 (as expressed in e.g., Glioma), Lewis Y (as expressed in e.g., Breast/ovarian/pancreatic), Mesothelin (as expressed in e.g., Mesothelioma, breast, pancreas), Muc (as expressed in e.g., Ovarian, breast, prostate), NCAM (as expressed in e.g., Neuroblastoma, colorectal), NKG2D ligands (as expressed in e.g., Ovarian, sarcoma), PSCA (as expressed in e.g., Prostate, pancreatic), PSMA (as expressed in e.g., Prostate), TAG72 (as expressed in e.g., Colon), VEGFR-2 (as expressed in e.g., Tumor vasculature), Axl (as expressed in e.g., Lung cancer), Met (as expressed in e.g., Lung cancer), α5β3 (as expressed in e.g., Tumor vasculature), α5β1 (as expressed in e.g., Tumor vasculature), TRAIL-R1/TRAIL-R2 (as expressed in e.g., Solid tumors (colon, lung, pancreas) and hematological malignancies), RANKL (as expressed in e.g., Prostate cancer and bone metastases), Tenacin (as expressed in e.g., Glioma, epithelial tumors (breast, prostate)), EpCAM (as expressed in e.g., Epithelial tumors (breast, colon, lung)), CEA (as expressed in e.g., Epithelial tumors (breast, colon, lung)), gpA33 (as expressed in e.g., Colorectal carcinoma), Mucins (as expressed in e.g., Epithelial tumors (breast, colon, lung, ovarian)), TAG-72 (as expressed in e.g., Epithelial tumors (breast, colon, lung)), EphA3 (as expressed in e.g., Lung, kidney, melanoma, glioma, hematological malignancies) and IGF1R (as expressed in e.g., Lung, breast, head and neck, prostate, thyroid, glioma). Examples of surface and intracellular antigens include, e.g., Her2 (gene symbol ERBB2), MAGE-A1 (gene symbol MAGEA1), MART-1 (gene symbol MLANA), NY-ESO (gene symbol CTAG1), WT1 (gene symbol WT1), MUC17 and MUC13. Examples of other antigens include, e.g., BCMA (gene symbol TNFRSF17), B7H6 (gene symbol NCR3LG1), CAIX (gene symbol CA9), CD123 (gene symbol IL3RA), CD138 (gene symbol SDC1), CD171 (gene symbol L1CAM), CD19 (gene symbol CD19), CD20 (gene symbol CD20), CD22 (gene symbol CD22), CD30 (gene symbol TNFRSF8), CD33 (gene symbol CD33), CD38 (gene symbol CD38), CD44, splice variants incl 7 and 8 (denoted vX in literature) (gene symbol CD44), CEA, CS1 (gene symbol SLAMF7), EGFRvIII (gene symbol EGFR, vIII deletion variant), EGP2, EGP40 (gene symbol EPCAM), Erb family member (gene symbol ERBB1, ERBB2, ERBB3, ERBB4), FAP (gene symbol FAP), fetal acetylcholine receptor (gene symbol AChR), Folate receptor alpha (gene symbol FOLR1), Folate receptor beta (gene symbol FOLR2), GD2, GD3, GPC3 (gene symbol GPC3), Her2/neu (gene symbol ERBB2), IL-13Ra2 (gene symbol IL13RA2), Kappa light chain (gene symbol IGK), Lewis-Y, Mesothelin (gene symbol MSLN), Mucin-1 (gene symbol MUC1), Mucin-16 (gene symbol MUC16), NKG2D ligands, prostate specific membrane antigen (PSMA) (gene symbol FOLH1), prostate stem cell antigen (PSCA) (gene symbol PSCA), receptor tyrosine kinase-like orphan receptor 1 (gene symbol ROR1), and Anaplastic Lymphoma Receptor Tyrosine Kinase (gene symbol ALK).

In some embodiments, release of the intracellular domain can be used to induce production of a CAR in a cell that expresses the engineered receptor as described herein. The CAR in some cases comprises a domain that specifically binds an antigen. Examples of such antigens include, e.g., tumor antigens; cancer cell-associated antigens; hematological malignancy antigens; solid tumor antigens; cell surface antigens (e.g., cell surface antigens targeted by a T cell receptor (TCR); intracellular antigens; and the like. Examples of hematological malignancy antigens include, e.g., CD19 (as expressed in e.g., B-cells), CD20 (as expressed in e.g., B-cells), CD22 (as expressed in e.g., B-cells), CD30 (as expressed in e.g., B-cells), CD33 (as expressed in e.g., Myeloid cells), CD70 (as expressed in e.g., B-cell/T-cells), CD123 (as expressed in e.g., Myeloid cells), Kappa (as expressed in e.g., B-cells), Lewis Y (as expressed in e.g., Myeloid cells), NKG2D ligands (as expressed in e.g., Myeloid cells), ROR1 (as expressed in e.g., B-cells), SLAMF7/CS1 (as expressed in e.g., myeloma cells, natural killer cells, T cells, and most B-cell types), CD138 (as expressed in e.g., malignant plasma cells in multiple myelomas), CD56 (as expressed in e.g., myeloma cells, neural cells, natural killer cells, T cells, and trabecular osteoblasts) CD38 (as expressed in e.g., B-cell/T-cells) and CD160 (as expressed in e.g., NK cells/T-cells), and the like. Examples of solid tumor antigens include, e.g., B7H3 (as expressed in e.g., Sarcoma, glioma), CAIX (as expressed in e.g., Kidney), CD44 v6/v7 (as expressed in e.g., Cervical), CD171 (as expressed in e.g., Neuroblastoma), CEA (as expressed in e.g., Colon), EGFRvIII (as expressed in e.g., Glioma), EGP2 (as expressed in e.g., Carcinomas), EGP40 (as expressed in e.g., Colon), EphA2 (as expressed in e.g., Glioma, lung), ErbB2(HER2) (as expressed in e.g., Breast, lung, prostate, glioma), ErbB receptor family (as expressed in e.g., Breast, lung, prostate, glioma), ErbB3/4 (as expressed in e.g., Breast, ovarian), HLA-A1/MAGE1 (as expressed in e.g., Melanoma), HLA-A2/NY-ESO-1 (as expressed in e.g., Sarcoma, melanoma), FR-a (as expressed in e.g., Ovarian), FAP1 (as expressed in e.g., Cancer associated fibroblasts), FAR (as expressed in e.g., Rhabdomyosarcoma), GD2 (as expressed in e.g., Neuroblastoma, sarcoma, melanoma), GD3 (as expressed in e.g., Melanoma, lung cancer), HMW-MAA (as expressed in e.g., Melanoma), IL11Ra (as expressed in e.g., Osteosarcoma), IL13Ra2 (as expressed in e.g., Glioma), Lewis Y (as expressed in e.g., Breast/ovarian/pancreatic), Mesothelin (as expressed in e.g., Mesothelioma, breast, pancreas), Muc (as expressed in e.g., Ovarian, breast, prostate), NCAM (as expressed in e.g., Neuroblastoma, colorectal), NKG2D ligands (as expressed in e.g., Ovarian, sarcoma), PSCA (as expressed in e.g., Prostate, pancreatic), PSMA (as expressed in e.g., Prostate), TAG72 (as expressed in e.g., Colon), VEGFR-2 (as expressed in e.g., Tumor vasculature), Axl (as expressed in e.g., Lung cancer), Met (as expressed in e.g., Lung cancer), α5β3 (as expressed in e.g., Tumor vasculature), α5β1 (as expressed in e.g., Tumor vasculature), TRAIL-R1/TRAIL-R2 (as expressed in e.g., Solid tumors (colon, lung, pancreas) and hematological malignancies), RANKL (as expressed in e.g., Prostate cancer and bone metastases), Tenacin (as expressed in e.g., Glioma, epithelial tumors (breast, prostate)), EpCAM (as expressed in e.g., Epithelial tumors (breast, colon, lung)), CEA (as expressed in e.g., Epithelial tumors (breast, colon, lung)), gpA33 (as expressed in e.g., Colorectal carcinoma), Mucins (as expressed in e.g., Epithelial tumors (breast, colon, lung, ovarian)), TAG-72 (as expressed in e.g., Epithelial tumors (breast, colon, lung)), EphA3 (as expressed in e.g., Lung, kidney, melanoma, glioma, hematological malignancies) and IGF1R (as expressed in e.g., Lung, breast, head and neck, prostate, thyroid, glioma). Examples of surface and intracellular antigens include, e.g., Her2 (gene symbol ERBB2), MAGE-A1 (gene symbol MAGEA1), MART-1 (gene symbol MLANA), NY-ESO (gene symbol CTAG1), WT1 (gene symbol WT1), MUC17 and MUC13. Examples of other antigens include, e.g., BCMA (gene symbol TNFRSF17), B7H6 (gene symbol NCR3LG1), CAIX (gene symbol CA9), CD123 (gene symbol IL3RA), CD138 (gene symbol SDC1), CD171 (gene symbol L1CAM), CD19 (gene symbol CD19), CD20 (gene symbol CD20), CD22 (gene symbol CD22), CD30 (gene symbol TNFRSF8), CD33 (gene symbol CD33), CD38 (gene symbol CD38), CD44, splice variants inc 7 and 8 (denoted vX in literature) (gene symbol CD44), CEA, CS1 (gene symbol SLAMF7), EGFRvIII (gene symbol EGFR, viii deletion variant), EGP2, EGP40 (gene symbol EPCAM), Erb family member (gene symbol ERBB1, ERBB2, ERBB3, ERBB4), FAP (gene symbol FAP), fetal acetylcholine receptor (gene symbol AChR), Folate receptor alpha (gene symbol FOLR1), Folate receptor beta (gene symbol FOLR2), GD2, GD3, GPC3 (gene symbol GPC3), Her2/neu (gene symbol ERBB2), IL-13Ra2 (gene symbol IL13RA2), Kappa light chain (gene symbol IGK), Lewis-Y, Mesothelin (gene symbol MSLN), Mucin-1 (gene symbol MUC1), Mucin-16 (gene symbol MUC16), NKG2D ligands, prostate specific membrane antigen (PSMA) (gene symbol FOLH1), prostate stem cell antigen (PSCA) (gene symbol PSCA), receptor tyrosine kinase-like orphan receptor 1 (gene symbol ROR1), and Anaplastic Lymphoma Receptor Tyrosine Kinase (gene symbol ALK).

In some embodiments, release of the intracellular domain can be used to induce production of a TANGO polypeptide in a cell that expresses engineered receptor as described herein.

As the release of an intracellular domain from an engineered receptor as described herein can be used to induce the expression of various polypeptides as described herein, in some instances, induced expression of two or more polypeptides may generate a logic gated circuit. Such logic gated circuits can include, but are not limited to, e.g., "AND gates", "OR gates", "NOT gates" and combinations thereof including e.g., higher order gates including e.g., higher order AND gates, higher order OR gates, higher order NOT gates, higher order combined gates (i.e., gates using some combination of AND, OR and/or NOT gates).

"AND" gates as described herein include where two or more inputs are required for propagation of a signal. For example, in some instances, an AND gate allows signaling through two or more engineered receptors or portions thereof where two inputs, e.g., two ligands, are required for signaling through the two or more engineered receptors or portions thereof.

"OR" gates as described herein include where either of two or more inputs may allow for the propagation of a signal. For example, in some instances, an OR gate allows signaling through two or more engineered receptor or portions thereof where any one input, e.g., either of two ligands, may induce the signaling output of the two or more engineered receptors or portions thereof.

"NOT" gates as described herein include where an input is capable of preventing the propagation of a signal. For example, in some instances, a NOT gate inhibits signaling through a given engineered receptor. In one embodiment, a NOT gate may include the inhibition of a binding interaction. For example, a NOT gate may include functional inhibition of an element of a circuit. That is, an inhibitor that functionally prevents signaling through an engineered receptor or the outcome of signaling through such an engineered receptor may serve as a NOT gate of a molecular circuit as described herein. As one example, an inhibitor domain, e.g., an inhibitory PD-1 domain, may serve as a NOT gate to prevent signaling through an engineered receptor, e.g., that results in cell activation.

Multi-input gates can make use of a NOT gate in various different ways to prevent signaling through some other component of a circuit or turn off a cellular response when and/or where a signal activating the NOT gate (e.g., a particular negative antigen) is present. For example, an AND+NOT gate can include an engineered receptor that positively influences a particular cellular activity in the presence of a first antigen and a second engineered receptor that negatively influences the cellular activity in the presence of a second antigen.

Additional Sequences

An engineered receptor as described herein can further include one or more additional polypeptides, where suitable additional polypeptides include, but are not limited to, a signal sequence; an epitope tag; an affinity domain; a nuclear localization signal (NLS); and a polypeptide that produces a detectable signal.

The engineered receptor constructs described herein can further comprise one or more affinity domains useful for identification and/or purification. For example, such affinity domains can bind to a binding partner immobilized on a solid support. Multiple consecutive single amino acids, such as histidine, when fused to an engineered receptor polypeptide construct as descried herein, can be used for one-step purification of the recombinant chimeric polypeptide by high affinity binding to a resin column, such as nickel sepharose. Exemplary affinity domains include His5 (HHHHH) (SEQ ID NO: 33), Hisλ6 (HHFH4HH) (SEQ ID NO: 34), C-myc (EQKLISEEDL) (SEQ ID NO: 35), Flag (DYKDDDDK) (SEQ ID NO: 36), StrepTag (WSHPQFEK) (SEQ ID NO: 37), hemagglutinin, e.g., HA Tag (YPYDVPDYA) (SEQ ID NO: 38), GST, thioredoxin, cellulose binding domain, RYIRS (SEQ ID NO: 39), Phe-His-His-Thr (SEQ ID NO: 40), chitin binding domain, S-peptide, T7 peptide, SH2 domain, C-end RNA tag, WEAAAREACCRECCARA (SEQ ID NO: 41), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100 proteins, parvalbumin, calbindin D9K, calbindin D28K, and calretinin, inteins, biotin, streptavidin, MyoD, Id, leucine zipper sequences, and maltose binding protein.

Nucleic Acids

Provided herein are nucleic acid constructs or sequences that encode an engineered receptor polypeptide construct as described herein. In some cases, a nucleic acid comprising a nucleotide sequence encoding an engineered receptor polypeptide construct as described herein is contained within an expression vector.

In some embodiments, the nucleotide sequence encoding an engineered receptor polypeptide construct as described herein is operably linked to a transcriptional control element (e.g., a promoter; an enhancer; etc.). In some embodiments, the transcriptional control element is inducible. In one embodiment, the transcriptional control element is constitutive. In other embodiments, the promoters are functional in eukaryotic cells. In some embodiments, the promoters are cell type-specific promoters. In some cases, the promoters are tissue-specific promoters.

Depending on the host/vector system utilized, any of a number of suitable transcription and translation control elements, including constitutive and inducible promoters, transcription enhancer elements, transcription terminators, etc. may be used in the expression vector (see e.g., Bitter et al. (1987) Methods in Enzymology, 153:516-544).

A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular temperature, compound, or protein.), it may be a spatially restricted promoter (i.e., transcriptional control element, enhancer, etc.)(e.g., tissue specific promoter, cell type specific promoter, etc.), and it may be a temporally restricted promoter (i.e., the promoter is in the "ON" state or "OFF" state during specific stages of embryonic development or during specific stages of a biological process, e.g., hair follicle cycle in mice).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Inducible promoters suitable for use include any inducible promoter described herein or known to one of ordinary skill in the art. Examples of inducible promoters include, without limitation, chemically/biochemically-regulated and physically-regulated promoters such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a CD8 cell-specific promoter, a CD4 cell-specific promoter, a neutrophil-specific promoter, or an NK-specific promoter. For example, a CD4 gene promoter can be used; see, e.g., Salmon et al. (1993) Proc. Natl. Acad. Sci. USA 90: 7739; and Marodon et al. (2003) Blood 101:3416. As another example, a CD8 gene promoter can be used. NK cell-specific expression can be achieved by use of an Ncr1 (p46) promoter; see, e.g., Eckelhart et al. (2011) Blood 117:1565.

In some cases, the promoter is a cardiomyocyte-specific promoter. In some cases, the promoter is a smooth muscle cell-specific promoter. In some cases, the promoter is a neuron-specific promoter. In some cases, the promoter is an adipocyte-specific promoter. Other cell type-specific promoters are known in the art and are suitable for use herein.

In some cases, a nucleic acid comprising a nucleotide sequence encoding an engineered receptor polypeptide construct as described herein is a recombinant expression vector. In some embodiments, the recombinant expression vector is a viral construct, e.g., a recombinant adeno-associated virus (AAV) construct, a recombinant adenoviral construct, a recombinant lentiviral construct, a recombinant retroviral construct, etc. In some cases, a nucleic acid comprising a nucleotide sequence encoding an engineered receptor polypeptide construct as described herein is a recombinant lentivirus vector. In some cases, a nucleic acid comprising a nucleotide sequence encoding an engineered receptor polypeptide construct as described herein is a recombinant AAV vector.

Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., Hum Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus); and the like. In some cases, the vector is a lentivirus vector. Also suitable are transposon-mediated vectors, such as piggyback and sleeping beauty vectors.

Host Cells

Also provided herein are host cells genetically modified with a nucleic acid encoding an engineered receptor polypeptide construct as described herein, i.e., host cells genetically modified with a nucleic acid comprising a nucleotide sequence encoding an engineered receptor polypeptide construct as described herein. Also provided herein are methods of modulating an activity of a cell that expresses an engineered receptor polypeptide construct as described herein. The method generally involves contacting the cell with a ligand that binds the at least one ligand binding site in the extracellular binding domain or placing the cell in an environment where it can bind to a cellular antigen or soluble ligand. Binding of the ligand to the ligand binding site induces cleavage of the engineered receptor polypeptide construct at the one or more γ-secretase cleavage sites, thereby releasing the intracellular domain. Release of the intracellular domain modulates an activity of the cell.

In some embodiments, the cell is a eukaryotic cell. In some embodiments, the cell is a mammalian cell, an amphibian cell, a reptile cell, an avian cell, or a plant cell.

In some embodiments, the cell is a mammalian cell. In some embodiments, the cell is a human cell. In some embodiments, the cell is a mouse cell. In some embodiments, the cell is rat cell. In some embodiments, the cell is non-human primate cell. In some embodiments, the cell is lagomorph cell. In some cases, the cell is an ungulate cell.

In some embodiments, the cell is an immune cell, e.g., a T cell, a B cell, a macrophage, a dendritic cell, a natural killer cell, a monocyte, etc. In some embodiments, the cell is a T cell. In some embodiments, the cell is a cytotoxic T cell (e.g., a CD8+ T cell). In some embodiments, the cell is a helper T cell (e.g., a CD4+ T cell). In some embodiments, the cell is a regulatory T cell ("Treg"). In some embodiments, the cell is a B cell. In some embodiments, the cell is a macrophage. In some embodiments, the cell is a dendritic cell. In some embodiments, the cell is a peripheral blood mononuclear cell. In some embodiments, the cell is a monocyte. In some embodiments, the cell is a natural killer (NK) cell. In some embodiments, the cell is a CD4+, FOXP3+ Treg cell. In some embodiments, the cell is a CD4+, FOXP3− Treg cell.

In some instances, the cell is obtained from an individual (e.g., autologous or allogeneic to a subject to be treated). For example, in some embodiments, the cell is a primary cell. As another example, the cell is a stem cell or progenitor cell obtained from an individual.

As one non-limiting example, in some embodiments, the cell is an immune cell obtained from an individual. As an example, the cell can be a T lymphocyte obtained from an individual. As another example, the cell is a cytotoxic cell (e.g., a cytotoxic T cell) obtained from an individual. As another example, the cell can be a helper T cell obtained from an individual. As another example, the cell can be a regulatory T cell obtained from an individual. As another example, the cell can be an NK cell obtained from an individual. As another example, the cell can be a macrophage obtained from an individual. As another example, the cell can be a dendritic cell obtained from an individual. As another example, the cell can be a B cell obtained from an individual. As another example, the cell can be a peripheral blood mononuclear cell obtained from an individual.

In some embodiments, the host cell is a somatic cell, e.g. a fibroblast, a hematopoietic cell, a neuron, a pancreatic cell, a muscle cell, a bone cell, a hepatocyte, a pancreatic cell, an epithelial cell, an endothelial cell, a cardiomyocyte, a T cell, a B cell, an osteocyte, and the like.

Provided herein are methods that can be used to modulate an activity of any eukaryotic cell. In some embodiments, the cell is in vivo. In some embodiments, the cell is ex vivo. In some embodiments, the cell is in vitro. Suitable cells include retinal cells (e.g., Muller cells, ganglion cells, amacrine cells, horizontal cells, bipolar cells, and photoreceptor cells including rods and cones, Müller glial cells, and retinal pigmented epithelium); neural cells (e.g., cells of the thalamus, sensory cortex, zona incerta (ZI), ventral tegmental area (VTA), prefrontal cortex (PFC), nucleus accumbens (NAc), amygdala (BLA), substantia nigra, ventral *pallidum*, globus pallidus, dorsal striatum, ventral striatum, subthalamic nucleus, hippocampus, dentate gyrus, cingulate gyrus, entorhinal cortex, olfactory cortex, primary motor cortex, or cerebellum); liver cells; kidney cells; immune cells; cardiac cells; skeletal muscle cells; smooth muscle cells; lung cells; and the like.

Exemplary cells include a stem cell (e.g. an embryonic stem (ES) cell, an induced pluripotent stem (iPS) cell; a germ cell (e.g., an oocyte, a sperm, an oogonia, a spermatogonia, etc.); a somatic cell, e.g. a fibroblast, an oligodendrocyte, a glial cell, a hematopoietic cell, a neuron, a muscle cell, a bone cell, a hepatocyte, a pancreatic cell, etc.

Additional exemplary cells include human embryonic stem cells, fetal cardiomyocytes, myofibroblasts, mesenchymal stem cells, autotransplanted expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multi-potent progenitor cells, unipotent progenitor cells, monocytes, cardiac myoblasts, skeletal myoblasts, macrophages, capillary endothelial cells, xenogenic cells, allogenic cells, and postnatal stem cells.

In some embodiments, the cell is an immune cell, a neuron, an epithelial cell, and endothelial cell, or a stem cell. In some embodiments, the immune cell is a T cell, a B cell, a monocyte, a natural killer cell, a dendritic cell, or a macrophage. In some embodiments, the immune cell is a cytotoxic T cell. In some embodiments, the immune cell is a helper T cell. In some embodiments, the immune cell is a regulatory T cell (Treg).

In some embodiments, the cell is a stem cell. In some embodiments, the cell is an induced pluripotent stem cell. In some embodiments, the cell is a mesenchymal stem cell. In some embodiments, the cell is a hematopoietic stem cell. In some embodiments, the cell is an adult stem cell.

Suitable cells include bronchioalveolar stem cells (BASCs), bulge epithelial stem cells (bESCs), corneal epithelial stem cells (CESCs), cardiac stem cells (CSCs), epidermal neural crest stem cells (eNCSCs), embryonic stem cells (ESCs), endothelial progenitor cells (EPCs), hepatic oval cells (HOCs), hematopoietic stem cells (HSCs), keratinocyte stem cells (KSCs), mesenchymal stem cells (MSCs), neuronal stem cells (NSCs), pancreatic stem cells (PSCs), retinal stem cells (RSCs), and skin-derived precursors (SKPs)

In some embodiments, the stem cell is a hematopoietic stem cell (HSC), and the transcription factor induces differentiation of the HSC to differentiate into a red blood cell, a platelet, a lymphocyte, a monocyte, a neutrophil, a basophil, or an eosinophil. In some embodiments, the stem cell is a mesenchymal stem cell (MSC), and the transcription factor induces differentiation of the MSC into a connective tissue cell such as a cell of the bone, cartilage, smooth muscle, tendon, ligament, stroma, marrow, dermis, or fat.

In some embodiments, the cell is genetically modified to express two different engineered receptor constructs as described herein or alternatively, an engineered receptor construct as described herein in combination with a second expression construct (e.g., a chimeric antigen receptor expression construct).

In some embodiments, the cell is genetically modified to express an engineered receptor polypeptide construct as described herein; and is further genetically modified to express a chimeric antigen receptor (CAR). For example, in some embodiments, the host cell is genetically modified with a nucleic acid comprising a nucleotide sequence encoding a CAR, and the intracellular domain of the chimeric polypeptide is a transcriptional activator. In some embodiments, the nucleotide sequence encoding the CAR is operably linked to a transcriptional control element that is activated by the intracellular domain of the chimeric polypeptide. Many CAR polypeptides have been described in the art, any of which is suitable for use herein.

In some embodiments, the CAR comprises an extracellular domain, a transmembrane region and an intracellular signaling domain; where the extracellular domain comprises a ligand or a receptor linked to an optional support region capable of tethering the extracellular domain to a cell surface, and the intracellular signaling domain comprises the signaling domain from the zeta chain of the human CD3 complex (CD3zeta) and one or more costimulatory signaling domains, such as those from CD28, 4-1BB and OX-40. The extracellular domain contains a recognition element (e.g., an antibody or other target-binding scaffold) that enables the CAR to bind a target. In some embodiments, a CAR comprises the antigen binding domains of an antibody (e.g., an scFv) linked to T-cell signaling domains. In some embodiments, when expressed on the surface of a T cell, the CAR can direct T cell activity to those cells expressing a receptor or ligand for which this recognition element is specific. As an example, a CAR that contains an extracellular domain that contains a recognition element specific for a tumor antigen can direct T cell activity to tumor cells that bear the tumor antigen. The intracellular region enables the cell (e.g., a T cell) to receive costimulatory signals. The costimulatory signaling domains can be selected from CD28, 4-1BB, OX-40 or any combination of these. Exemplary CARs comprise a human CD4 transmembrane region, a human IgG4 Fc and a receptor or ligand that is tumor-specific, such as an IL13 or IL3 molecule.

The extracellular domain is made up of a soluble receptor ligand (that is specific for a target tumor antigen or other tumor cell-surface molecule) linked to an optional support region capable of tethering the extracellular domain to a cell surface. In some embodiments, the CAR is a heterodimeric, conditionally active CAR, as described in WO 2014/127261. In some embodiments, the heterodimeric, conditionally active CAR is activated by: i) binding an antigen for which the CAR is specific; and ii) a dimerizing agent that induces dimerization of the two polypeptide chains of the heterodimeric, conditionally active CAR. The dimerizing agent can be a small molecule, or can be light.

Transgenic Organisms

Also provided herein non-human transgenic organisms that comprise a nucleic acid encoding an engineered receptor polypeptide construct as described herein. A transgenic non-human organism of the present disclosure comprises a genome that has been genetically modified to include a nucleic acid comprising a nucleotide sequence encoding an engineered receptor polypeptide construct as described herein.

Methods of producing genetically modified organisms are known in the art. For example, see Cho et al., Curr Protoc Cell Biol. 2009 March; Chapter 19:Unit 19.11: Generation of transgenic mice; Gama et al., Brain Struct Funct. 2010 March; 214(2-3):91-109. Epub 2009 Nov. 25: Animal transgenesis: an overview; and Husaini et al., GM Crops. 2011 June-December; 2(3):150-62. Epub 2011 June 1: Approaches for gene targeting and targeted gene expression in plants.

In a non-human transgenic organism as described herein, a nucleic acid comprising a nucleotide sequence encoding an engineered receptor polypeptide construct as described herein can be under the control of (i.e., operably linked to) an unknown promoter (e.g., when the nucleic acid randomly integrates into a host cell genome) or can be under the control of (i.e., operably linked to) a known promoter. Suitable known promoters can be any known promoter and include constitutively active promoters (e.g., CMV promoter), inducible promoters (e.g., heat shock promoter, Tetracycline-regulated promoter, Steroid-regulated promoter, Metal-regulated promoter, estrogen receptor-regulated promoter, etc.), spatially restricted and/or temporally restricted promoters (e.g., a tissue specific promoter, a cell type specific promoter, etc.), etc.

A subject genetically modified organism (e.g. an organism whose genome comprises a nucleotide sequence encoding an engineered receptor polypeptide construct as described herein can be any organism including for example, a plant; an invertebrate (e.g., a cnidarian, an echinoderm, a worm, a fly, etc.); a non-mammalian vertebrate (e.g., a fish (e.g., zebrafish, puffer fish, gold fish, etc.)); an amphibian (e.g., salamander, frog, etc.); a reptile; a bird; a mammal; etc.); an ungulate (e.g., a goat, a pig, a sheep, a cow, etc.); a rodent (e.g., a mouse, a rat, a hamster, a guinea pig); a lagomorph (e.g., a rabbit); etc. In some embodiments, the transgenic non-human organism is a mouse. In some embodiments, the transgenic non-human organism is a rat. In some embodiments, the transgenic non-human organism is a plant.

In some embodiments, the transgenic non-human animal is homozygous for the transgene encoding an engineered receptor polypeptide construct as described herein. In some embodiments, the transgenic non-human animal is heterozygous for the transgene encoding an engineered receptor polypeptide construct as described herein.

Methods and Practical Applications

An engineered receptor polypeptide construct as described herein, or a nucleic acid encoding an engineered receptor polypeptide construct as described herein, or a recombinant expression vector comprising a nucleic acid of the present disclosure, are useful in a variety of applications.

Exemplary methods of modulating an activity of a cell that expresses an engineered receptor polypeptide construct as described herein are provided herein. Methods for modulating the activity of a cell can be carried out in vitro, ex vivo, or in vivo. In some embodiments, a method of the present disclosure is carried out in vitro, e.g., in in vitro cell culture, with cells grown as single cells in suspension, with cells grown on a solid support, with cells grown in a 3-dimensional scaffold, and the like. Methods for modulating the activity of a cell can be carried out in a single cell, in a multicellular environment (e.g., a naturally-occurring tissue; an artificial tissue; etc.), a cellular microenvironment (e.g., a tumor microenvironment) or in a solution. Methods of the present disclosure for modulating the activity of a cell can be carried out in parallel or in series.

The present disclosure provides a method of modulating an activity of a cell that expresses an engineered receptor polypeptide construct as described herein. In some embodiments, the method comprises: contacting the cell with a ligand (e.g., antigen, drug, analyte etc.), wherein binding of the ligand to the ligand binding site on the extracellular ligand binding domain relieves the inhibition of γ-secretase inhibition, which in turn induces cleavage of the engineered receptor polypeptide construct at the one or more γ-secretase cleavage sites, thereby releasing the intracellular domain, wherein release of the intracellular domain modulates the activity of the cell. The intracellular domain provides an "effector function," where an effector function can be transcriptional activation; transcriptional repression; translational activation; translational repression; modulation of organelle function; immune cell activation; immune cell repression; induction of apoptosis; repression of apoptosis; nuclease activity; regulation of differentiation; replacement of a target nucleic acid; modification of a target nucleic acid; fluorescence; etc. Activities of a cell that can be modulated using a method of the present disclosure include, but are not limited to, immune cell activation (e.g., T cell activation, etc.); apoptosis; production of effector molecules (e.g., cytokines, antibodies, growth factors, etc.); transcription of a target nucleic acid; translation of a target mRNA; organelle activity; intracellular trafficking; differentiation; RNA interference and the like. The methods of the present disclosure can also be used to cause the release of effectors that act at the plasma membrane, thereby leading to modification of cellular activity (e.g. release of immune co-inhibitory receptor motifs that provide for immune activation). In exemplary embodiments, the engineered receptor polypeptide constructs can be used for expressing recombinases or enzymes for site-specific genomic modification (e.g., Cas9, zinc finger proteases etc.). Additional exemplary activities of the cell that can be modulating using the methods described herein include, but are not limited to, i) expression of a gene product of the cell; ii) proliferation of the cell; iii) apoptosis of the cell; iv) non-apoptotic death of the cell; v) differentiation of the cell; vi) dedifferentiation of the cell; vii) migration of the cell; viii) secretion of a molecule from the cell; ix) cellular adhesion of the cell, and x) RNA interference or RNA mediated control of gene expression (e.g., miRNA, shRNA, siRNA, dsRNA, etc.).

Methods for Controlling Expression of a Gene Product

An engineered receptor polypeptide construct as described herein can be used to control intracellular expression or expression/secretion of biological molecules, such as cytokines, growth factors, chemokines, interleukins, antibodies, intrabodies, agonists, or RNA interference agents that are genetically encoded. In some embodiments, the endogenous gene product of the cell is a chemokine, a chemokine receptor, a cytokine, a cytokine receptor, a differentiation factor, a growth factor, a growth factor receptor, a hormone, a metabolic enzyme, a proliferation inducer, a receptor, a small molecule second messenger synthesis enzyme, a T cell receptor, a transcription activator, a transcription repressor, a transcriptional activator, a transcriptional repressor, a translation regulator, a translational activator, a translational repressor, an activating immunoreceptor, an apoptosis in inhibitor, an apoptosis inducer, an immunoactivator, an immunoinhibitor, or an inhibiting immunoreceptor. In some embodiments, the endogenous gene product is a secreted gene product. In some embodiments, the endogenous gene product is a cell surface gene product. In some embodiments, the endogenous gene product is an intracellular gene product. In some embodiments, the activated intracellular domain simultaneously modulates expression of two or more endogenous gene products in the cell.

In some embodiments, binding of a given ligand or analyte to an engineered receptor polypeptide construct as described herein can be used to sense a particular region, tissue or cell type in the body, which then triggers the localized expression/delivery of the secreted biologic to that site. Control of delivery of the biologic could be via indirect control (control of transcription of the agent), or via control of other processes involved in expression, processing and secretion of the biologic.

In some embodiments, the intracellular effector domain modulates expression of a heterologous gene product in the cell. A heterologous gene product is one that is not normally produced by the cell. For example, the cell can be genetically modified with a nucleic acid comprising a nucleotide sequence encoding the heterologous gene product. In some embodiments, the heterologous gene product is a chemokine, a chemokine receptor, a chimeric antigen receptor, a cytokine, a cytokine receptor, a differentiation factor, a growth factor, a growth factor receptor, a hormone, a metabolic enzyme, a pathogen derived protein, a proliferation inducer, a receptor, a RNA guided nuclease, a site-specific nuclease, a small molecule second messenger synthesis enzyme, a T cell receptor, a toxin derived protein, a transcription activator, a transcription repressor, a transcriptional activator, a transcriptional repressor, a translation regulator, a translational activator, a translational repressor, an activating immunoreceptor, an antibody, an apoptosis in inhibitor, an apoptosis inducer, an engineered T cell receptor, an immunoactivator, an immunoinhibitor, an inhibiting immunoreceptor, an RNA guided DNA binding protein, a synNotch polypeptide, a MESA polypeptide, a TANGO polypeptide, a CAR, a TCR, or a second engineered receptor polypeptide construct. In some embodiments, the heterologous gene product is a secreted gene product. In some embodiments, the heterologous gene product is a cell surface gene product. In some embodiments, the heterologous gene product is an intracellular gene product. In some embodiments, the activated intracellular domain simultaneously modulates expression of two or more heterologous gene products in the cell.

In some embodiments, the intracellular domain, upon release, induces expression of a heterologous gene product in the cell, where the heterologous gene product is a CAR.

In some embodiments, intracellular domain induces expression of a heterologous gene product in the cell, where the heterologous gene product is a MESA polypeptide. A modular extracellular sensor architecture (MESA) polypeptide suitable for use in a method of the present disclosure can be a MESA polypeptide as described in U.S. Patent Publication No. 2014/0234851. A MESA polypeptide comprises: a) a ligand binding domain; b) a transmembrane domain; c) a protease cleavage site; and d) a functional domain. The functional domain can be a transcription regulator (e.g., a transcription activator, a transcription repressor). In some embodiments, a MESA receptor comprises two polypeptide chains. In some embodiments, a MESA receptor comprises a single polypeptide chain.

In some embodiments, the intracellular domain induces expression of a heterologous gene product in the cell, where the heterologous gene product is a TANGO polypeptide. A suitable TANGO polypeptide is a heterodimer in which a first comprises a tobacco etch virus (Tev) protease and a second polypeptide comprises a Tev proteolytic cleavage site (PCS) fused to a transcription factor. When the two polypeptides are in proximity to one another, which proximity is mediated by a native protein-protein interaction, Tev cleaves the PCS to release the transcription factor. Barnea et al. (Proc Natl Acad Sci USA. 2008 Jan. 8; 105(1):64-9).

In some embodiments, the intracellular domain induces expression of a heterologous gene product in the cell, where the heterologous gene product is a T cell receptor (TCR). TCRs that can be induced as described herein include TCR that are specific for any of a variety of epitopes, including, e.g., an epitope on the surface of a cancer cell, an epitope on the surface of a virus-infected cell, an epitope present in an autoantigen, and the like. A TCR generally includes an alpha chain and a beta chain; and recognizes antigen when presented by a major histocompatibility complex. In some embodiments, the TCR is an engineered TCR.

Any engineered TCR having immune cell activation function can be induced using a method of the present disclosure. Such TCRs include, e.g., antigen-specific TCRs, Monoclonal TCRs (MTCRs), Single chain MTCRs, High Affinity CDR2 Mutant TCRs, CD1-binding MTCRs, High Affinity NY-ESO TCRs, VYG HLA-A24 Telomerase TCRs, including e.g., those described in PCT Pub Nos. WO 2003/020763, WO 2004/033685, WO 2004/044004, WO 2005/114215, WO 2006/000830, WO 2008/038002, WO 2008/039818, WO 2004/074322, WO 2005/113595, WO 2006/125962, the contents of each of which are incorporated herein by reference in their entirety; Strommes et al. Immunol Rev. 2014; 257(1):145-64; Schmitt et al. Blood. 2013; 122(3):348-56; Chapuls et al. Sci Transl Med. 2013; 5(174): 174ra27; Thaxton et al. Hum Vaccin Immunother. 2014; 10(11):3313-21 (PMID:25483644); Gschweng et al. Immunol Rev. 2014; 257(1):237-49 (PMID:24329801); Hinrichs et al. Immunol Rev. 2014; 257(1):56-71 (PMID:24329789); Zoete et al. Front Immunol. 2013; 4:268 (PMID:24062738); Marr et al. Clin Exp Immunol. 2012; 167(2):216-25 (PMID: 22235997); Zhang et al. Adv Drug Deliv Rev. 2012; 64(8): 756-62 (PMID:22178904); Chhabra et al. Scientific World Journal. 2011; 11:121-9 (PMID:21218269); Boulter et al. Clin Exp Immunol. 2005; 142(3):454-60 (PMID: 16297157); Sami et al. Protein Eng Des Sel. 2007; 20(8): 397-403; Boulter et al. Protein Eng. 2003; 16(9):707-11; Ashfield et al. IDrugs. 2006; 9(8):554-9; Li et al. Nat Biotechnol. 2005; 23(3):349-54; Dunn et al. Protein Sci. 2006; 15(4):710-21; Liddy et al. Mol Biotechnol. 2010; 45(2); Liddy et al. Nat Med. 2012; 18(6):980-7; Oates, et al. Oncoimmunology. 2013; 2(2):e22891; McCormack, et al. Cancer Immunol Immunother. 2013 April; 62(4):773-85; Bossi et al. Cancer Immunol Immunother. 2014; 63(5):437-48 and Oates, et al. Mol Immunol. 2015 October; 67(2 Pt A):67-74; the disclosures of each of which are incorporated herein by reference in their entirety.

In some embodiments, the intracellular domain induces expression of a heterologous gene product in the cell, where the heterologous gene product is a synNotch polypeptide as described in US2016/0264665; US2017/0233474; US2018/0079812; US2018/0355011; US2021/0107965; US2018/0208636 and U.S. Pat. Nos. 9,670,281; 9,834,608; 10,836,808; 10,822,387; and 10,590,182, the contents of each of which are incorporated herein by reference in their entirety.

Methods for Improved Targeting of a CAR T Cell

Provided herein are methods of modulating an activity of a cell that expresses: i) an engineered receptor polypeptide construct; and b) a chimeric antigen receptor or a nucleic acid encoding a chimeric antigen receptor. In an exemplary method, the engineered receptor polypeptide construct is expressed on the plasma membrane of a T cell that further comprises an inducible nucleic acid vector that encodes a chimeric antigen receptor (CAR). In such embodiments, the intracellular domain comprises an agent that induces transcription or relieves inhibition of transcription from the nucleic acid vector encoding the CAR. This configuration permits the CAR to be expressed only upon targeting to the target cell or cellular microenvironment and is achieved by designing the extracellular ligand binding domain to bind, for example, a cancer cell antigen, or a soluble antigen in a tumor cell microenvironment.

Alternatively, the CAR can be expressed on the plasma membrane in combination with the engineered receptor polypeptide construct and configured such that both receptors must bind their respective ligands before T cell activation can occur. In some embodiments, the intracellular effector domains of each of the receptors are required in order for T cell activation to occur.

In some embodiments, the CAR comprises an extracellular domain, a transmembrane region and an intracellular signaling domain; where the extracellular domain comprises a ligand or a receptor linked to an optional support region capable of tethering the extracellular domain to a cell surface, and the intracellular signaling domain comprises the signaling domain from the zeta chain of the human CD3 complex (CD3zeta) and one or more costimulatory signaling domains, such as those from CD28, 4-1BB and OX-40. The extracellular domain contains a recognition element (e.g., an antibody or other target-binding scaffold) that enables the CAR to bind a target. In some embodiments, a CAR comprises the antigen binding domains of an antibody (e.g., an scFv) linked to T-cell signaling domains. In some embodiments, when expressed on the surface of a T cell, the CAR can direct T cell activity to those cells expressing a receptor or ligand for which this recognition element is specific. As an example, a CAR that contains an extracellular domain that contains a recognition element specific for a tumor antigen can direct T cell activity to tumor cells that bear the tumor antigen. The intracellular region enables the cell (e.g., a T cell) to receive costimulatory signals. The costimulatory signaling domains can be selected from CD28, 4-1BB, OX-40 or any combination of these. Exemplary CARs comprise a human CD4 transmembrane region, a human IgG4 Fc and a receptor or ligand that is tumor-specific, such as an IL13 or IL3 molecule.

The extracellular domain is made up of a soluble receptor ligand (that is specific for a target tumor antigen or other tumor cell-surface molecule) linked to an optional support region capable of tethering the extracellular domain to a cell surface. In some embodiments, the CAR is a heterodimeric, conditionally active CAR, as described in WO 2014/127261.

The term CAR is not limited specifically to CAR molecules but also includes CAR variants. CAR variants include split CARs wherein the extracellular portion (e.g., the ligand binding portion) and the intracellular portion (e.g., the intracellular signaling portion) of a CAR are present on two separate molecules. CAR variants also include ON-switch CARs which are conditionally activatable CARs, e.g., comprising a split CAR wherein conditional hetero-dimerization of the two portions of the split CAR is pharmacologically controlled. CAR variants also include bispecific CARs, which include a secondary CAR binding domain that can either amplify or inhibit the activity of a primary CAR. CAR variants also include inhibitory chimeric antigen receptors (iCARs) which may, e.g., be used as a component of a bispecific CAR system, where binding of a secondary CAR binding domain results in inhibition of primary CAR activation. CAR molecules and derivatives thereof (i.e., CAR variants) are described, e.g., in PCT Application No. US2014/016527; Fedorov et al. Sci Transl Med (2013); 5(215):215ra172; Glienke et al. Front Pharmacol (2015) 6:21; Kakarla & Gottschalk 52 Cancer J (2014) 20(2):151-5; Riddell et al. Cancer J (2014) 20(2):141-4; Pegram et al. Cancer J (2014) 20(2):127-33; Cheadle et al. Immunol Rev (2014) 257(1):91-106; Barrett et al. Annu Rev Med (2014) 65:333-47; Sadelain et al. Cancer Discov (2013) 3(4):388-98; Cartellieri et al., J Biomed Biotechnol (2010) 956304; the disclosures of which are incorporated herein by reference in their entirety.

Split CAR may be extracellularly split or intracellularly split and may or may not be conditionally heterodimerizable. For example, split CAR systems that are not conditionally heterodimerizable may contain a constitutive heterodimerization domain or other binding pair (e.g., a Fc binding pair or other orthogonal binding pair) that does not depend on the presence of one or more additional molecules for the heterodimerization that results in the formation of an active CAR from assembly of the split portions.

In some instances, an extracellularly split CAR may be split extracellularly at the antigen binding domain into two parts including e.g., where the first part of the split CAR contains an extracellular Fc binding domain that specifically binds to second part of the split CAR that contains the antigen recognition domain.

In some instances, an extracellularly split CAR may be split extracellularly at the antigen binding domain into two parts including e.g., where the first part of the split CAR contains an first part of an orthogonal protein binding pair that specifically binds to the second part of the orthogonal protein binding pair that is contained in the second part of the split CAR that contains the antigen recognition domain.

In some instances, an intracellularly split CAR may be split intracellularly proximal to the transmembrane domain into two parts including e.g., where the first part of the split CAR includes the antigen recognition domain, a transmembrane domain and an intracellular first portion of a constitutive heterodimerization domain and the second part of the split CAR includes a transmembrane domain, the second portion of the constitutive heterodimerization domain proximal to the transmembrane domain, one or more co-stimulatory domains and one or more signaling domains (e.g., ITAM domains).

In some instances, an intracellularly split CAR may be split into two parts intracellularly proximal to an intracellular domain or between two intracellular domains including e.g., where the first part of the split CAR includes the antigen recognition domain, a transmembrane domain, one or more co-stimulatory domains and an intracellular first portion of a constitutive heterodimerization domain and the second part of the split CAR includes a transmembrane domain, one or more co-stimulatory domains, one or more signaling domains (e.g., ITAM domains) and the second portion of the constitutive heterodimerization domain between the one or more co-stimulatory domains and the one or more signaling domains.

In some instances, an intracellularly split CAR may be split into two parts intracellularly between intracellular domains including e.g., where the first part of the split CAR includes the antigen recognition domain, a transmembrane domain, one or more co-stimulatory domains and an intracellular first portion of a constitutive heterodimerization domain proximal to the intracellular terminus of the first part of the split CAR and the second part of the split CAR includes a transmembrane domain, one or more signaling domains (e.g., ITAM domains) and the second portion of the constitutive heterodimerization domain between the transmembrane domain and the one or more signaling domains.

An ordinary skilled artisan will be readily aware that arrangements of the domains within first and second parts of a split CAR are not limited to those arrangements specifically described herein. The specific locations at which a single CAR may be split to generate a split CAR may vary provided that the two or more polypeptides that result from such a split or a plurality of splits are functionally capable of forming a functional CAR upon their concurrent presence within a single cell. Such functional activity may be readily determined including e.g., through the use of one or more of the assays described herein.

The engineered receptor polypeptide constructs described herein can also be used to similarly modulate the activity of any other natural, chimeric, or orthogonal receptor whose activity is not constitutively present in the cell, or whose activity is not normally present in the cell, thereby altering the signals the cell responds to.

The invention may be as described in any one of the following numbered paragraphs:

1. An engineered receptor polypeptide construct comprising:
   (i) an extracellular ligand binding domain having at least one ligand binding site,
   (ii) an optional flexible polypeptide linker,
   (iii) an intramolecular peptide that binds to the at least one ligand binding site in the extracellular ligand binding domain,
   (iv) a transmembrane domain comprising at least one γ-secretase cleavage site, and
   (v) an intracellular effector domain,
   wherein when the intramolecular peptide is bound to the at least one ligand binding site, the extracellular ligand binding domain is maintained in a position that sterically inhibits γ-secretase from cleaving the construct at the at least one γ-secretase cleavage site, and
   wherein, in the presence of a cognate ligand, the intramolecular peptide is displaced, thereby releasing the extracellular ligand binding domain to a conformation that permits γ-secretase to cleave the construct at the at least one γ-secretase cleavage site and the intracellular effector domain is released, thereby producing an effect in the cell in which the engineered receptor construct is expressed.

2. The construct of paragraph 1, wherein the optional flexible linker comprises at least 2 amino acids and no more than 300 amino acids.

3. The construct of paragraph 1 or 2, wherein the intramolecular peptide has a lower, equal or greater affinity of binding to the ligand binding site than the cognate ligand.

4. The construct of any one of paragraphs 1-3, wherein the intramolecular peptide does not inhibit gamma-secretase binding when placed at the juxtacrine position of the transmembrane domain.

5. The construct of any one of paragraphs 1-4, wherein the intramolecular peptide is an engineered peptide or a naturally occurring peptide.

6. The construct of any one of paragraphs 1-5, wherein the engineered peptide is derived from phage display, directed evolution, or rational design.

7. The construct of any one of paragraphs 1-6, wherein the intracellular effector domain comprises a transcription factor, a fluorescent protein, a protein marker, an enzyme, an enzyme subdomain, a cytotoxic protein, a dominant negative polypeptide, a nucleic acid, a therapeutic protein or a peptide.

8. The construct of paragraph 7, wherein the nucleic acid comprises an mRNA, an miRNA, an shRNA, an siRNA, a dsRNA, or an antisense nucleotide.

9. The construct of paragraph 7, wherein the fluorescent protein comprises green fluorescence protein (GFP), yellow fluorescence protein (YFP), enhanced GFP (EGFP), enhanced YFP (EYFP), blue fluorescent protein (BFP), superfolder GFP (sfGFP), cyan fluorescent protein (ECFP), FITC, rhodamine, mCherry, mOrange, or mStrawberry.

10. The construct of paragraph 7, wherein the enzyme comprises Cas9, dCas9, a zinc finger protease, a chemiluminescent enzyme, a therapeutic enzyme, a metabolic enzyme, an apoptotic enzyme, or a DNA repair enzyme.

11. The construct of paragraph 7, wherein the cytotoxic protein comprises a pro-apoptotic protein, diphtheria toxin A fragment, botulinum toxin, exotoxin A, ricin A chain, abrin A chain, modeccin A chain, α-sacrin, curcin, crotin, gelonin, mitogillin, restrictocin, phenomycin, neomycin, a *Shigella* toxin, pertussis toxin, CagA, VopQ, or YopH.

12. The construct of paragraph 7, wherein the therapeutic protein comprises replacement of a damaged or missing protein in a given disease or disorder.

13. The construct of any one of paragraphs 1-12, wherein the intracellular effector domain further comprises an intracellular targeting or localization sequence.

14. The construct of any one of paragraphs 1-13, wherein the intracellular targeting or localization sequence comprises a nuclear targeting sequence, a mitochondrial targeting sequence, an endoplasmic reticulum targeting sequence, a peroxisomal targeting sequence, a plasma membrane targeting sequence, a trans-Golgi targeting sequence or a lysosomal targeting sequence.

15. The construct of any one of paragraphs 1-14, wherein the extracellular ligand binding domain further comprises at least a second ligand binding site that does not bind the intramolecular peptide and binding of the ligand to this site does not induce cleavage of the intracellular effector domain,
wherein when a ligand binds to the second ligand binding sites, the overall conformation is such that it is easier for a ligand to displace the intramolecular peptide from the first ligand binding site than if the ligand is not bound to the second ligand binding site, or
wherein binding of a ligand to the second ligand binding sites increases the avidity of the ligand to the first ligand binding site and increases the length of time that the ligand binds by altering the dynamic equilibrium kinetics.

16. The construct of any one of paragraphs 1-15, wherein the transmembrane domain comprises a Notch receptor transmembrane domain.

17. The construct of any one of paragraphs 1-16, wherein the extracellular ligand binding domain comprises a receptor binding domain, an antibody binding domain, a single-chain variable fragments (scFv), a nanobody, a naturally occurring protein binding domain, a peptide, or a rationally designed protein with ligand affinity.

18. The construct of any one of paragraphs 1-17, wherein the cognate ligand is soluble or tethered.

19. The construct of paragraph 18, wherein the cognate ligand is an antigen, a drug, an analyte, a protein, a peptide, a nucleic acid, a glycoprotein, a small molecule, a carbohydrate, a lipid, a glycolipid, a lipoprotein, or a lipopolysaccharide.

20. A nucleic acid sequence encoding the engineered receptor polypeptide construct of any one of paragraphs 1-19.

21. A cell expressing the engineered receptor polypeptide construct of any one of paragraphs 1-19.

22. The cell of paragraph 21, wherein the cell is a human cell.

23. The cell of paragraph 21 or 22, wherein the cell is a therapeutic cell.

24. The cell of paragraph 23, wherein the cell is a chimeric antigen receptor T cell (CAR T cell), an embryonic stem cell, an induced pluripotent stem cell, a progenitor cell, or a differentiated cell.

25. The cell of paragraph 21, wherein the cell is a bacterial cell, a prokaryotic cell, an animal cell, a eukaryotic cell, or a plant cell.

26. A method of modulating expression of a gene product in a cell, the method comprising:
(i) expressing the engineered receptor polypeptide construct of paragraph 1 in a cell,
wherein the intracellular domain comprises a transcription factor, a dominant negative polypeptide, or an epigenetic regulator protein,
(ii) optionally providing the cognate ligand,
wherein in the presence of the cognate ligand, the intracellular effector domain is released from the engineered receptor polypeptide by γ-secretase cleavage, thereby modulating expression of the gene product in the cell.

27. The method of paragraph 26, wherein the gene product is a nucleic acid gene product or a protein gene product.

28. The method of paragraph 27, wherein the nucleic acid gene product comprises mRNA, miRNA, shRNA, siRNA, dsRNA, or an antisense nucleotide.

29. The method of paragraph 27, wherein the protein gene product is a secreted protein.

30. The method of any one of paragraphs 26-29, wherein expression of the gene product is increased.

31. The method of any one of paragraphs 26-30, wherein expression of the gene product is reduced or inhibited.

32. The method of any one of paragraphs 26-31, wherein the intracellular effector domain comprises an intracellular targeting sequence.

33. The method of any one of paragraphs 26-32, wherein the intracellular targeting sequence comprises a nuclear targeting sequence, a mitochondrial targeting sequence, an endoplasmic reticulum targeting sequence, a peroxisomal targeting sequence, a plasma membrane targeting sequence, a trans-Golgi targeting sequence or a lysosomal targeting sequence.

34. The method of any one of paragraphs 26-33, wherein the cognate ligand is a drug, an antigen, or a secreted protein expressed by the cell or a neighboring cell.

35. The method of paragraph 34, wherein the drug is an FDA-approved drug.

36. The method of any one of paragraphs 26-35, wherein the cognate ligand is a naturally occurring ligand or antigen.

37. A method of inducing cell death selectively in a cell, the method comprising:
  (i) expressing the engineered receptor polypeptide construct of paragraph 1 in a cell,
    wherein the cell is a therapeutic cell, an unwanted cell type in a cell manufacturing procedure, or a bacterial cell,
    wherein the intracellular domain comprises a cytotoxic protein or a pro-apoptotic protein,
  (ii) optionally providing the cognate ligand,
    wherein in the presence of the cognate ligand, the intracellular effector domain is released from the engineered receptor polypeptide by γ-secretase cleavage, thereby inducing cell death in the cell.

38. The method of paragraph 37, wherein the cognate ligand is a drug.

39. The method of paragraph 38, wherein the drug is an FDA-approved drug.

40. The method of paragraph 37, wherein the cognate ligand is a naturally occurring ligand or antigen.

41. The method of any one of paragraphs 37-40, wherein the therapeutic cell comprises a CAR T cell, an embryonic stem cell, an induced pluripotent stem cell, a progenitor cell, a probiotic or a differentiated cell.

42. A method of sensing an analyte, the method comprising: expressing the engineered receptor polypeptide construct of paragraph 1 in a cell,
  wherein the intracellular effector domain comprises a detectable product,
  wherein the analyte displaces the intramolecular peptide and binds to the at least one ligand binding site on the extracellular ligand binding domain,
  wherein in the presence of the analyte, the intracellular effector domain is released from the engineered receptor polypeptide by γ-secretase cleavage, thereby inducing expression of the detectable product in the cell.

43. The method of paragraph 42, wherein the intracellular effector domain comprises a fluorescent protein, a chemiluminescent enzyme, a colorimetric marker, or an enzyme.

44. The method of paragraph 42 or 43, wherein the analyte is detected in a cellular microenvironment or in solution.

45. The method of paragraph 44, wherein the cellular microenvironment comprises a tumor microenvironment.

46. A method of inducing expression of a chimeric antigen receptor in a T cell in the presence of a target antigen, the method comprising: expressing the engineered receptor polypeptide construct of paragraph 1 in a T cell that also comprises a nucleic acid construct encoding a chimeric antigen receptor under the control of an inducible promoter,
  wherein the intracellular effector domain comprises an agent that binds the inducible promoter to induce expression of the chimeric antigen receptor,
  wherein when the ligand binding site on the extracellular ligand binding domain is bound to an antigen present on a target cell or bound to a soluble antigen present in a target cellular microenvironment, the intracellular effector domain is released from the engineered receptor polypeptide construct by γ-secretase cleavage, thereby inducing expression of the chimeric antigen receptor in the cell.

47. The method of paragraph 46, wherein the target cell is a cancer cell.

48. The method of paragraph 46, wherein the target cellular microenvironment comprises a tumor microenvironment.

49. The method of paragraph 46, wherein the antigen present on a target cell comprises a cancer cell antigen.

50. The method of paragraph 46, wherein the soluble antigen present in the target cellular microenvironment comprises a soluble protein secreted from a cancer cell.

51. The method of paragraph 50, wherein the soluble protein secreted from a cancer cell comprises a growth factor, a cytokine, a chemokine, an interferon, or an extracellular matrix degrading enzyme.

52. A method for inducing an immune response in a subject, the method comprising: expressing the engineered receptor polypeptide construct of paragraph 1 in an immune cell,
  wherein the intracellular effector domain comprises an agent that activates the immune cell or induces expression of a secreted protein that activates a second immune cell,
  wherein when the engineered receptor polypeptide construct binds a target antigen present on a target cell or binds a soluble target antigen present in a target cellular microenvironment, the intracellular effector domain is released from the engineered receptor polypeptide by γ-secretase cleavage, thereby inducing an immune response in the subject.

53. The method of paragraph 52, wherein the agent that activates the immune cell or the secreted protein that activates a second immune cell comprises a cytokine, a chemokine, an interferon, an interleukin.

54. The method of paragraph 52, wherein the agent that activates the immune cell comprises a Toll-like receptor or ligand thereof.

55. The method of any one of paragraphs 52-54, wherein the immune cell or second immune cell comprises a T cell, a B cell, a mast cell, a granulocyte, a basophil, a neutrophil, an eosinophil, a monocyte, a dendritic cell, or a natural killer cell.

56. The method of any one of paragraphs 52-55, wherein the immune cell expressing the engineered receptor polypeptide construct is the same or different from the second immune cell.

57. An engineered receptor polypeptide construct with enhanced avidity, the construct comprising:
  (i) an extracellular ligand binding domain having a first and second ligand binding site,
  (ii) an optional flexible polypeptide linker,
  (iii) an intramolecular peptide that binds to a ligand binding site in the extracellular ligand binding domain,
  (iv) a transmembrane domain comprising at least one γ-secretase cleavage site, and
  (v) an intracellular effector domain,
  wherein the first ligand binding site does not bind to the intramolecular peptide,
  wherein the second ligand binding site binds to the intramolecular peptide,
  wherein when the intramolecular peptide is bound to the second ligand binding site, the extracellular ligand binding domain is maintained in a position that sterically inhibits γ-secretase from cleaving the construct at the at least one γ-secretase cleavage site,
  wherein, in the presence of a cognate ligand, the intramolecular peptide is displaced from the second ligand binding site, thereby releasing the extracellular ligand binding domain to a conformation that permits γ-secretase to cleave the construct at the at least one γ-secretase cleavage site and the intracellular effector domain is released, and wherein binding of the ligand to the first ligand binding site increases the avidity of the engineered receptor polypeptide construct by modulating the dynamic equilibrium of ligand on/off time and increasing the amount of time the ligand is bound to the second ligand binding site.

58. The method of paragraph 57, wherein the first ligand binding site and second ligand binding sites bind the same ligand.

59. The method of paragraph 57, wherein the first ligand binding site and second ligand binding sites bind different ligands.

60. The method of any one of paragraphs 57-59, wherein the amount of time the ligand is bound to the second ligand binding site is increased by at least 10%.

61. A template nucleic acid encoding an engineered receptor polypeptide construct operably linked to a promoter.

62. The template nucleic acid of paragraph 61, wherein the promoter is a tissue-specific promoter.

63. A viral vector or plasmid containing the template nucleic acid of paragraph 61 or 62.

64. The viral vector or plasmid of paragraph 63, wherein the viral vector is a lentivirus, a parvovirus, an adenovirus, or an adenovirus associated vector (AAV).

65. A lipofection reagent in an admixture with the template nucleic acid of paragraph 61 or 62 or the viral vector or plasmid of paragraph 63 or 64.

EXAMPLES

Example 1: Modular Input Modular Output sensors, or MIMOsensors

In natural biological processes, cells are continuously sensing their environment and respond with the appropriate cellular output. This can help cells maintain homeostasis or carry out new biological actions such as differentiation into new cell type/tissues, mount an immunological response, or signal for other complex cascades like apoptosis. As researchers and clinicians, it is often desired to engineer synthetic controls of biological processes to create complex gene networks or to control a cellular function with the use of a synthetic ligand.

Accordingly, provided herein is a platform to create customizable, cellular biosensors—a system in which the user can specifically define the input ligand the cell senses to generate a customized genetic output or protein release response. With this technology, one is enabled to detect free floating or bound small molecules, peptides, or proteins and generate output responses like gene activation, split protein complementation, or cleavage mediated protein activity.

This is achieved through a controlled receptor cleavage event by gamma secretase protease (γ-secretase), found natively in many multicellular organisms and importable to other eukaryotes such as yeast[1]. The γ-secretase complex is an intramembrane protease with a large family of protein substrates, and it is thought to be in part mediated by steric hindrance via its nicastrin subunit[2]. Congruent with this theory, transmembrane proteins with bulky ectodomains cannot be cut by γ-secretase unless steric hindrance is relieved. Previous synthetic tools have repurposed γ-secretase substrate Notch, a protein that is sequentially cleaved after surface bound ligand binding to release an intracellular domain. By replacing a part of the ligand binding portion of the ectodomain and the releasable intracellular domain, groups have previously created modular sensor for surface bound ligands thought to be mediated by force-dependent cleavage and the Notch negative regulatory region (NRR).

In an orthogonal approach, the inventors have created a novel receptor that is controlled by competitive ligand binding interactions. When a competitively inhibiting ligand is introduced to the receptor, intramolecular inhibition is released, triggering γ-secretase cleavage and subsequent programmable intracellular responses. This approach lacks the need for an NRR, and enables sensing of soluble ligands in addition to tethered ligands. By using a combination of ligand binding domains (LBDs) and ligand-mimicking epitopes, the inventors have created Modular Input Modular Output sensors, or MIMOsensors.

Specifically, each sensor employs a LBD and a corresponding ligand-mimicking, intramolecular peptide. These pairs spontaneously bind each other to cause steric hindrance to the sensor's transmembrane γ-secretase cleavage site (FIG. 1). Therefore, the LBD remains bound to the intramolecular peptide in the absence of target ligand, and γ-secretase cannot cleave and release the intracellular domain (ICD). Upon higher affinity target ligand, the LBD is competitively displaced, intramolecular inhibition is relieved, and γ-secretase mediates the proteolytic release of an ICD. This approach allows one to utilize newly derived or existing LBDs, including naturally occurring ligand binding proteins and proteins derived from screening/evolution or computational design. The identified LBD is then fused to a newly derived or existing peptide to intramolecularly bind in cis on the protein ectodomain to cause the ligand-mediated, steric hindrance. The ICD's function is independent of the ectodomain, and the domain can be chosen to match the users desired cellular response. To date, the inventors have shown that this technology can be employed to make three classes of ligand sensors, sensing small molecules and protein domains. Together these examples demonstrate that this approach is generalizable to many ligand types, including but not limited to small molecules, peptides, and proteins.

Figure 2A:
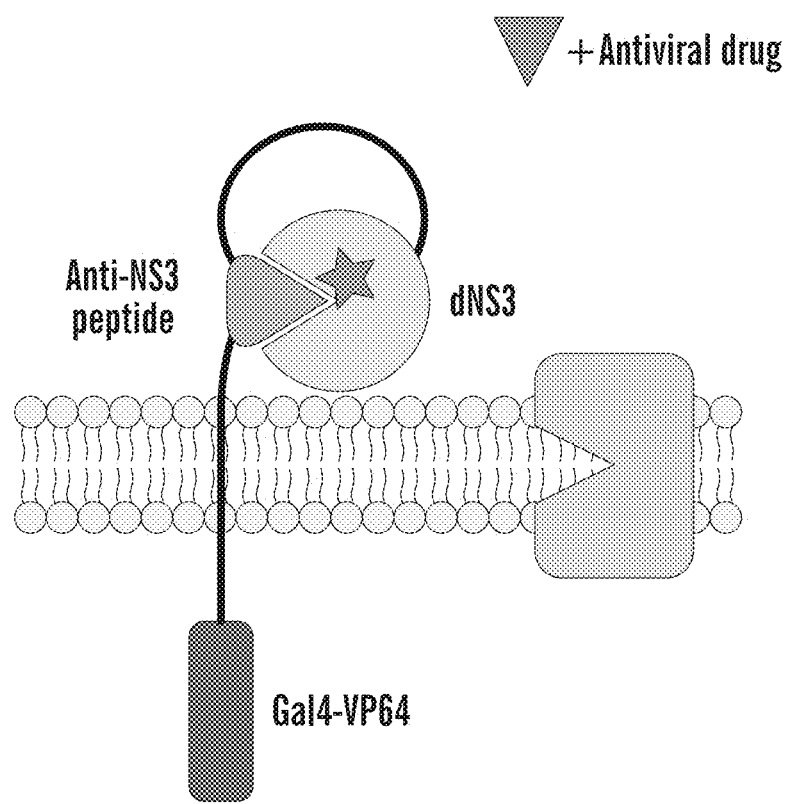
FIGS. 2A-2B.
Figure 2B:
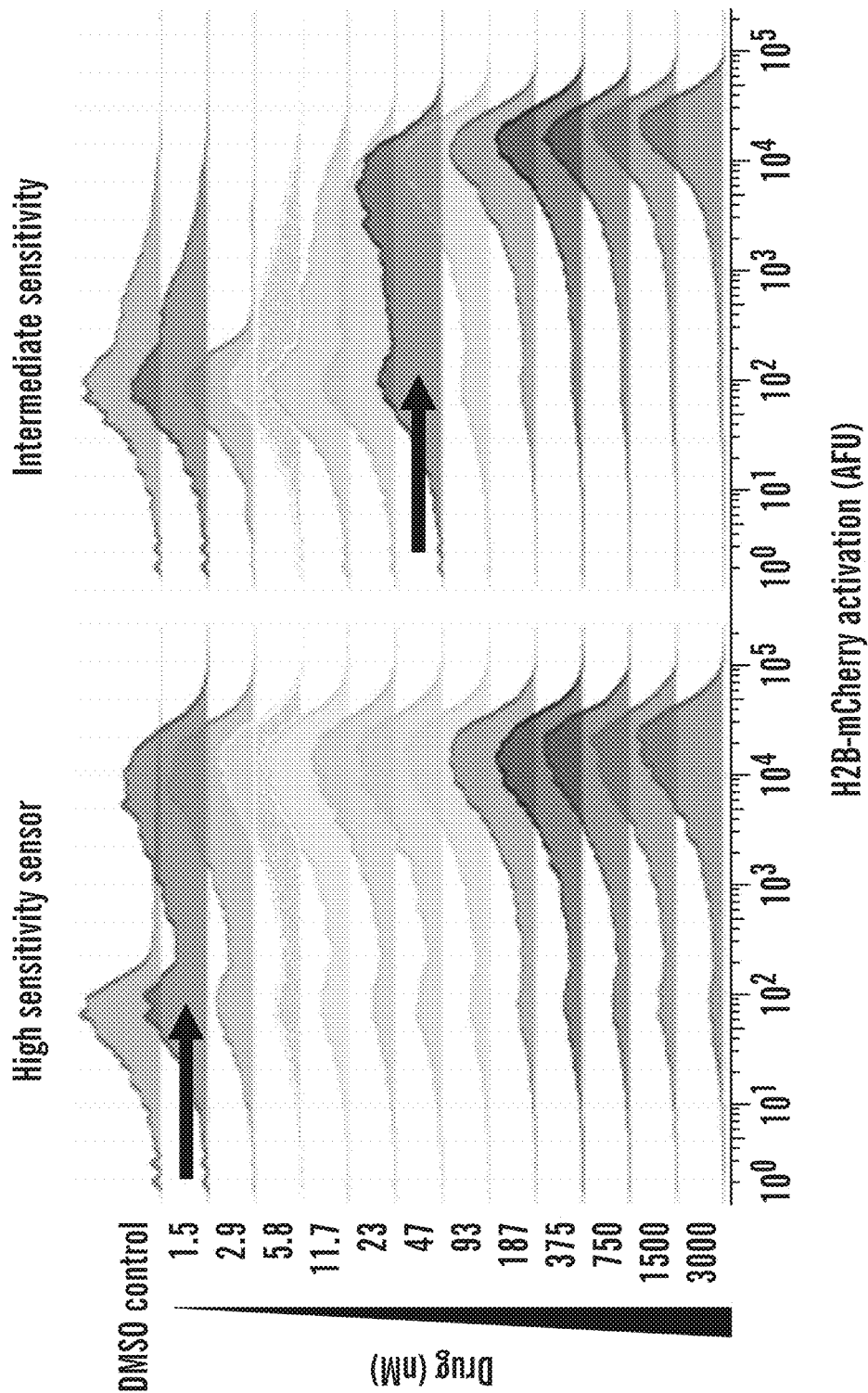

To first demonstrate the principle, the inventors developed a tool to sense antiviral drugs. This was achieved by using catalytically inactive NS3 protease (NS3$^{S139A}$, referred to here as dNS3) as an LBD and intramolecular peptides (FIG. 2A). For proof of concept, the ICD chosen was a synthetic transcription factor, Gal4-VP64, which activates UAS promoter driven H2B-mCherry gene expression. The peptide sequences used as intramolecular binding peptides widely vary in affinity to NS3, and include a synthetically derived peptide of high affinity ($K_D$=10.5 nM)[3] and low affinity peptides ($EC_{50}$=1-10 μM)[4] derived from the native NS3 cut sites. As expected, the sensor responds to antiviral drug grazoprevir with concentration dependent activation of fluorescent H2B-mCherry (FIG. 2B). The substitution of the high affinity peptide for low affinity peptide appears to increase the sensitivity of the sensor, consistent with the theory of competitive displacement kinetics. A total of three different intramolecular peptides were successfully employed to control this antiviral drug sensor, demonstrating modularity of the upstream peptide sequence of γ-secretase substrates, and suggests the sensitivity of these sensors is tunable.

Figure 3:
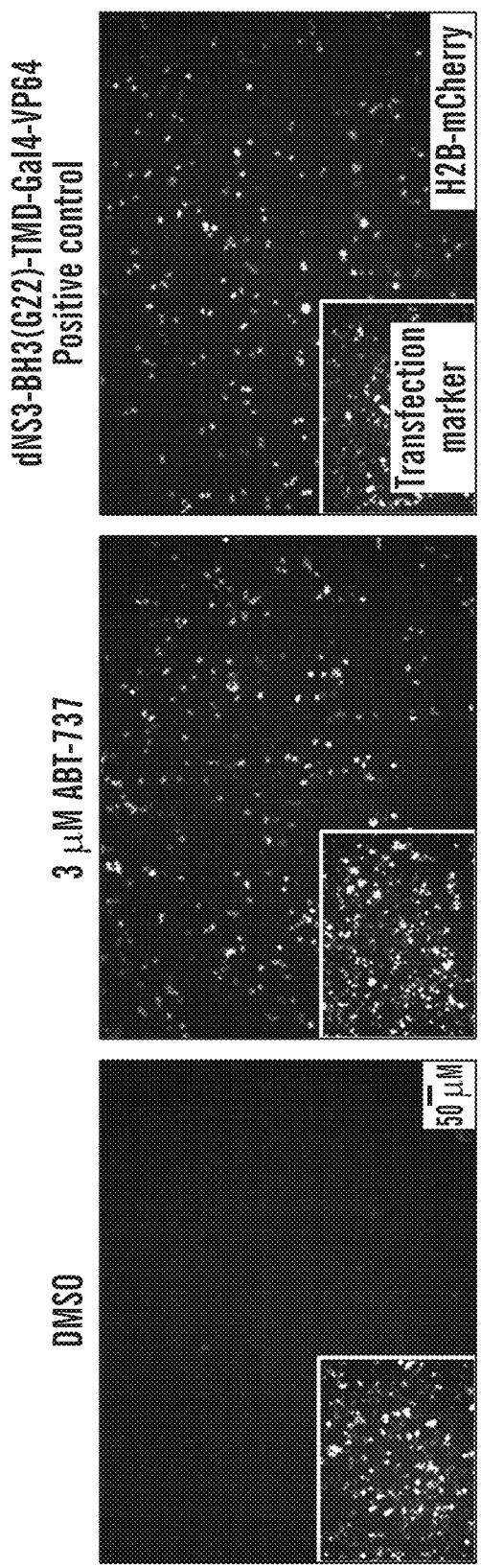
FIG. 3 Activity of BCL-xL-BH3(G22)-Gal4-VP64 upon presence of BCL-xL inhibitors. BCL-xL serves as a ligand binding domain and BH3(G22) serves as an intramolecular peptide. Upon BCL-xL binding ligand, such as ABT-737, intramolecular peptide is displaced and the Gal4-VP64 ICD is released to drive H2B-mCherry expression. This is compared to a positive control of dNS3-BH3(G22)-TMD-Gal4VP64, which has a mismatched LBD and intramolecular peptide and is expected to lead to constitutive ICD release. H2B mCherry expression is visualized via microscopy. A fluorescent transfection marker is also shown to verify the presence of cells as a smaller corresponding image. Images were taken 48 hours after transfection and drug addition. Scale bar 50 μm.

The inventors next applied this methodology to a completely different LBD and peptide pair, BCL-xL and the BH3(G22) peptide, while keeping the ICD the same. Upon Bcl-xL binding synthetic small molecule drug ABT-737, the sensor responds to BCL-xL inhibitor ABT-737 with concentration dependent activation of H2B-mCherry (FIG. 3).

Figure 4:
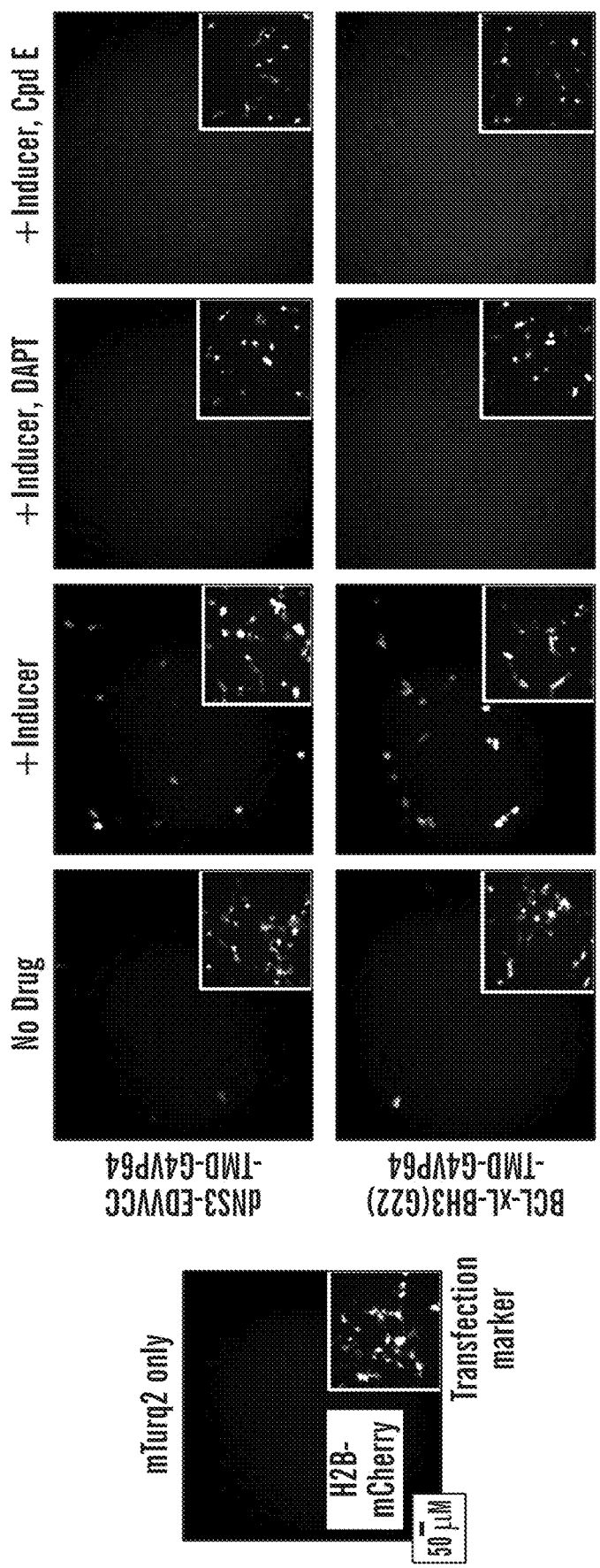
FIG. 4 Gamma secretase dependence of two distinct sensors. dNS3-(EDVVCC (SEQ ID NO: 57))-TMD-Gal4-VP64 and BCL-xL-BH3(G22)-TMD-Gal4-VP64 sensors were tested for gamma secretase dependence via the addition of gamma secretase inhibitors DAPT and Compound E (Cpd E). In the presence of the respective ligand inducer for each sensor, the sensor activates ICD driven H2B-mCherry expression. Upon addition of inducer and either gamma secretase inhibitor, H2B-mCherry signal is ablated. Images are taken 24 hours after transfection and drug addition. A fluorescent transfection marker is shown as a smaller corresponding image. Drug concentrations are as follows: NS3 inducer, grazoprevir 3 μM; BCL-xL inducer, ABT-737 3 μM; DAPT 5 μM; Compound E 1 μM. Scale bar 50 μm.

To probe into the mechanism of activation for the antiviral drug sensors and ABT-737 sensor, the inventors next inhibited γ-secretase with selective inhibitors, DAPT and compound E. Upon inhibition with either of these compounds, ICD driven activation of H2B-mCherry was inhibited (FIG. 4). Inhibition also occurred despite the presence of each associated sensor inducer, indicating γ-secretase plays a crucial role in MIMOsensor activation and is required for ICD release.

Figure 5B:
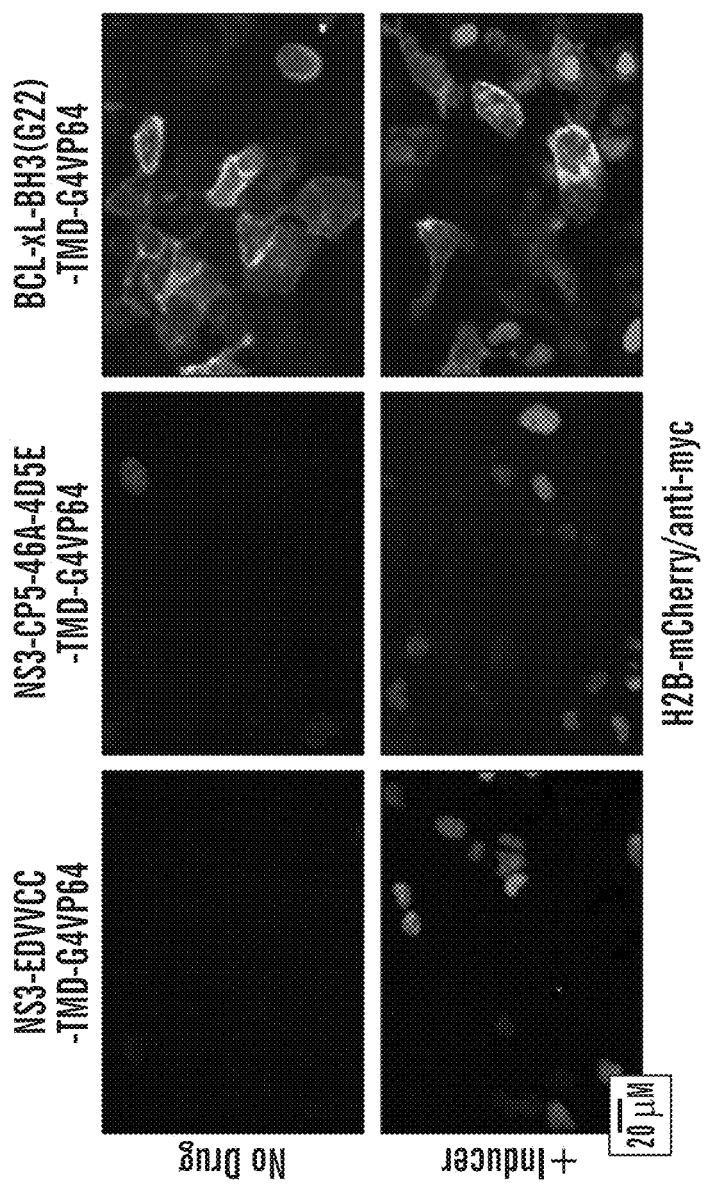
FIGS. 5A-5B Live surface staining of three MIMOsensors.
Figure 5A:
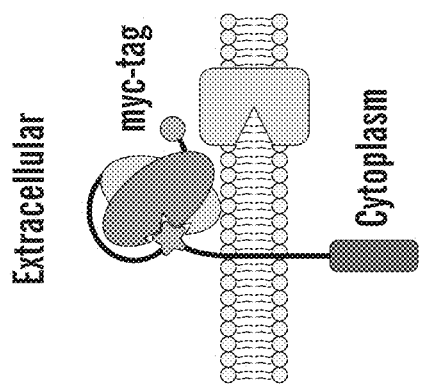

Following these experiments, cells containing the sensors BCL-xL-BH3(G22)-TMD-Gal4-VP64, dNS3-(EDVVCC (SEQ ID NO: 57))-TMD-Gal4-VP64, and dNS3-(CP5-46A-4D5E)-TMD-Gal4-VP64 were surface stained for N-terminal myc tag that was placed in each sensor (FIG. 5). In both embodiments corresponding inducer led to reporter gene activation, but surface presentation was different between the two sensors. The BCL-xL-BH3(G22)-TMD-Gal4-VP64 was expressed well at the surface, while the dNS3-(EDVVCC (SEQ ID NO: 57))-TMD-Gal4-VP64 system was not expressed well at the surface. This highlights that surface presentation is not crucial for membrane permeable ligands.

Figure 6:
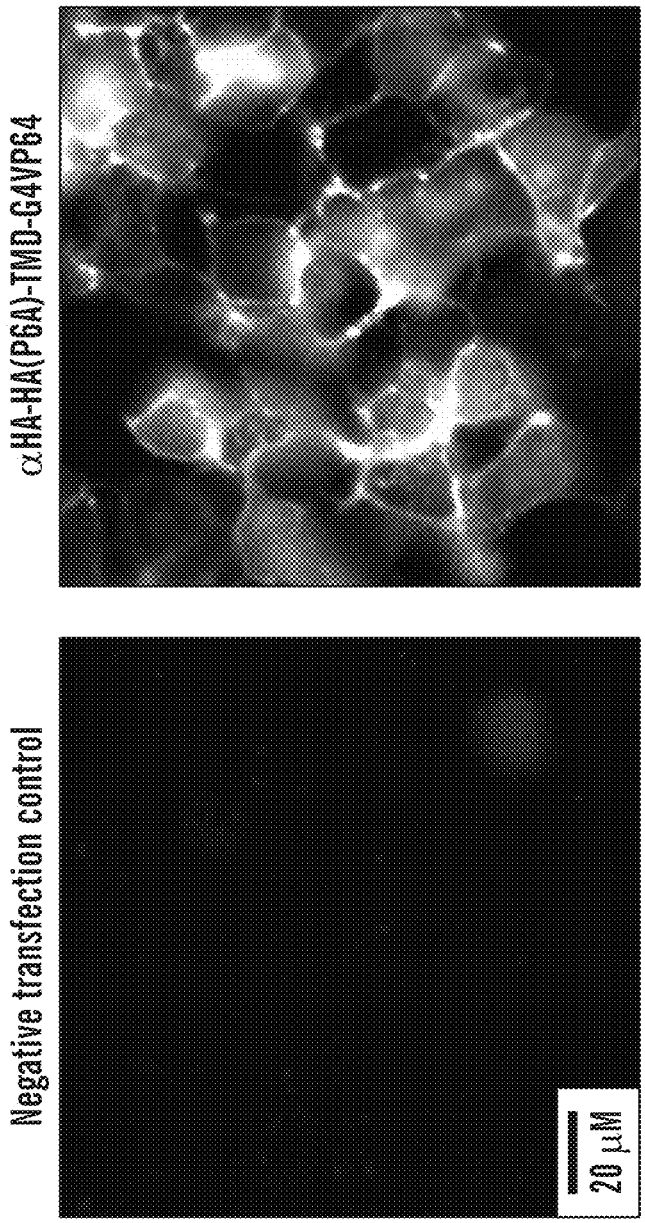
FIG. 6 Live surface staining of Anti-HA-HA(P6A)-TMD-Gal4VP64 compared to a negative transfection control of an untagged protein. Surface staining is detected via anti-myc tag antibody conjugated to Alexafluor 647 dye, followed by fixation with paraformaldehyde. Surface staining was performed 24 hours after transfection. Scale bar 20 μm.
Figure 7A:
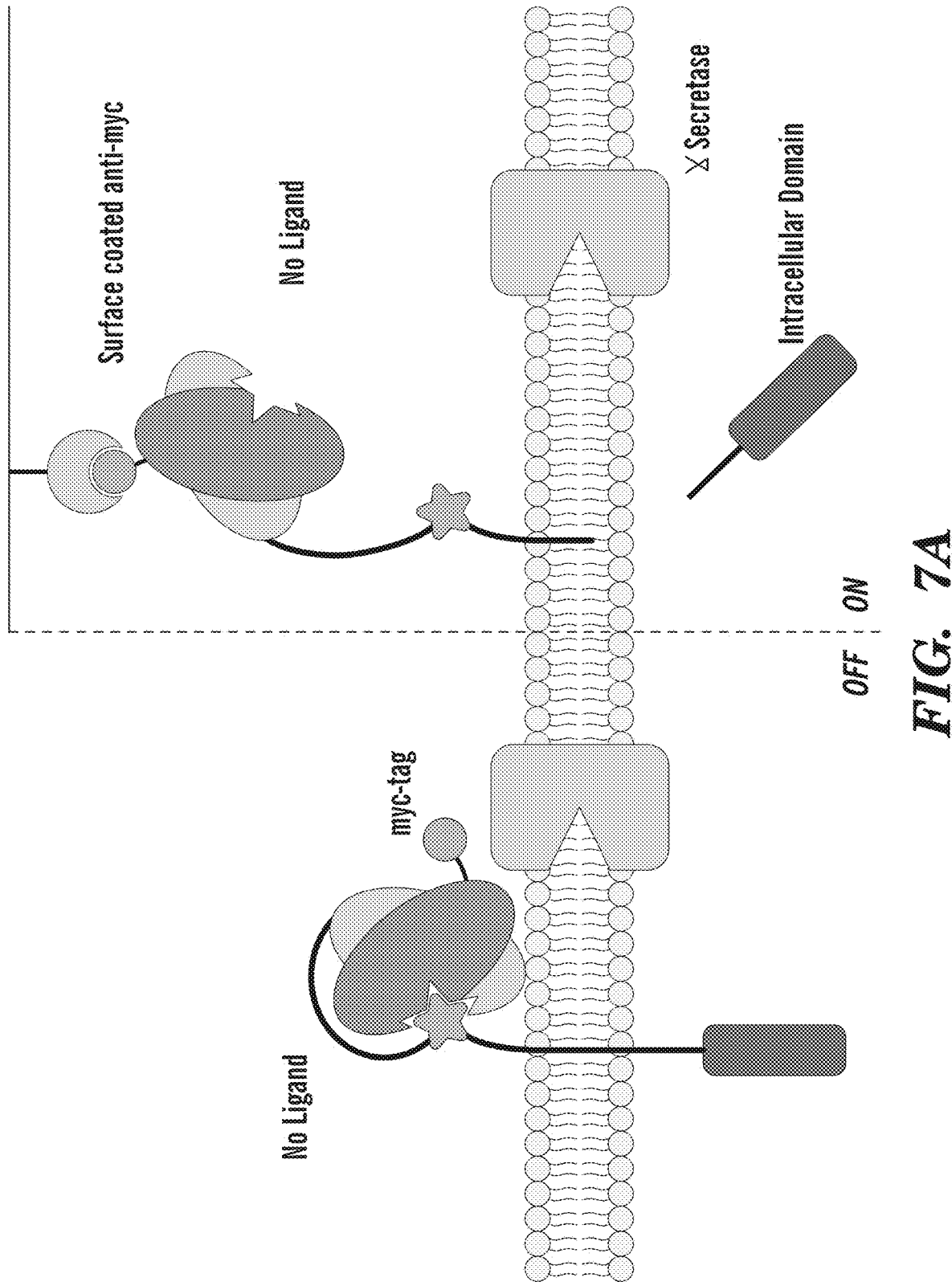
FIGS. 7A-7B (FIG. 7A) Activation of HA sensor, anti-HA-HA(P6A)-TMD-Gal4VP64 by surfaces coated with anti-myc antibody.
Figure 7B:
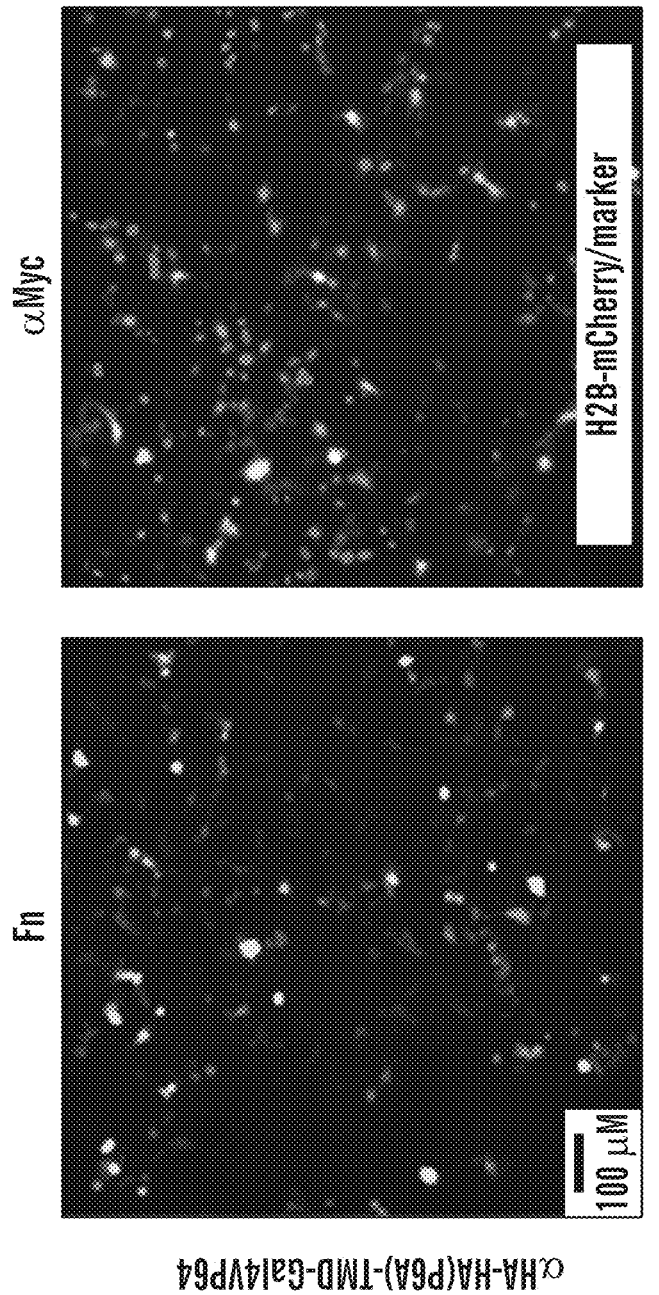
Figure 8:
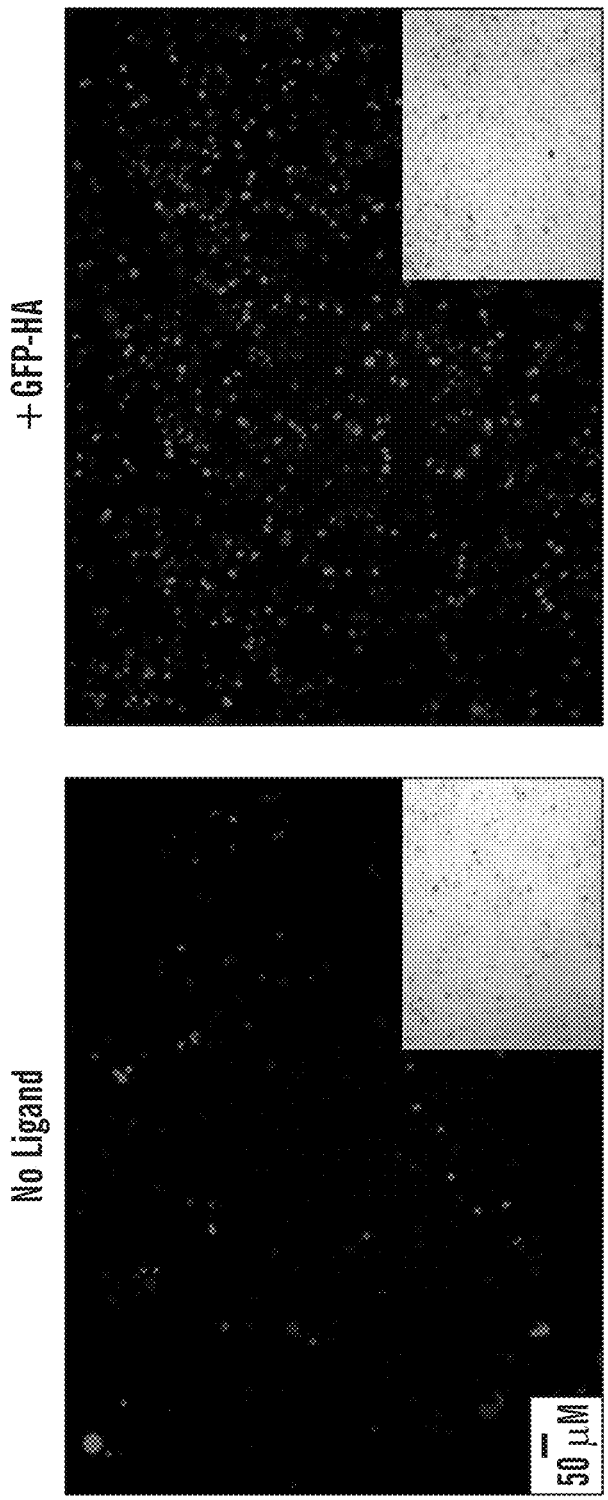
FIG. 8 Activation of HA sensor, Anti-HA-HA(Y8A)-TMD-Gal4VP64. Upon presentation of soluble GFP tagged with HA peptide epitope, the sensor ICD is cleaved to drive expression of H2B-mCherry reporter gene. A smaller corresponding brightfield image is shown for each population to verify a large population of cells are present in each condition. Cells were imaged 42 hours after transfection and ligand addition. Ligand refers to purified GFP-HA, 22 μM. Scale bar 50 μm.
Figure 9:
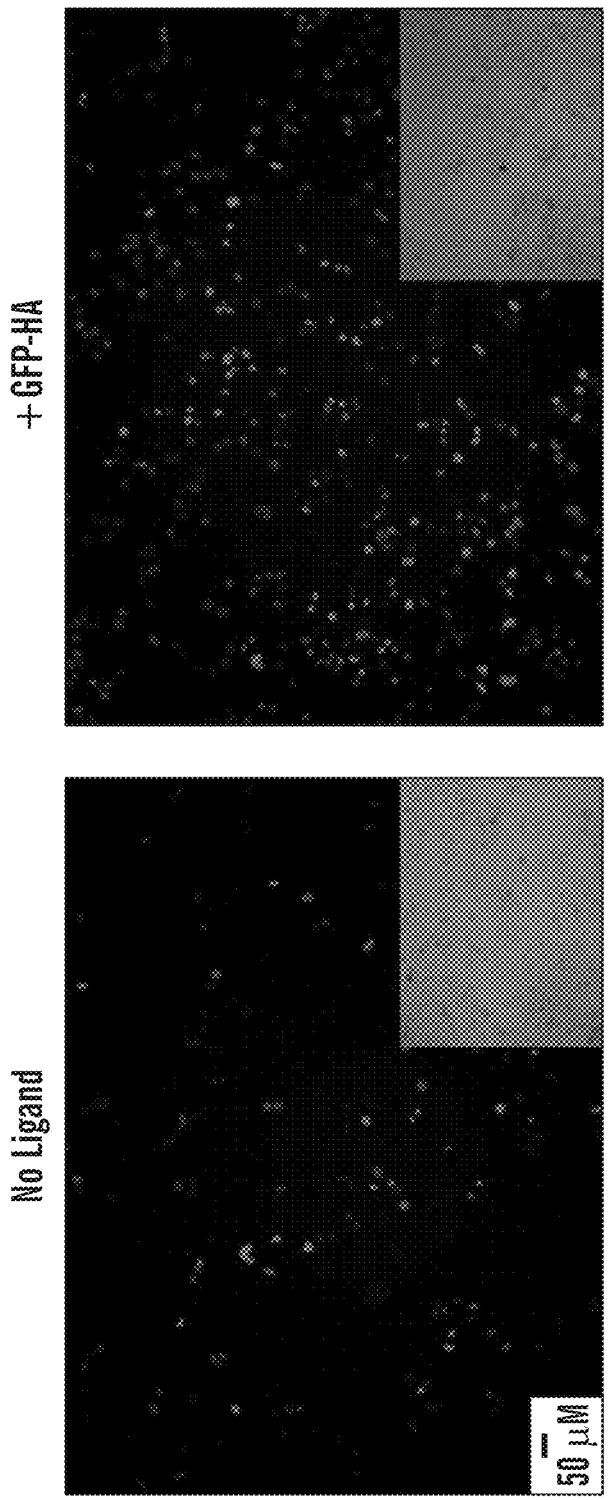
FIG. 9 Activation of HA sensor, Anti-HA-HA(D7A)-TMD-Gal4VP64, with an alternative intramolecular peptide, HA(D7A). Upon presentation of soluble GFP tagged with HA peptide epitope, the sensor ICD is cleaved to drive expression of H2B-mCherry reporter gene. A smaller corresponding brightfield image is shown for each population to verify a large population of cells are present in each condition. Cells were imaged 42 hours after transfection and ligand addition. Ligand refers to purified GFP-HA, 22 μM. Scale bar 50 μm.
Figure 10A:
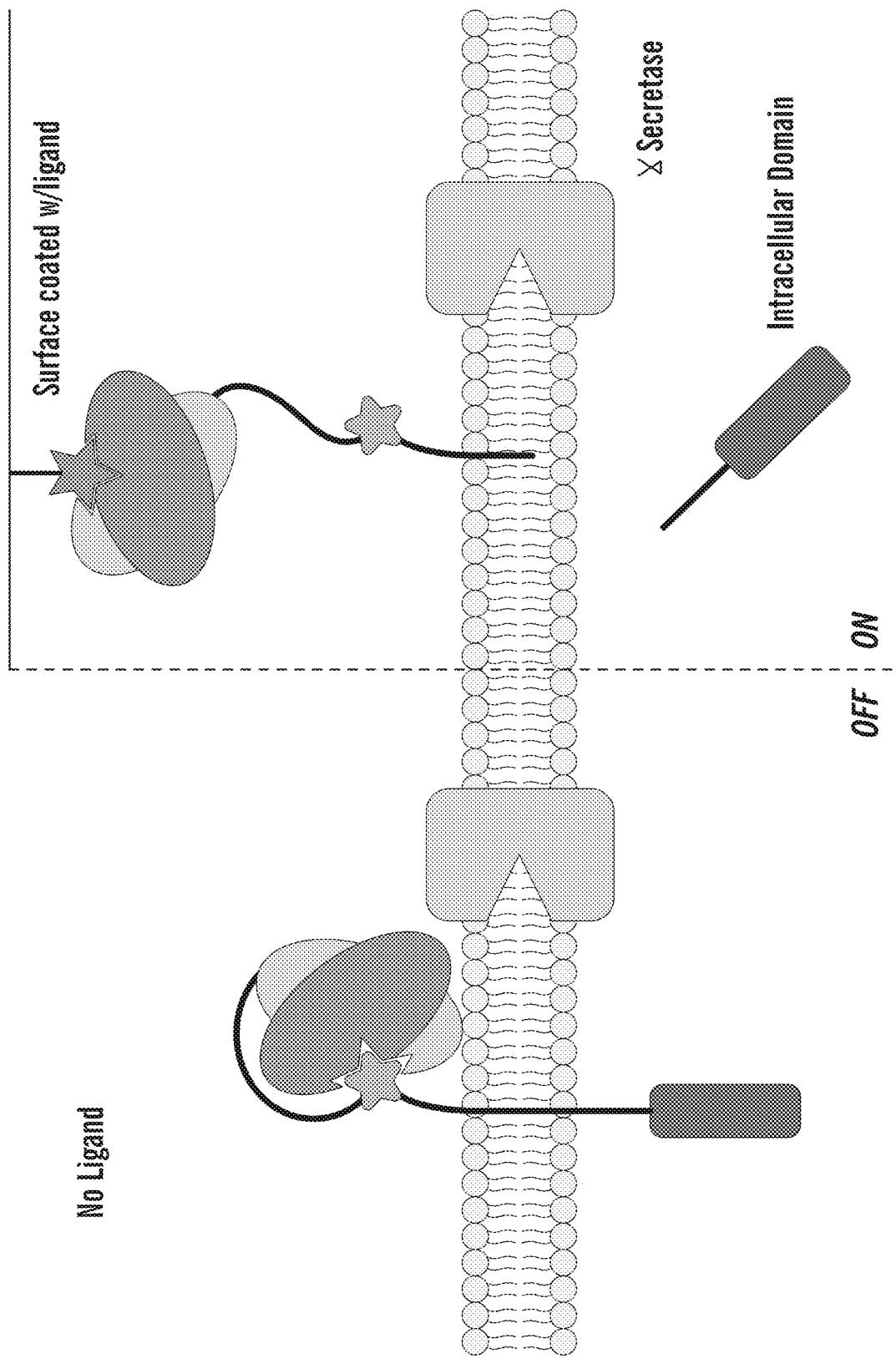
FIGS. 10A-10B (FIG. 10A) Activation of HA sensor, Anti-HA-HA(Y8A)-TMD-Gal4VP64 on plated GFP-HA.
Figure 10B:
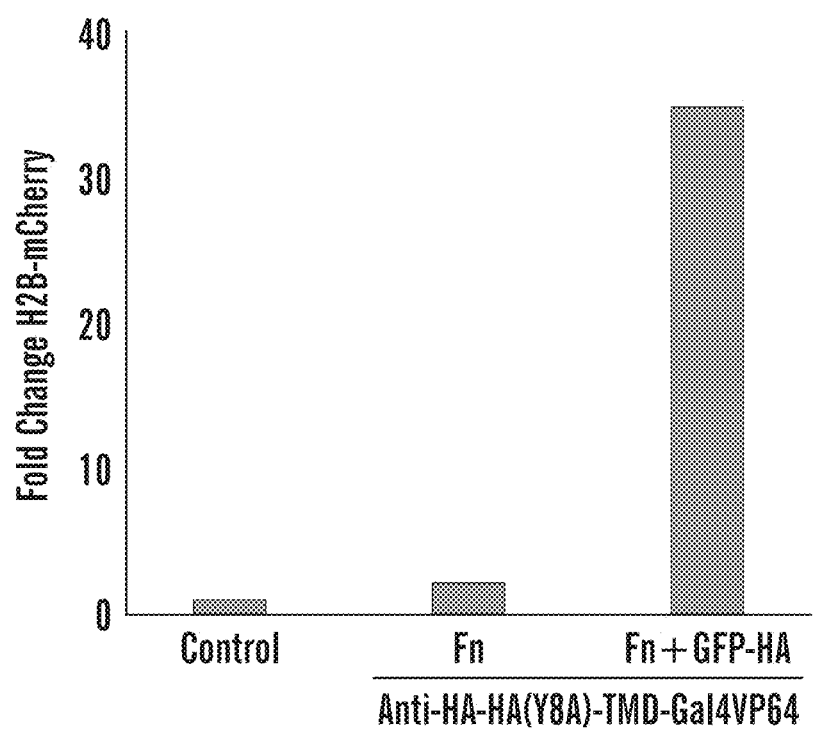

Next, the inventors set out to sense a non-permeable, protein-based ligand. For this demonstration, Influenza Hemagglutinin (HA) peptide was selected as a ligand, using previously characterized anti-HA frankenbody scFv[5] (anti-HA) and HA peptide mutants (referred to as HA(mutant)) as the intramolecular peptide. The surface expression of one anti-HA-HA(mutant)-TMD-Gal4-VP64 sensor was analyzed with live staining of myc epitope and confirmed to be on the surface (FIG. 6). Although this particular sensor did not respond to drug (likely because intramolecular peptide was not competitively displaceable), this sensor was able to respond to plated anti-myc antibody ligand (FIGS. 7A-7B). This demonstrates that these sensors can also be activated by other surface coated ligands that are not part of the LBD/intramolecular peptide interaction, which is similar to Notch extracellular domain mediated signaling. To make the sensor respond to soluble ligand, the inventors made more drastic mutations to the intramolecular HA epitope. It was hypothesized that this mutation would create a lower affinity between anti-HA scFv and the intramolecular peptide, allowing native HA ligand to be able to displace the scFv from the HA(mutant) and trigger sensor activation. When mutations HA(Y8A) or HA(D7A) were made, the new anti-HA-HA(mutant)-TMD-Gal4-VP64 sensor responded to soluble epitope tagged to GFP (FIGS. 8 & 9), or surface plated GFP-HA (FIGS. 10A-10B).

Altogether, these three sensor systems targeted three different ligands to demonstrate a modular platform to sense soluble or bound ligands and output an intracellular domain response such as transcription. The inputs and outputs are expected to be modular to sense virtually any ligand and output any releasable intracellular protein domain. The ICD used in these experiments was a transcription factor, but this can easily be modified to intracellular domains such as a split protein fragment or any protein, for example a protein whose release triggers an apoptotic cascade.

Improvements Over Existing Technology

There are multiple existing systems to attempt to create generic extracellular sensors for soluble ligands. The developed programmable extracellular sensors to date mainly consist of the following classes of receptors: synthetic GPCRs[6,7], Modular extracellular Sensors (MESA)[8], Chimeric antigen receptors (CARs)[9], and Generalized Extracellular sensors (GEMS)[10] Perhaps the most engineerable sensor to date has been the GEMS or MESA sensors, but each of these have ligand constraints. Specifically, GEMs requires antigens with two distinct epitopes or special case scFvs that undergo a large conformational change upon binding to a single epitope. The outputs for all systems besides MESA also present high crosstalk with endogenous mammalian biology. MESA overcomes this with synthetic components, but requires ligands with multiple epitopes as well and require two engineered proteins instead of one. MIMOsensors overcome the problems of ligand constraints, endogenous gene crosstalk, and lack of engineerability.

More recently, two-component systems have been transgenically expressed in mammalian cells[11], but these face similar drawbacks to synthetic GPCRs -they are more difficult engineer and have limited genetic outputs. SynNotch has also been employed as a modular extracellular receptor platform[12,13], but these are controlled by interactions with tethered ligand, whereas MIMOsensors are solely controlled by affinity interactions. By its distinct mechanism, the receptor technologies described herein can bind soluble and tethered ligands. Altogether, MIMOsensors are the only sensors to have minimal ligand constraints, low crosstalk with endogenous mammalian biology, and high engineerability.

Additional Embodiments

The MIMOsensors are full of very modular parts, but are predominately based on the idea of affinity-controlled cleavage by γ-secretase. Accordingly, the ligand binding domain can be replaced to virtually any other LBD, the peptide can be replaced with any other domain that competes with the binding pocket of the target ligand but does not interfere with γ-secretase cleavage, the transmembrane domain can be replaced with any other transmembrane domain that is cleavable by γ-secretase (there are many in eukaryotes), and the intracellular domain can be replaced by virtually any other cargo such as but not limited to transcription factors, localizable proteins, or split proteins. The inventors are currently in the process of varying all of these parts. In addition, the inventors plan to change the LBD-peptide pairs to sense new ligands and tune ligand sensitivity, the transmembrane domain will be varied to tune cleavage rate/background cleavage of the sensor by γ-secretase, and the ICD will be changed for different transcription factors and cellular effectors. For all these distinct domains, flexible linkers between them are also expected to be variable.

In addition, it is reasonable to assume that the LBD can be supplemented with another LBD targeting the same ligand to increase avidity. This second LBD would not need to interact with the intramolecular peptide. Instead, it would increase avidity to the ligand and result in higher sensitivity of the sensor. An example of this would be adding an additional anti-GFP nanobody to the HA MIMOsensors. Upon presentation of GFP-HA ligand, it would be expected to increase sensitivity of the sensor. One can also alter sensing responses by adding additional LBDs and peptides within the one receptor.

To reiterate, each part of the sensor is modular:
a. The extracellular LBD and mimotope should be replaceable with any LBD mimotope peptide pair
b. The TMD should be replaced with any gamma secretase transmembrane substrate. This could change the kinetics cleavage, that would have effects on parameters like background spontaneous cleavage, dose dependence of ligand, and cellular output response time.

c. The ICD can be changed out with any protein or protein fragment domain.

d. The linkers between domains are expected to be modular to other flexible linker amino acids. The length of these linkers is also expected to be somewhat variable.

Other modifications can be made to change the characteristics of these sensors:

a. The dose response of a sensor should also become more sensitive with additional ligand binding domains to increase the avidity.

b. The sensor should be able to be re-purposed to sense proteolytic activity by placing protease site between an LBD and mimotope. Upon protease activity, an LBD can be engineered to eventually dissociate from the low affinity mimotope c. Other proteins that undergo large conformational changes upon an event (such as phosphorylation) could be applied in place of the LBD if it causes the domain to dissociate from a binding peptide. Alternatively, the protein undergoing conformational change could work sufficiently without a binding peptide to shield the gamma secretase in absence of conformational change, then allow gamma secretase cleavage upon a conformational change event.

d. Each sensor is expected to be regulatable by presenting ligands on the same cell or a neighboring cell. Therefore, ligand is expected to be modulate sensor activity in cis on the cell surface or from trans presentation of ligand on a neighboring surface.

e. It is expected that this sensor platform will translate to any organism capable of expressing γ-secretase Applications of MIMOsensors The sensors described herein can be used for a multitude of applications—in virtually any scenario where an extracellular input needs to correspond to an intracellular genetic or protein-cleavage output. Potential product examples through the use of MIMOsensors are listed below:

a. A soluble or tethered antigen sensor to induce the expression of a Chimeric antigen receptor/T-cell receptor to make tumor targeting more accurate.

b. A soluble or tethered antigen sensor to induce a response of immune cell machinery toward a specific antigen.

c. Combinatorial antigen sensor for CAR-T to only activate T-cell responses in the presence of multiple antigens associated with cancer. Antigens could be soluble or surface tethered for detection.

d. A feedback controller express a gene dependent on another the presence of another protein e. A sensor for analyte concentrations in tissue microenvironments with a colorimetric or chemical readout f. A sensor for analyte concentrations in solution with a colorimetric or chemical readout g. A drug inducible kill-switch for cell therapies using FDA approved drugs.

h. A drug inducible switch to control protein expression using FDA approved drugs.

i. A kill switch to sort for unwanted cell types in a cell manufacturing procedure.

j. A customized cellular sensor based on the customer's needs

Potential services through the use of MIMOsensors a. A service to analyze the concentrations of an analyte in a given solution.

| List of Peptides: |
|---|
| BH3(G22): APPNLWAAQRYGRELRRMADEGEGSFK (SEQ ID NO: 42) |
| CP5-46A-4D5E: GELDELVYLLDGPGYDPIHS (SEQ ID NO: 43) |
| HA epitope: YPYDVPDYA (SEQ ID NO: 44) |
| HA(P6A), referred to as HA(mutant) in the text: YPYDVADYA (SEQ ID NO: 45) |
| HA(D7A): YPYDVPAYA (SEQ ID NO: 46) |
| HA(Y8A): YPYDVPDAA (SEQ ID NO: 47) |
| Myc epitope: EQKLISEEDL (SEQ ID NO: 48) |

REFERENCES

1. Edbauer, D. et al. Reconstitution of gamma-secretase activity. *Nat. Cell Biol.* 5, 486-8 (2003).
2. Bolduc, D. M., Montagna, D. R., Gu, Y., Selkoe, D. J. & Wolfe, M. S. Nicastrin functions to sterically hinder γ-secretase-substrate interactions driven by substrate transmembrane domain. *Proc. Natl. Acad. Sci. U.S.A* 113, E509-E518 (2016).
3. Kügler, J. et al. High affinity peptide inhibitors of the hepatitis C virus NS3-4A protease refractory to common resistant mutants. *J. Biol. Chem.* 287, 39224-39232 (2012).
4. Gallinari, P. et al. Multiple Enzymatic Activities Associated with Recombinant NS3 Protein of Hepatitis C Virus. *Am. Soc. Microbiol.* 72, 6758-6769 (1998).
5. Zhao, Ning, Kamijo, Kouta, . . . Stsevich, T. A genetically encoded probe for imaging HA-tagged protein translation, localization, and dynamics in living cells and animals. *BioRxiv* (2018).
6. Barnea, G. et al. The genetic design of signaling cascades to record receptor activation. *Proc. Natl. Acad. Sci.* 105, 64-69 (2008).
7. Dong, S., Rogan, S. C. & Roth, B. L. Directed molecular evolution of DREADDs: A generic approach to creating next-generation RASSLs. *Nat. Protoc.* 5, 561-573 (2010).
8. Schwarz, K. A., Daringer, N. M., Dolberg, T. B. & Leonard, J. N. Rewiring human cellular input-output using modular extracellular sensors. *Nat. Chem. Biol.* 1-9 (2016). doi:10.1038/nchembio.2253
9. Chang, Z. L. et al. Rewiring T-cell responses to soluble factors with chimeric antigen receptors. *Nat. Chem. Biol.* 14, 317-324 (2018).
10. Scheller, L., Strittmatter, T., Fuchs, D., Bojar, D. & Fussenegger, M. Generalized extracellular molecule sensor platform for programming cellular behavior. *Nat. Chem. Biol.* (2018). doi:10.1038/s41589-018-0046-z
11. Maze, A. & Benenson, Y. Artificial signaling in mammalian cells enabled by prokaryotic two-component system. *Nat. Chem. Biol.* (2019). doi:10.1038/s41589-019-0429-9
12. Morsut, L. et al. Engineering Customized Cell Sensing and Response Behaviors Using Synthetic Notch Receptors. *Cell* 164, 780-791 (2016).
13. Roybal, K. T. et al. Precision Tumor Recognition by T Cells with Combinatorial Antigen-Sensing Circuits. *Cell* 164, 770-779 (2016).

The invention claimed is:

1. An engineered receptor polypeptide comprising:
   (i) an extracellular ligand binding domain having at least a first target ligand binding site,
   (ii) an optional flexible polypeptide linker,
   (iii) an intramolecular peptide that binds to the at least first target ligand binding site in the extracellular ligand binding domain,
   (iv) a transmembrane domain comprising at least one γ-secretase cleavage site, and
   (v) an intracellular effector domain,
   wherein, in the absence of a target ligand, the intramolecular peptide is bound to the at least first target ligand binding site resulting in steric hindrance of the at least one γ-secretase cleavage site in the transmembrane domain, and
   wherein, in the presence of a target ligand, the intramolecular peptide is displaced from the at least first target ligand binding site, thereby relieving the steric hindrance and allowing γ-secretase to mediate proteolytic cleavage at the at least one γ-secretase cleavage site and release of the intracellular effector domain.

2. The polypeptide of claim 1, wherein the optional flexible linker comprises at least 2 amino acids and no more than 300 amino acids.

3. The polypeptide of claim 1, wherein the intramolecular peptide has a lower, equal or greater affinity of binding to the first target ligand binding site than the target ligand.

4. The polypeptide of claim 1, wherein the intramolecular peptide does not inhibit gamma-secretase binding to the gamma-secretase cleavage site when placed in a juxtacrine position to the transmembrane domain.

5. The polypeptide claim 1, wherein the intramolecular peptide is an engineered peptide or a naturally occurring peptide.

6. The polypeptide claim 1, wherein the engineered peptide is derived from phage display, directed evolution, or rational design.

7. The polypeptide claim 1, wherein the intracellular effector domain is selected from any one of: a transcription factor, a fluorescent protein, a protein marker, an enzyme, an enzyme subdomain, a cytotoxic protein, a dominant negative polypeptide, a nucleic acid, a therapeutic protein, a peptide and protein fragment.

8. The polypeptide of claim 7, wherein the nucleic acid comprises an mRNA, an miRNA, an shRNA, an siRNA, a dsRNA, or an antisense nucleotide.

9. The polypeptide of claim 7, wherein the fluorescent protein comprises green fluorescence protein (GFP), yellow fluorescence protein (YFP), enhanced GFP (EGFP), enhanced YFP (EYFP), blue fluorescent protein (BFP), superfolder GFP (sfGFP), cyan fluorescent protein (ECFP), FITC, rhodamine, mCherry, mOrange, or mStrawberry.

10. The polypeptide of claim 7, wherein the enzyme comprises Cas9, dCas9, a zinc finger protease, a chemiluminescent enzyme, a therapeutic enzyme, a metabolic enzyme, an apoptotic enzyme, or a DNA repair enzyme.

11. The polypeptide of claim 7, wherein the cytotoxic protein comprises a pro-apoptotic protein, diphtheria toxin A fragment, botulinum toxin, exotoxin A, ricin A chain, abrin A chain, modeccin A chain, α-sacrin, curcin, crotin, gelonin, mitogillin, restrictocin, phenomycin, neomycin, a *Shigella* toxin, pertussis toxin, CagA, VopQ, or YopH.

12. The polypeptide of claim 7, wherein the therapeutic protein comprises replacement of a damaged or missing protein in a given disease or disorder.

13. The polypeptide of claim 1, wherein the intracellular effector domain further comprises an intracellular targeting or localization sequence.

14. The polypeptide of claim 13, wherein the intracellular targeting or localization sequence comprises a nuclear targeting sequence, a mitochondrial targeting sequence, an endoplasmic reticulum targeting sequence, a peroxisomal targeting sequence, a plasma membrane targeting sequence, a trans-Golgi targeting sequence or a lysosomal targeting sequence.

15. The polypeptide of claim 1, wherein the extracellular ligand binding domain further comprises at least a second target ligand binding site that does not bind the intramolecular peptide and binding of a target ligand to the second target ligand binding site does not induce cleavage of the intracellular effector domain,
   wherein the first target ligand binding site and the second target ligand binding site can bind the same target ligand or different target ligands, and
   wherein when a target ligand binds to the second target ligand binding site, at least one of the following occur;
   (i) the intramolecular peptide from the first target ligand binding site is easily displaced as compared to when the target ligand is not bound to the second target ligand binding site, or
   (ii) the first target ligand binding site avidity for the ligand increases and increases the length of time that the ligand binds to the first ligand binding site.

16. The polypeptide of claim 1, wherein the transmembrane domain comprises a Notch receptor transmembrane domain.

17. The polypeptide of claim 1, wherein the extracellular ligand binding domain comprises a receptor binding domain, an antibody binding domain, a single-chain variable fragments (scFv), a nanobody, a naturally occurring protein binding domain, a peptide, or a rationally designed protein with ligand affinity.

18. The polypeptide of claim 1, wherein the intramolecular peptide is soluble or tethered.

19. The polypeptide of claim 1, wherein the target ligand is an antigen, a drug, an analyte, a protein, a peptide, a nucleic acid, a glycoprotein, a small molecule, a carbohydrate, a lipid, a glycolipid, a lipoprotein, or a lipopolysaccharide.

20. A cell expressing the engineered receptor polypeptide of claim 1.

* * * * *

SEQUENCE LISTING

```
<160> NUMBER OF SEQ ID NOS: 58

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Gly Cys Gly Val Leu Leu Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Cys Gly Val Leu Leu Ser
1               5

<210> SEQ ID NO 3
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

His Leu Met Tyr Val Ala Ala Ala Ala Phe Val Leu Leu Phe Phe Val
1               5                   10                  15

Gly Cys Gly Val Leu Leu
            20

<210> SEQ ID NO 4
<211> LENGTH: 56
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ile Pro Tyr Lys Ile Glu Ala Val Lys Ser Glu Pro Val Glu Pro Pro
1               5                   10                  15

Leu Pro Ser Gln Leu His Leu Met Tyr Val Ala Ala Ala Ala Phe Val
            20                  25                  30

Leu Leu Phe Phe Val Gly Cys Gly Val Leu Leu Ser Arg Lys Arg Arg
        35                  40                  45

Arg Gln Leu Cys Ile Gln Lys Leu
    50                  55

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: Leu or Gln

<400> SEQUENCE: 5

Pro Xaa Gly Met Thr Ser
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Leu or Gln

<400> SEQUENCE: 6

Pro Xaa Gly Met Thr
1               5

<210> SEQ ID NO 7
<211> LENGTH: 343
<212> TYPE: PRT
<213> ORGANISM: Unknown
<220> FEATURE:
<223> OTHER INFORMATION: Description of Unknown:
      Cre recombinase sequence

<400> SEQUENCE: 7

Val Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220
```

```
Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
            245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 8
<211> LENGTH: 436
<212> TYPE: PRT
<213> ORGANISM: Unknown
<220> FEATURE:
<223> OTHER INFORMATION: Description of Unknown:
     FLPe recombinase sequence

<400> SEQUENCE: 8

```
Met Ser Gln Phe Asp Ile Leu Cys Lys Thr Pro Pro Lys Val Leu Val
1               5                   10                  15

Arg Gln Phe Val Glu Arg Phe Glu Arg Pro Ser Gly Glu Lys Ile Ala
            20                  25                  30

Ser Cys Ala Ala Glu Leu Thr Tyr Leu Cys Trp Met Ile Thr His Asn
        35                  40                  45

Gly Thr Ala Ile Lys Arg Ala Thr Phe Met Ser Tyr Asn Thr Ile Ile
    50                  55                  60

Ser Asn Ser Leu Ser Phe Asp Ile Val Asn Lys Ser Leu Gln Phe Lys
65                  70                  75                  80

Tyr Lys Thr Gln Lys Ala Thr Ile Leu Glu Ala Ser Leu Lys Lys Leu
                85                  90                  95

Ile Pro Ala Trp Glu Phe Thr Ile Ile Pro Tyr Asn Gly Gln Lys His
            100                 105                 110

Gln Ser Asp Ile Thr Asp Ile Val Ser Ser Leu Gln Leu Gln Phe Glu
        115                 120                 125

Ser Ser Glu Glu Ala Asp Lys Gly Asn Ser His Ser Lys Lys Met Leu
    130                 135                 140

Lys Ala Leu Leu Ser Glu Gly Glu Ser Ile Trp Glu Ile Thr Glu Lys
145                 150                 155                 160

Ile Leu Asn Ser Phe Glu Tyr Thr Ser Arg Phe Thr Lys Thr Lys Thr
                165                 170                 175

Leu Tyr Gln Phe Leu Phe Leu Ala Thr Phe Ile Asn Cys Gly Arg Phe
            180                 185                 190

Ser Asp Ile Lys Asn Val Asp Pro Lys Ser Phe Lys Leu Val Gln Asn
        195                 200                 205

Lys Tyr Leu Gly Val Ile Ile Gln Cys Leu Val Thr Glu Thr Lys Thr
    210                 215                 220

Ser Val Ser Arg His Ile Tyr Phe Phe Ser Ala Arg Gly Arg Ile Asp
```

```
                        225                 230                 235                 240
Pro Leu Val Tyr Leu Asp Glu Phe Leu Arg Asn Ser Glu Pro Val Leu
                245                 250                 255

Lys Arg Val Asn Arg Thr Gly Asn Ser Ser Asn Lys Gln Glu Tyr
            260                 265                 270

Gln Leu Leu Lys Asp Asn Leu Val Arg Ser Tyr Asn Lys Ala Leu Lys
        275                 280                 285

Lys Asn Ala Pro Tyr Pro Ile Phe Ala Ile Lys Asn Gly Pro Lys Ser
    290                 295                 300

His Ile Gly Arg His Leu Met Thr Ser Phe Leu Ser Met Lys Gly Leu
305                 310                 315                 320

Thr Glu Leu Thr Asn Val Val Gly Asn Trp Ser Asp Lys Arg Ala Ser
                325                 330                 335

Ala Val Ala Arg Thr Thr Tyr Thr His Gln Ile Thr Ala Ile Pro Asp
            340                 345                 350

His Tyr Phe Ala Leu Val Ser Arg Tyr Tyr Ala Tyr Asp Pro Ile Ser
        355                 360                 365

Lys Glu Met Ile Ala Leu Lys Asp Glu Thr Asn Pro Ile Glu Glu Trp
    370                 375                 380

Gln His Ile Glu Gln Leu Lys Gly Ser Ala Glu Gly Ser Ile Arg Tyr
385                 390                 395                 400

Pro Ala Trp Asn Gly Ile Ile Ser Gln Glu Val Leu Asp Tyr Leu Ser
                405                 410                 415

Ser Tyr Ile Asn Arg Arg Ile Gly Pro Val Glu Gln Lys Leu Ile Ser
            420                 425                 430

Glu Glu Asp Leu
        435

<210> SEQ ID NO 9
<211> LENGTH: 163
<212> TYPE: PRT
<213> ORGANISM: Unknown
<220> FEATURE:
<223> OTHER INFORMATION: Description of Unknown:
      Cas9 sequence

<400> SEQUENCE: 9

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140
```

```
Ser Thr Ala Thr Lys Asp Thr Tyr Asp Ala Leu His Met Gln Ala Leu
145                 150                 155                 160

Pro Pro Arg

<210> SEQ ID NO 10
<211> LENGTH: 125
<212> TYPE: PRT
<213> ORGANISM: Homo sapiens

<400> SEQUENCE: 10

Gly Asn Arg Ser Ser His Ser Arg Leu Gly Arg Ile Glu Ala Asp Ser
1               5                   10                  15

Glu Ser Gln Glu Asp Ile Ile Arg Asn Ile Ala Arg His Leu Ala Gln
            20                  25                  30

Val Gly Asp Ser Met Asp Arg Ser Ile Pro Pro Gly Leu Val Asn Gly
        35                  40                  45

Leu Ala Glu Asp Arg Asn Arg Asp Leu Ala Thr Ala Leu Glu Gln Leu
50                  55                  60

Leu Gln Ala Tyr Pro Arg Asp Met Glu Lys Glu Lys Thr Met Leu Val
65                  70                  75                  80

Leu Ala Leu Leu Leu Ala Lys Lys Val Ala Ser His Thr Pro Ser Leu
                85                  90                  95

Leu Arg Asp Val Phe His Thr Thr Val Asn Phe Ile Asn Gln Asn Leu
            100                 105                 110

Arg Thr Tyr Val Arg Ser Leu Ala Arg Asn Gly Met Asp
        115                 120                 125

<210> SEQ ID NO 11
<211> LENGTH: 7
<212> TYPE: PRT
<213> ORGANISM: Simian virus 40

<400> SEQUENCE: 11

Pro Lys Lys Lys Arg Lys Val
1               5

<210> SEQ ID NO 12
<211> LENGTH: 16
<212> TYPE: PRT
<213> ORGANISM: Unknown
<220> FEATURE:
<223> OTHER INFORMATION: Description of Unknown:
      Nucleoplasmin bipartite NLS sequence

<400> SEQUENCE: 12

Lys Arg Pro Ala Ala Thr Lys Lys Ala Gly Gln Ala Lys Lys Lys Lys
1               5                   10                  15

<210> SEQ ID NO 13
<211> LENGTH: 8
<212> TYPE: PRT
<213> ORGANISM: Unknown
<220> FEATURE:
<223> OTHER INFORMATION: Description of Unknown:
      NLS sequence

<400> SEQUENCE: 13

Met Val Pro Lys Lys Lys Arg Lys
1               5

<210> SEQ ID NO 14
<211> LENGTH: 17
```

```
<212> TYPE: PRT
<213> ORGANISM: Unknown
<220> FEATURE:
<223> OTHER INFORMATION: Description of Unknown:
      NLS sequence

<400> SEQUENCE: 14

Met Ala Pro Lys Lys Lys Arg Lys Val Gly Ile His Gly Val Pro Ala
1               5                   10                  15
Ala

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Cys Val Cys Ser Ser Asn Pro
1               5

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gln Thr Val Thr Thr Pro Leu
1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gln Glu Leu Ser Gln His Glu
1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Asn Ser Pro Ser Tyr Asn Pro
1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19
```

```
Gly Val Ser Gly Ser Lys Gly Gln
1               5

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gln Thr Thr Thr Thr Pro Leu
1               5

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gln Ile Phe Ser Arg Ser Ala
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gln Ile His Gly Leu Ser Pro
1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Ala Arg Ala Ser Val Leu Ser
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Cys Thr Leu Ser Ala Glu Glu
1               5

<210> SEQ ID NO 25
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 25

Gly Gln Asn Leu Ser Thr Ser Asn
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ala Ala Leu Thr Ile Leu Val
1               5

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Ala Ala Leu Thr Leu Leu Gly
1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Ala Gln Val Ser Ser Gln Lys
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ala Gln Leu Ser Arg Asn Thr
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Asn Ala Ala Ala Ala Lys Lys
1               5
```

```
<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Asn Glu Ala Ser Tyr Pro Leu
1               5

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gly Ser Ser Lys Ser Lys Pro Lys
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His His His His His
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 34

His His His His His His
1               5

<210> SEQ ID NO 35
<211> LENGTH: 10
<212> TYPE: PRT
<213> ORGANISM: Unknown
<220> FEATURE:
<223> OTHER INFORMATION: Description of Unknown:
      C-myc sequence

<400> SEQUENCE: 35

Glu Gln Lys Leu Ile Ser Glu Glu Asp Leu
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 36

Asp Tyr Lys Asp Asp Asp Lys
1               5

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Trp Ser His Pro Gln Phe Glu Lys
1               5

<210> SEQ ID NO 38
<211> LENGTH: 9
<212> TYPE: PRT
<213> ORGANISM: Homo sapiens

<400> SEQUENCE: 38

Tyr Pro Tyr Asp Val Pro Asp Tyr Ala
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Tyr Ile Arg Ser
1               5

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Phe His His Thr
1

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Trp Glu Ala Ala Ala Arg Glu Ala Cys Cys Arg Glu Cys Cys Ala Arg
1               5                   10                  15

Ala

<210> SEQ ID NO 42
<211> LENGTH: 27
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 42

Ala Pro Pro Asn Leu Trp Ala Ala Gln Arg Tyr Gly Arg Glu Leu Arg
1               5                   10                  15

Arg Met Ala Asp Glu Gly Glu Gly Ser Phe Lys
            20                  25

<210> SEQ ID NO 43
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Glu Leu Asp Glu Leu Val Tyr Leu Leu Asp Gly Pro Gly Tyr Asp
1               5                   10                  15

Pro Ile His Ser
            20

<210> SEQ ID NO 44
<211> LENGTH: 9
<212> TYPE: PRT
<213> ORGANISM: Homo sapiens

<400> SEQUENCE: 44

Tyr Pro Tyr Asp Val Pro Asp Tyr Ala
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Tyr Pro Tyr Asp Val Ala Asp Tyr Ala
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Tyr Pro Tyr Asp Val Pro Ala Tyr Ala
1               5

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47
```

```
Tyr Pro Tyr Asp Val Pro Asp Ala Ala
1               5

<210> SEQ ID NO 48
<211> LENGTH: 10
<212> TYPE: PRT
<213> ORGANISM: Unknown
<220> FEATURE:
<223> OTHER INFORMATION: Description of Unknown:
      Myc sequence

<400> SEQUENCE: 48

Glu Gln Lys Leu Ile Ser Glu Glu Asp Leu
1               5                   10

<210> SEQ ID NO 49
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Pro Val Glu Pro Pro Leu Pro Ser Gln Leu His Leu Met Tyr Val Ala
1               5                   10                  15

Ala Ala Ala Phe Val Leu Leu Phe Phe Val Gly Cys Gly Val Leu Leu
            20                  25                  30

Ser Arg Lys Arg Arg Arg
        35

<210> SEQ ID NO 50
<211> LENGTH: 23
<212> TYPE: PRT
<213> ORGANISM: Unknown
<220> FEATURE:
<223> OTHER INFORMATION: Description of Unknown:
      CD43 transmembrance domain sequence

<400> SEQUENCE: 50

Gly Met Leu Pro Val Ala Val Leu Val Ala Leu Leu Ala Val Ile Val
1               5                   10                  15

Leu Val Ala Leu Leu Leu Leu
            20

<210> SEQ ID NO 51
<211> LENGTH: 20
<212> TYPE: PRT
<213> ORGANISM: Unknown
<220> FEATURE:
<223> OTHER INFORMATION: Description of Unknown:
      CD44 transmembrance domain sequence

<400> SEQUENCE: 51

Leu Ile Ile Leu Ala Ser Leu Leu Ala Leu Ala Leu Ile Leu Ala Val
1               5                   10                  15

Cys Ile Ala Val
            20

<210> SEQ ID NO 52
<211> LENGTH: 21
<212> TYPE: PRT
<213> ORGANISM: Unknown
<220> FEATURE:
<223> OTHER INFORMATION: Description of Unknown:
      Klotho transmembrance domain sequence
```

<400> SEQUENCE: 52

Leu Leu Ala Phe Ile Ala Phe Leu Phe Phe Ala Ser Ile Ile Ser Leu
1               5                   10                  15

Ser Leu Ile Phe Tyr
            20

<210> SEQ ID NO 53
<211> LENGTH: 21
<212> TYPE: PRT
<213> ORGANISM: Unknown
<220> FEATURE:
<223> OTHER INFORMATION: Description of Unknown:
      VE-Cadheren transmembrance domain sequence

<400> SEQUENCE: 53

Ala Val Val Ala Ile Leu Leu Cys Ile Leu Thr Ile Thr Val Ile Thr
1               5                   10                  15

Leu Leu Ile Phe Leu
            20

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Glu Glu Met Glu Glu Cys
1               5

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Gly Gly Ser
1

<210> SEQ ID NO 56
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Glu Ala Ala Ala Lys
1               5

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Glu Asp Val Val Cys Cys
1               5

<210> SEQ ID NO 58
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Gly Ser
1
```